US011883575B2

(12) United States Patent
Wegener et al.

(10) Patent No.: US 11,883,575 B2
(45) Date of Patent: *Jan. 30, 2024

(54) SYSTEM AND METHOD FOR SELECTING AND CULTURING CELLS

(71) Applicant: Fenwal, Inc., Lake Zurich, IL (US)

(72) Inventors: Christopher J. Wegener, Libertyville, IL (US); Bret M. Olson, Chicago, IL (US); Alaina Schlinker, Chicago, IL (US); Steven Binninger, Evanston, IL (US); Avnie A. Kadakia, Chicago, IL (US); Kyle Thompson, Vernon Hills, IL (US); Kyle Wolok, Chicago, IL (US); Melanie Hamilton, Glenview, IL (US)

(73) Assignee: Fenwal, Inc., Lake Zurich, IL (US)

( * ) Notice: Subject to any disclaimer, the term of this patent is extended or adjusted under 35 U.S.C. 154(b) by 1154 days.

This patent is subject to a terminal disclaimer.

(21) Appl. No.: 16/576,484

(22) Filed: Sep. 19, 2019

(65) Prior Publication Data

US 2020/0009309 A1 Jan. 9, 2020

Related U.S. Application Data

(63) Continuation of application No. 15/498,918, filed on Apr. 27, 2017, now Pat. No. 10,449,283.
(Continued)

(51) Int. Cl.
*A61M 1/26* (2006.01)
*A61M 1/36* (2006.01)
(Continued)

(52) U.S. Cl.
CPC ............ *A61M 1/262* (2014.02); *A61M 1/265* (2014.02); *A61M 1/362* (2014.02);
(Continued)

(58) Field of Classification Search
CPC ...... C12M 47/04; C12M 29/14; C12M 41/48; C12M 33/14; C12M 23/28;
(Continued)

(56) References Cited

U.S. PATENT DOCUMENTS

| 4,710,472 A | * | 12/1987 | Saur | .......................... B03C 1/01 435/308.1 |
| 5,053,121 A | * | 10/1991 | Schoendorfer | ....... A61M 1/265 210/90 |

(Continued)

FOREIGN PATENT DOCUMENTS

| WO | WO 99/34848 | 7/1999 |
| WO | WO 01/45830 | 6/2001 |

(Continued)

OTHER PUBLICATIONS

GE Healthcare Life Sciences, WAVE Bioreactor™ 2/10 system, 6 pages (Aug. 2012).
(Continued)

*Primary Examiner* — Shogo Sasaki
(74) *Attorney, Agent, or Firm* — Cook Alex Ltd.

(57) ABSTRACT

A cell processing system includes at least one processor connectable to a source container filled with a biological fluid, the processor including a spinning membrane configured to receive and separate target cells from the biological fluid, the target cells exiting at a first outlet, first and second containers selectively connected to the first outlet; and a magnet. The system also includes a controller configured to operate the spinning membrane to receive biological fluid and to direct the target cells to the first container, to pause to permit magnetic particles to be associated with the target cells in the first container, to operate the spinning membrane to receive the contents of the first container with the magnet applied to the target cells associated with the magnetic (Continued)

particles, to remove or deactivate the magnet, and to transfer the target cells to the second container.

20 Claims, 25 Drawing Sheets

Related U.S. Application Data

(60) Provisional application No. 62/473,021, filed on Mar. 17, 2017, provisional application No. 62/437,243, filed on Dec. 21, 2016, provisional application No. 62/329,636, filed on Apr. 29, 2016.

(51) Int. Cl.
| | |
|---|---|
| C12M 1/00 | (2006.01) |
| C12M 1/26 | (2006.01) |
| C12M 1/36 | (2006.01) |
| G01N 33/543 | (2006.01) |

(52) U.S. Cl.
CPC .......... *A61M 1/3618* (2014.02); *C12M 23/28* (2013.01); *C12M 29/14* (2013.01); *C12M 33/14* (2013.01); *C12M 41/48* (2013.01); *C12M 47/04* (2013.01); *G01N 33/54326* (2013.01); *G01N 33/54366* (2013.01)

(58) Field of Classification Search
CPC ....... G01N 33/54366; G01N 33/54326; A61M 1/3618; A61M 1/265; A61M 1/262
See application file for complete search history.

(56) References Cited

U.S. PATENT DOCUMENTS

| | | | | |
|---|---|---|---|---|
| 5,194,145 A * | 3/1993 | Schoendorfer | ...... | B01D 61/025 210/651 |
| 5,536,475 A * | 7/1996 | Moubayed | ....... | G01N 33/56966 209/225 |
| 5,647,985 A * | 7/1997 | Ung-Chhun | ........ | A61M 1/3679 422/535 |
| 5,738,792 A | 4/1998 | Schoendorfer | | |
| 5,762,791 A * | 6/1998 | Deniega | ................ | A61M 1/306 210/90 |
| 5,972,217 A * | 10/1999 | Ung-Chhun | ....... | B01D 39/1692 210/504 |
| 6,143,577 A * | 11/2000 | Bisconte Sconte De Saint Julien | .............. | G01N 33/54326 436/806 |
| 6,251,284 B1 * | 6/2001 | Bischof | ................. | A61M 1/341 604/4.01 |
| 6,251,295 B1 * | 6/2001 | Johnson | .............. | A61M 1/3692 210/651 |
| 6,358,474 B1 * | 3/2002 | Dobler | ................... | G01N 1/286 435/270 |
| 6,423,023 B1 * | 7/2002 | Chang | ................. | A61M 1/3496 210/780 |
| 6,497,821 B1 * | 12/2002 | Bellamy, Jr. | .......... | A61M 1/265 210/138 |
| 6,527,957 B1 * | 3/2003 | Deniega | ............... | A01N 1/0242 210/651 |
| 6,706,008 B2 * | 3/2004 | Vishnoi | ........... | A61M 1/362265 604/4.01 |
| 6,808,503 B2 * | 10/2004 | Farrell | ................. | A61M 1/3675 210/741 |
| 6,863,821 B2 * | 3/2005 | Moriarty | ............. | A61M 1/3417 210/780 |
| 6,960,178 B2 * | 11/2005 | Chang | ..................... | A61M 1/26 210/780 |
| 6,969,367 B2 * | 11/2005 | Tu | ......................... | B01D 63/16 210/780 |
| 6,994,781 B2 * | 2/2006 | Cork | ................... | A61M 1/3609 436/63 |
| 7,364,921 B1 * | 4/2008 | Sciorra | ............ | G01N 33/54333 436/501 |
| 7,390,484 B2 * | 6/2008 | Fraser | .................... | C12N 5/069 606/1 |
| 7,442,303 B2 * | 10/2008 | Jacobson | ............... | B01D 71/64 264/494 |
| 7,470,245 B2 * | 12/2008 | Tu | ........................ | A61M 1/3683 604/4.01 |
| 7,514,075 B2 * | 4/2009 | Hedrick | ................. | A61K 35/28 606/1 |
| 7,585,670 B2 * | 9/2009 | Hedrick | ................. | A61B 17/00 606/1 |
| 7,771,716 B2 * | 8/2010 | Hedrick | ................. | A61L 27/54 606/1 |
| 8,105,580 B2 | 1/2012 | Fraser et al. | | |
| 8,137,903 B2 * | 3/2012 | Kaufman | ......... | G01N 33/54326 210/695 |
| 8,404,229 B2 * | 3/2013 | Fraser | ................. | A61L 27/3834 435/366 |
| 8,481,336 B2 * | 7/2013 | Earhart | ................. | C12N 13/00 210/488 |
| 8,637,004 B2 * | 1/2014 | Danilkovich | ........... | A61P 43/00 435/325 |
| 8,727,132 B2 * | 5/2014 | Miltenyi | ............ | G01N 35/0098 494/67 |
| 8,747,290 B2 | 6/2014 | Miltenyi et al. | | |
| 8,808,978 B2 * | 8/2014 | Pages | .................. | A61M 1/3692 435/283.1 |
| 8,951,782 B2 * | 2/2015 | Chang | .................... | C12M 47/04 435/283.1 |
| 9,217,131 B2 * | 12/2015 | Lamish | .................. | C12M 47/02 |
| 9,452,254 B2 * | 9/2016 | Kimura | .................. | B04B 11/02 |
| 9,511,094 B2 | 12/2016 | Fraser et al. | | |
| 9,597,395 B2 * | 3/2017 | Fraser | .................... | A61K 35/28 |
| 2005/0048035 A1 * | 3/2005 | Fraser | .................... | A61L 27/56 435/368 |
| 2005/0048036 A1 * | 3/2005 | Hedrick | ................. | A61K 35/28 424/93.7 |
| 2010/0006509 A1 * | 1/2010 | Hornes | ................. | B03C 1/0335 210/695 |
| 2010/0112695 A1 * | 5/2010 | Min | ....................... | C12M 45/02 435/308.1 |
| 2010/0112696 A1 * | 5/2010 | Min | ....................... | C12M 45/09 435/378 |
| 2012/0055854 A1 * | 3/2012 | Tibbe | ....................... | B03C 1/01 209/214 |
| 2012/0132593 A1 * | 5/2012 | Murthy | .................. | C12M 47/02 209/636 |
| 2013/0017538 A1 * | 1/2013 | Ionescu-Zanetti | ...... | B03C 1/288 435/6.12 |
| 2013/0092630 A1 * | 4/2013 | Wegener | ............. | A61M 1/265 210/90 |
| 2014/0370491 A1 * | 12/2014 | Radwanski | ......... | A61M 1/3696 435/2 |
| 2015/0118728 A1 * | 4/2015 | Rahman | ............ | B01L 3/502753 422/534 |
| 2016/0113967 A1 * | 4/2016 | Hedrick | ................. | A61P 43/00 435/173.9 |
| 2016/0244714 A1 * | 8/2016 | Spuhler | .............. | G01N 15/1463 |
| 2016/0355777 A1 * | 12/2016 | Fachin | .................... | A61P 35/00 |
| 2017/0262601 A1 * | 9/2017 | Binninger | .............. | G16H 10/40 |
| 2017/0268037 A1 * | 9/2017 | Ionescu-Zanetti | .... | B03C 1/0332 |
| 2017/0313968 A1 * | 11/2017 | Wegener | ............. | A61M 1/3496 |
| 2017/0340783 A1 * | 11/2017 | Wegener | ............. | A61M 1/3692 |
| 2018/0015418 A1 * | 1/2018 | Binninger | ............. | B01D 61/22 |

FOREIGN PATENT DOCUMENTS

| | | |
|---|---|---|
| WO | WO 01/83002 A2 | 11/2001 |
| WO | WO 01/83002 A3 | 11/2001 |
| WO | WO 2010/075061 A2 | 7/2010 |
| WO | WO 2010/075061 A3 | 7/2010 |
| WO | WO 2012/125457 | 9/2012 |
| WO | WO 2012/125470 | 9/2012 |

(56) References Cited

OTHER PUBLICATIONS

Hollyman et al., Manufacturing Validation of Biologically Functional T Cells Targeted to CD19 Antigen for Autologous Adoptive Cell Therapy, Journal of Immunotherapy, vol. 32, No. 2, 169-180 (Feb.-Mar. 2009).
Levine et al., Large-Scale Production of CD4 + T Cells from HIV-1-Infected Donors After CD3/CD28 Costimulation, Journal of Hematotherapy 7:437-448 (1998).
ThermoFisher Scientific, DynaMag™ CTS™ Magnet, User Guide, 28 pages (May 25, 2015).
Thompson et al., A Phase 1 Trial of CD3/CD28-activated T Cells (Xcellerated T Cells) and Interleukin-2 in Patients with Metastatic Renal Cell Carcinoma, Clinical Cancer Research, vol. 9, pp. 3562-3570 (Sep. 1, 2003).
White et al., Intravenous Safety Study in Rats Given Paramagnetic, Polystyrene Beads with Covalently Bound Sheep Anti-Mouse Immunoglobulin G (IgG), Journal of the American College of Toxicology 14(4):251-265 (1995).
European Patent Office, extended European Search Report, counterpart EP Appl. No. 17168430.1, dated Sep. 15, 2017.
Wegener et al., U.S. Appl. No. 15/498,965, filed Apr. 27, 2017.

\* cited by examiner

|  |  | # of Wash Cycles | Wash Cycle #1 Settings ||||  Wash Cycle #2 Settings  ||||
|---|---|---|---|---|---|---|---|---|---|---|
|  |  |  | Spinner Inlet Flow Rate (mL/min) | Reduction Spinner Revolution Rate (rpm) | Desired Spinner Inlet PCV | Reduction Retentate Pump Rate (mL/min) | Spinner Inlet Flow Rate (mL/min) | Reduction Spinner Revolution Rate (rpm) | Desired Spinner Inlet PCV | Reduction Retentate Pump Rate (mL/min) |
| Settings #1 | Procedure #1 | 2 | 150 | 3750 | 3% | 15 | 150 | 3750 | 3% | 15 |
|  | Procedure #2 | 2 | 150 | 3750 | 3% | 15 | 150 | 3750 | 3% | 15 |
| Settings #2 | Procedure #1 | 2 | 80 | 4000 | 6% | 8 | 80 | 4000 | 6% | 8 |
|  | Procedure #2 | 2 | 80 | 4000 | 6% | 8 | 80 | 4000 | 6% | 8 |
| Settings #3 | Procedure #1 | 2 | 80 | 4000 | 6% | 8 | 80 | 4000 | 6% | 8 |
|  | Procedure #2 | 2 | 148 | 2750 | 7% | 16 | 148 | 2750 | 7% | 16 |

*FIG. 5B*

| | | Wash Cycle #1 Settings | | | Wash Cycle #2 Settings | | | Wash Cycle #1 Settings | | | |
|---|---|---|---|---|---|---|---|---|---|---|---|
| | # of Wash Cycles | Spinner Inlet Flow Rate (mL/min) | Reduction Spinner Revolution Rate (rpm) | Desired Spinner Inlet PCV | Reduction Retentate Pump Rate (mL/min) | Spinner Inlet Flow Rate (mL/min) | Reduction Spinner Revolution Rate (rpm) | Desired Spinner Inlet PCV | Reduction Retentate Pump Rate (mL/min) | Spinner Inlet Flow Rate (mL/min) | Reduction Spinner Revolution Rate (rpm) | Desired Spinner Inlet PCV | Reduction Retentate Pump Rate (mL/min) |
| Settings #4 Procedure | 3 | 80 | 4000 | 6% | 8 | 80 | 4000 | 6% | 8 | 148 | 2750 | 7% | 16 |

*FIG. 6B*

SYSTEM AND METHOD FOR SELECTING AND CULTURING CELLS

CROSS-REFERENCE TO RELATED APPLICATIONS

This application is a continuation of U.S. application Ser. No. 15/498,918, filed Apr. 27, 2017, now U.S. Pat. No. 10,449,283, which claims the benefit of U.S. Provisional Application No. 62/329,636, filed Apr. 29, 2016, No. 62/437,243, filed Dec. 21, 2016, and No. 62/473,021, filed Mar. 17, 2017, all of which are hereby incorporated herein by reference in their entirety.

TECHNICAL FIELD

The present disclosure is generally directed to a system and method for separation of a cell of interest or a target cell from a collection of cells, and in particular a system and method for separation of the target cell using an attachable bead to permit automated size and/or magnetic selection of target cells, and also growth of target cell populations.

BACKGROUND

The processing of biological fluid such as blood or blood components may involve using a reusable processing apparatus ("hardware") and a disposable fluid circuit adapted for mounting or other association with the reusable apparatus. The fluid circuit typically includes containers such as plastic bags and associated tubing that defines a flow path through the circuit. The disposable fluid circuit may also include one or more separation devices where the biological fluid/cells can be separated into two or more components, washed or otherwise processed. Separation devices may separate the biological fluid based on centrifugal separation and/or, as described below, membrane separation.

SUMMARY

According to an aspect, a cell processing system includes at least one processor connectable to a source container filled with a biological fluid, and a controller coupled to the at least one processor. The at least one processor includes a spinning membrane configured to receive and separate target cells from the biological fluid, the target cells exiting at a first outlet, at least a first container and a second container selectively connected to the first outlet, and a magnet. The controller is configured to operate the spinning membrane to receive biological fluid from the source container and to direct the target cells to the first container, to pause operation of the processor to permit magnetic particles to be associated with the target cells in the first container, to operate the spinning membrane to receive the contents of the first container with the magnet applied to the target cells associated with the magnetic particles in the first container, to remove and/or deactivate the magnet applied to the target cells associated with the magnetic particles in the first container, to transfer the target cells to the second container after removal and/or deactivation of the magnet, and to prompt an operator to remove the second container after the target cells are transferred to the second container.

According to another aspect, a method of operating a cell processing system is provided, the cell processing system including at least one processor connectable to a source container filled with a biological fluid, the at least one processor including a spinning membrane configured to receive and separate target cells from the biological fluid, the target cells exiting at a first outlet, at least a first container and a second container selectively connected to the first outlet, and a magnet; and a controller coupled to the at least one processor. The method includes operating the spinning membrane to receive biological fluid from the source container and to direct the target cells to the first container, pausing operation of the processor to permit magnetic particles to be associated with the target cells in the first container, operating the spinning membrane to receive the contents of the first container with the magnet applied to the target cells associated with the magnetic particles in the first container, removing and/or deactivating the magnet applied to the target cells associated with the magnetic particles in the first container, transferring the target cells to a second container after removal and/or deactivation of the magnet, and prompting an operator to remove the second container after the target cells are transferred to the second container.

BRIEF DESCRIPTION OF THE FIGURES

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

FIG. 5B is a tabular listing of settings to be used in the steps illustrated in FIG. 5A for a reusable hardware apparatus and its controller, according to an exemplary embodiment.

FIG. 6B is a tabular listing of settings to be used in the steps illustrated in FIG. 6A for a reusable hardware apparatus and its controller, according to an exemplary embodiment.

DETAILED DESCRIPTION

Figure 1:
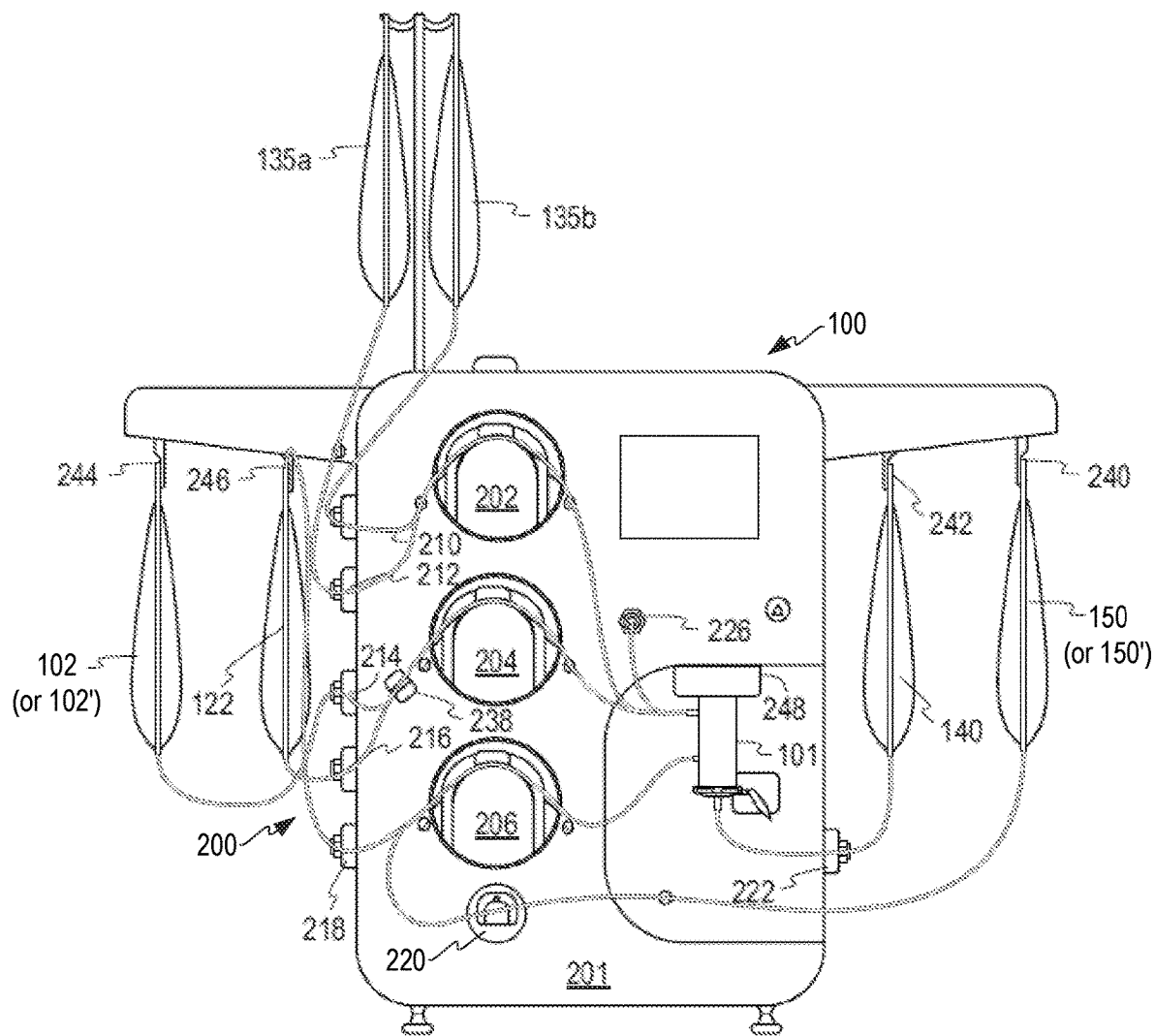
FIG. 1 is a frontal view of a reusable cell processing system with a disposable fluid circuit loaded thereon.

There are several aspects of the present subject matter that may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

One or more embodiments described herein may allow for a single system for washing and processing cell products in preparation for target cell selection of those cell products.

Systems and methods for the automated sterile processing of biological fluid are disclosed herein. The systems disclosed may include a reusable separation apparatus and one or more disposable processing circuits adapted for association with the reusable apparatus. The reusable separation apparatus may be any apparatus that can provide for the automated processing of biological fluid. By "automated," it is meant that the apparatus can be programmed to carry out the processing steps of a biological fluid processing method without substantial operator involvement. Even in the automated system of the present disclosure, it should be understood that some operator involvement may be required, such as the loading of the disposable fluid circuits and entering processing parameters. Additional manual steps may be required as well. However, the reusable apparatus may be programmed to process biological fluid through each of the disposable circuits described below without substantial operator intervention.

The illustrated reusable processing apparatus may be capable of effecting the separation of a biological fluid that includes biological cells into two or more components or fractions. Thus, the reusable apparatus may generate conditions that allow for the separation of a biological fluid into selected components or fractions. In one embodiment, an apparatus that uses a spinning porous membrane to separate one component from other components may be used for separating biological fluid into its constituent components or fractions. An example of such machine is the Autopheresis C® sold by Fenwal, Inc. of Lake Zurich, Illinois, which is an affiliate of Fresenius Kabi AG of Bad Homburg, Germany. A detailed description of a spinning membrane may be found in U.S. Pat. No. 5,194,145 to Schoendorfer, which is incorporated by reference herein in its entirety, and in International (PCT) Application No. PCT/US2012/028492, filed Mar. 9, 2012, the contents of which are also incorporated herein in its entirety. In addition, systems and methods that utilize a spinning porous membrane are also disclosed in U.S. Provisional Patent Application No. 61/537,856, filed on Sep. 22, 2011, and International (PCT) Application No. PCT/US2012/028522, filed Mar. 9, 2012, the contents of each which are incorporated herein by reference in their entireties. In another embodiment, the reusable apparatus may generate a centrifugal field to effect separation.

Figure 2:
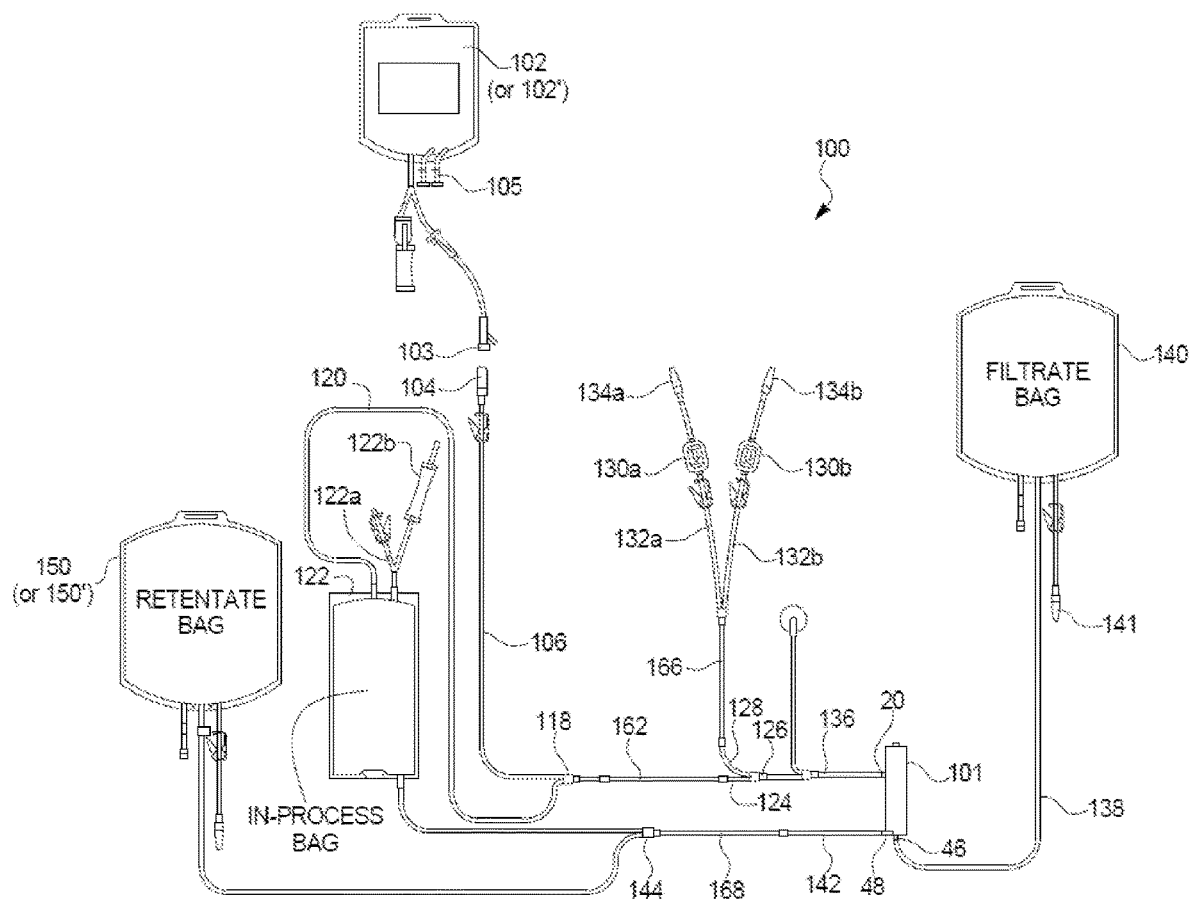
FIG. 2 is a schematic view of one embodiment of a disposable fluid circuit useful in the systems and methods described herein.

As illustrated in FIGS. 1 and 2, an embodiment of a cell processing system includes a processor 100, 200 to receive a biological fluid to be processed. The illustrated embodiments of the processor may include a disposable processing fluid circuit 100 (see also FIG. 2) and reusable hardware 200 (see also FIG. 3). According to the illustrated embodiments in FIGS. 1 and 2, the disposable fluid circuit 100 may include a first separator in the form of a spinning membrane 101, at least one container 102, 122, 135a, 135b, 140, 150 and tubing 106, 120, 128, 132a, 132b, 162, 166, 168, which tubing connects the spinning membrane 101 and the one or more containers 102, 122, 135a, 135b, 140, 150 and defines fluid pathways. As is also illustrated, the reusable hardware 200 may include at least one drive 248 to spin the spinning membrane 101, at least one scale 240, 242, 244, 246 to weigh the at least container 150, 140, 102, 122 and contents thereof, and at least one pump 202, 204, 206 to receive the tubing 162, 166, 168 and pump fluid through the tubing 162, 166, 168 by peristaltic action, for example, although other types of pumps and pumping action may be used. See FIG. 3.

Turning first to FIG. 2, a disposable circuit 100 may be used for the separation, washing, volume reduction and/or other processing of a biological fluid. While the circuits described herein may be used as stand-alone circuits, at least two or more disposable fluid circuits may be used in combination and in series for the separation, washing, volume reduction and/or other processing of a biological fluid. The circuit 100 may be a "closed" system or circuit, in which the interior of the system, e.g., the flow paths, container, etc., are not exposed or "opened" to the outside environment; the circuit 100 may be referred to as closed even where additional containers are attached to the circuit 100, for example before or during a procedure. Circuit 100 may include an integrated separation device, such as, but not limited to, a spinning membrane 101 as described above. Circuit 100 may also include waste/filtrate container 140, product/retentate container 150, and in-process container 122. Disposable fluid circuits may further include sampling assemblies (not shown) for collecting samples of source biological fluid, "final" product, or other intermediate products obtained during the biological fluid processing.

As will be seen in the Figures and described in detail below, the disposable fluid processing circuits include tubing that defines flow paths or fluid pathways throughout the circuits, as well as access sites for sterile and/or other connection to containers of processing solutions, such as wash solutions, treating agents, and/or sources of biological fluid. As shown in FIG. 2, the tubing of circuit 100 may include spaced tubing segments 162, 166, 168. The tubing segments are provided for mating engagement with, e.g., the peristaltic pumps 202, 204, 206 of the reusable hardware apparatus 200 (see, e.g., FIG. 1). The containers and the plastic tubing may be made of conventional medical grade plastic that can be sterilized by sterilization techniques commonly used in the medical field, e.g., radiation, autoclaving, etc. Plastic materials useful in the manufacture of containers and of the tubing in the circuits disclosed herein may include plasticized polyvinyl chloride, acrylics, and/or polyolefins.

Source containers may be attached in sterile fashion to the circuit 100. A source container 102 for connection to one disposable circuit may be a product container 150 of another circuit used in a different and/or earlier step of the overall method of processing. Alternatively, the contents of a product container 150 may be further processed or separated and then transferred in sterile fashion to a source container 102 of a later-in-series fluid circuit.

The biological cell suspension to be washed and/or otherwise treated may be provided in a source container 102, shown in FIG. 2. In one embodiment, the source container 102 may initially be disconnected from the disposable set, and may be attached (in sterile fashion) at the time of use. Source container 102 may have one or more access sites 103, 105, one of which may be adapted for (sterile) connection to fluid circuit 100 at docking site 104. Source container 102 may be attached in a sterile manner by employing sterile docking devices, such as the CompoDock, available from Fresenius Kabi AG, the BioWelder, available from Sartorius AG, or the SCD IIB Tubing Welder, available from Terumo Medical Corporation. A second access port 105 may also be provided for extracting fluid from the source container 102 and/or introducing materials into the source container 102.

As shown in FIG. 2, tubing segment 106 extends from docking site 104 and is connected to further downstream branched-connector 118. Branched-connector 118 may communicate with tubing 106 and tubing 120, which may provide a fluid flow path from an "in-process" container 122 described in greater detail below. Tubing segment 124 extends from branched-connector 118 and is joined to a port of further downstream branched-connector 126. A separate flow path defined by tubing 128 may also connect to a port of branched-connector 126.

In accordance with the fluid circuit of FIG. 2, one or more containers of wash or other processing/treating solution may be attached (or pre-attached) to set 100. As illustrated in FIG. 2, tubings 132*a*, 132*b* (defining a flow path) may include and terminate in an access site such as spike connectors 134*a*, 134*b*. Access sites 134*a*, 134*b* may establish flow communication with containers 135*a*, 135*b* (shown in FIG. 1) of a wash fluid, e.g., saline, additive solution, buffer, etc. As one example, the wash fluid or medium may comprise a buffer comprising PBS, EDTA, HSA and/or saline. Tubings 132*a*, 132*b* may include in-line sterile barrier filters 130*a*, 130*b* for filtering any particulate from a fluid before it enters the flow path leading to and/or from second branched-connector 126 and, separator 101. The wash media/fluid may flow from the wash fluid source through tubing segments 132*a*, 132*b* where it may be filtered by the sterile barrier filters 130*a*, 130*b*, and then may pass through tubing 128 to the input of the branched-connector 126.

Tubing segment 136 may define a flow path connected at one end to branched-connector 126 and to an inlet port 20 of the separator 101. As shown in FIG. 2 (and described in greater detail in connection with FIG. 4), the spinning membrane separator 101 may have at least two outlet ports. Outlet 46 of separator 101 may receive waste from the wash (e.g., diluted suspension media) and may be connected to tubing 138, which may define a flow path to filtrate/waste product container 140. The filtrate/waste product container 140 may include a further connection port 141 for sampling or withdrawing the waste from within the waste/filtrate container 140.

Separation device 101 may include a second outlet 48 that is connected to tubing segment 142 for directing the desired biological cell/fluid product to the in-process container(s) 122 or the product/retentate container 150. To permit this, the other end of tubing segment 142 may be connected to branched-connector 144, which may branch into and define a flow path to one or more in-process containers 122 and a flow path to the "final" product/retentate container 150. The product container 150 may also include a sampling assembly (not shown).

Figure 3:
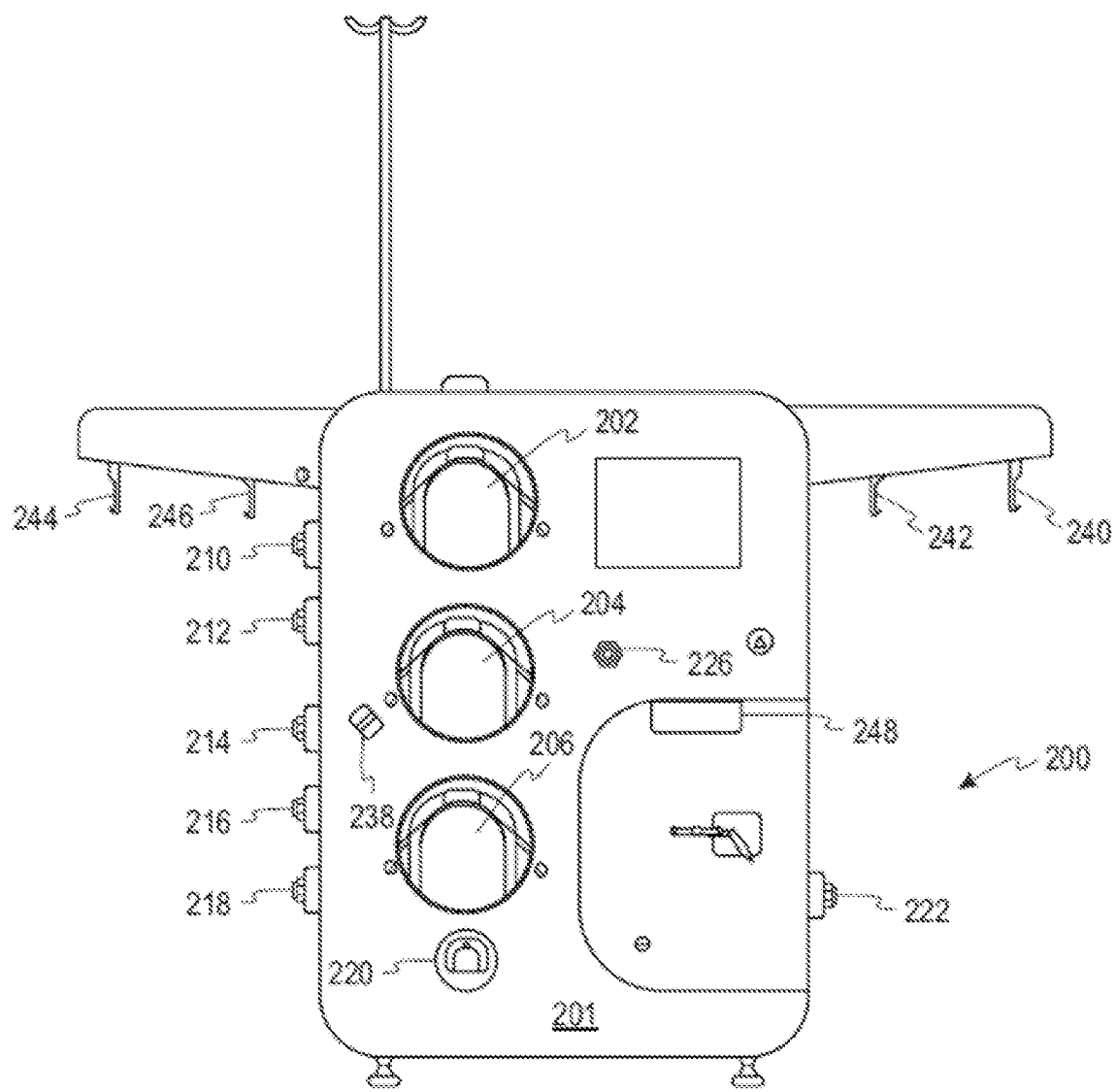
FIG. 3 is a frontal view of the reusable cell processing apparatus.

Turning to FIG. 3, a front panel 201 of a reusable hardware processing apparatus 200, also referred to herein as "hardware", is shown. Apparatus 200 may be of compact size suitable for placement on a tabletop of a lab bench and adapted for easy transport. Apparatus 200 may also be supported by a pedestal that can be wheeled to a desired location. As shown in FIG. 3, apparatus 200 may include a plurality of peristaltic pumps such as pumps 202, 204 and 206 on front panel 201, which pumps 202, 204, 206 may be bi-directional peristaltic pumps. Pump segments of the disposable fluid circuit (described above) may be selectively associated with peristaltic pumps 202, 204, and 206. The peristaltic pumps may articulate with the fluid set of FIG. 2 at the pump segments identified by reference numerals 162, 166, 168 and advance the cell suspension or other fluid within the disposable set, as will be understood by those of skill in the art. Apparatus 200 may also include clamps 210, 212, 214, 216, 218, 220 and 222. The clamps may be used to control the flow of the cell suspension through different segments of the disposable set.

Apparatus 200 may also include several sensors to measure various conditions. The output of the sensors may be utilized by device 200 to operate one or more wash or processing cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at, e.g., tubing segment 136), to monitor pressure inside separator 101. Air detector sensor 238 may also be associated with the disposable set 100, as necessary. Air detector 238 may be optional and may be provided to detect the location of fluid/air interfaces.

Apparatus 200 may include weight scales 240, 242, 244, and 246 from which the product container 150, the waste container 140, the source container 102, the in-process container 122, and any additional container(s) may depend and be weighed (see FIG. 1). The weights of the bags may be monitored by weight sensors and recorded during a washing or other procedure. From measurements of the weight sensors, the device may determine whether a container is empty, partially full, or full and may control the components of apparatus 200, such as the peristaltic pumps 202, 204 and 206 and clamps 210, 212, 214, 216, 218, 220 and 222.

Figure 4:
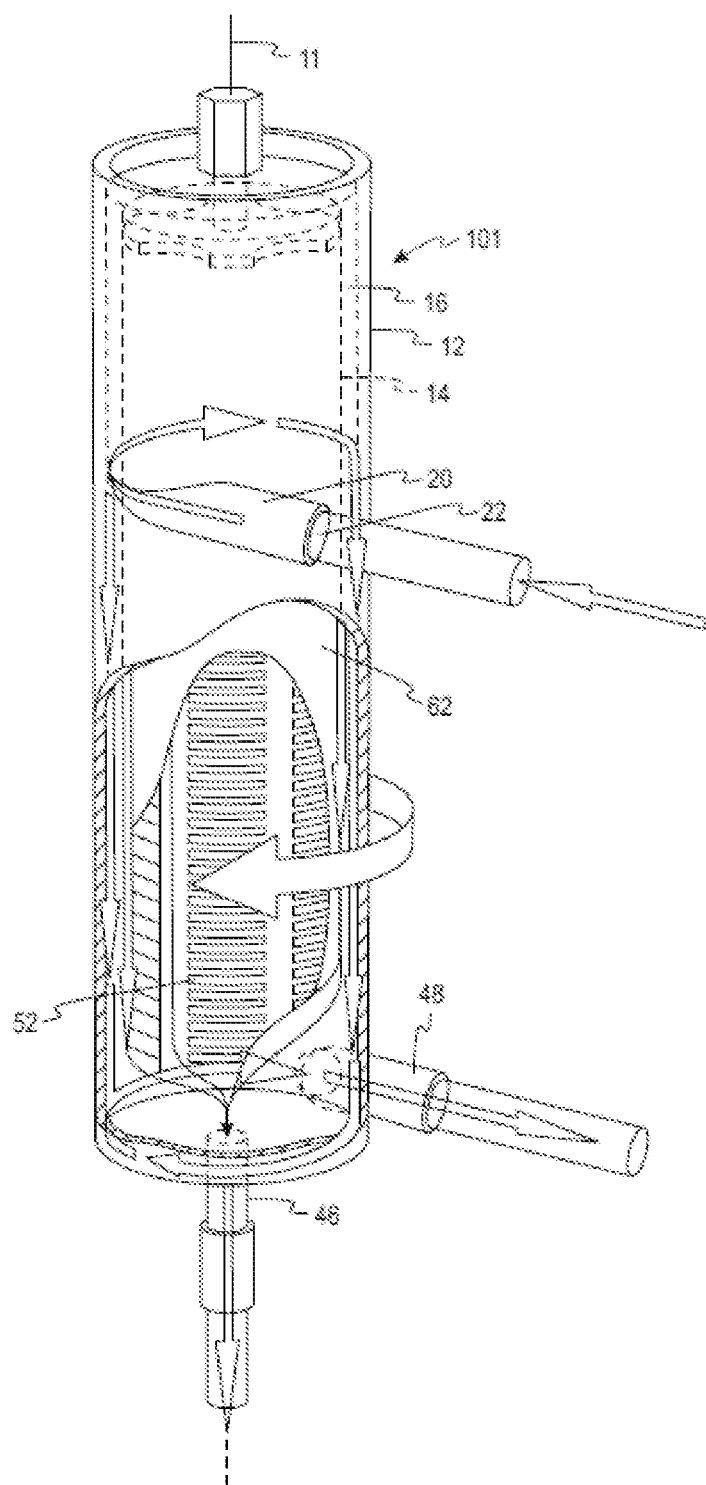
FIG. 4 is a perspective view of a separation/washing device using a spinning membrane.

Apparatus 200 may include a drive unit or "spinner" 248, which may cause the indirect driving of the spinning membrane separator 101. Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator may cause the spinner within the housing of the spinning membrane separator to rotate. FIG. 4 shows a spinning membrane separator 101 to be used with the spinner 248. Separator 101 may form part of the disposable circuit 100. Examples and details relating to spinning membrane separators and spinners are disclosed in the aforementioned U.S. Pat. No. 5,194,145, International Application No. PCT/US2012/

028492, U.S. Provisional Patent Application No. 61/537,856, and International (PCT) Application No. PCT/US2012/028522.

Device 101 may include a generally cylindrical housing 12, mounted concentrically about a longitudinal vertical central axis. An internal member 14 may be mounted concentric with the central axis 11. Housing 12 and internal member 14 may be relatively rotatable. As illustrated, the housing 12 may be stationary and internal member 14 may be a rotating spinner that is rotatable concentrically within cylindrical housing 12, as shown by the thick arrow in FIG. 4. The boundaries of the blood flow path are generally defined by gap 16 between the interior surface of housing 12 and the exterior surface of rotary spinner 14. The spacing between the housing and the spinner is sometimes referred to as the shear gap. In one embodiment, the shear gap may be approximately 0.02-0.06 inches (0.05-0.15 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example, preferably an increasing gap width in the direction. Such a gap width may range from about 0.02 to about 0.075 inches (0.05-0.19 cm). The gap width could be varied by varying the outer diameter of the rotor and/or the inner diameter of the facing housing surface. The gap width could change linearly or stepwise or in some other manner as may be desired. In any event, the width dimension of the gap may be selected so that at the desired relative rotational speed, Taylor Couette flow, such as Taylor vortices, are created in the gap.

Biological fluid may be fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 48. Cylindrical housing 12 may be completed by a bottom end housing terminating in an outlet orifice 46 concentric with the central axis.

The surface of the rotary spinner 14 may be at least partially, substantially, or entirely, covered by a cylindrical porous membrane 62. The membrane 62 may have a nominal pore size of approximately 4.0 microns (μm), but other pore sizes, for example, of from 0.8 microns to 30.0 microns, may alternatively be used. Membranes useful in the washing methods described herein may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In one embodiment, the nylon membrane may have a pore size of approximately 2.0 μm or less and a thickness of approximately 10 μm or greater. Membranes of this type may retain cellular components (e.g., red blood cells, white blood cells) as well as certain formed blood components, e.g., platelets (~2-4 μm). In another embodiment, the membrane may be made of a thin (approximately 10-50 micron (μm) thick) sheet of, for example, unsupported polycarbonate. In this embodiment, pores (holes) may be cylindrical and larger than those described above, e.g., 4.0 μm. The pores may be sized to allow small formed components (e.g., platelets, microparticles, etc.) to pass through, while the desired cells (e.g., white blood cells and larger red blood cells) are collected.

Apparatus 200 and circuit 100 may be used for processing, washing, treating, supernatant exchange, volumetric manipulation, and incubation of biological cells, such as leukocytes, lymphocytes, mononuclear cells, etc., for subsequent therapeutic administration. The steps performed by apparatus 200 may be controlled by a controller, e.g., a microprocessing unit driven by software, with certain steps performed by an operator. For example, the apparatus 200, when switched on, may conduct self-calibration checks, including the checking of the peristaltic pumps, clamps, and sensors. Apparatus 200 may then prompt the user to enter selected procedural parameters, such as the washing procedure to be performed, the amount of cell suspension to be washed, the number of washings to take place, etc. The operator may then select and enter the procedural parameters for the wash procedure.

The microprocessing unit may calculate the volume of wash solution needed for the procedure based on a "maximum output concentration" for the separator, defined as the maximum ratio of the volume of cellular material to the volume of the cell suspension that can be processed by the separator without losing cells of interest. The maximum output concentration may be a function of factors such as the configuration of the membrane, the pore size, and speed of rotation of the membrane. This may be determined or derived empirically for a particular spinner configuration, and pre-programmed into the microprocessor, or a value may be input by the system operator. For purposes of illustration, it will be assumed that the maximum output concentration for the spinning membrane separator is 30% cellular material.

A "concentration ratio," defined as the ratio of the volume of the input to the separator to the output of the separator for the procedure, may be determined. This value may be directly input into the controller by the system operator, or it may be automatically determined by the controller based on other operator input selections. For example, for frozen or thawed cell products, the system may use a concentration ratio of 2:1, while for fresh cell products the concentration ratio used by the system may be 10:1. The input to the separator may be determined by a "spinner inlet flow rate" that may be set by an operator or configured automatically. The output of the separator may be determined by a "reduction retentate pump rate" (also called "spinner outlet flow rate") that may likewise be set by an operator or configured automatically.

A "maximum input concentration," also called "desired inlet spinner packed cell volume (PCV)," may be determined as a function of the maximum output concentration and the concentration ratio, specifically the maximum output concentration divided by the concentration ratio. The desired inlet spinner PCV may indicate the maximum density of cells allowed to enter the separator module to manage the density of cells that exit the spinner. The desired inlet spinner PCV may be set by an operator. During the washing procedure, washing solution may be added to the cells to be washed in an amount so that the cellular concentration of the input to the separator does not exceed the maximum input concentration. By way of example, if the maximum output concentration is 30% and fresh cell products are to be washed, for which the concentration ratio is 10:1, the maximum input concentration is 30%÷10=3%. Thus the volume of wash solution necessary for the procedure should be sufficient to dilute the suspension being input to the separator to a 3% cellular concentration, resulting in an output concentration that does not exceed 30%, and a container 135 containing at least this volume of wash solution should be connected to the disposable set 100 prior to the start of the wash procedure.

A "reduction spinner revolution rate" may be described in revolutions per minute (rpm) and is a measurement of how fast the spinner is spinning. The reduction spinner revolution rate of the spinner may affect how tight the Taylor vortices and how closely target cells reach the membrane. Higher reduction spinner revolution rates may lead to tighter Taylor vortices, leading to decreased mean size of cells retained (not passing through the membrane), and lower reduction spinner revolution rates may allow cells to spread closer to the membrane, leading to increased mean size of cells retained (not passing through the membrane).

EXAMPLES

A. System and Method for Processing Biological Cells and Target Cell Selection

In the following example, the reusable hardware apparatus 200 and its controller may be configured to the following settings, illustrated in FIG. 5B. FIG. 5B sets forth three possible settings for the following system and method. In one embodiment of the system and method, a first and second procedure may be performed, with each procedure comprising two cycles. The settings of apparatus 200 may be such that all cycles of the first and second procedures may comprise a spinner inlet flow rate of 150 mL/min, a reduction spinner revolution rate of 3750 rpm, a desired spinner inlet PCV of 3%, and reduction retentate pump rate of 15 mL/min. In a second embodiment of the system and method, a first and second procedure may be performed, with each procedure comprising two cycles. The settings of apparatus 200 may be such that all cycles of the first and second procedures may comprise a spinner inlet flow rate of 80 mL/min, a reduction spinner revolution rate of 4000 rpm, a desired spinner inlet PCV of 6%, and reduction retentate pump rate of 8 mL/min. In a third embodiment of the system and method, a first and second procedure may be performed, with each procedure comprising two cycles. The settings of apparatus 200 may be such that both cycles of the first procedure comprise a spinner inlet flow rate of 80 mL/min, a reduction spinner revolution rate of 4000 rpm, a desired spinner inlet PCV of 6%, and reduction retentate pump rate of 8 mL/min; and both cycles of the second procedure comprise a spinner inlet flow rate of 148 mL/min, a reduction spinner revolution rate of 2750 rpm, a desired spinner inlet PCV of 7%, and reduction retentate pump rate of 16 mL/min.

Referring to FIGS. 1 and 2, in one embodiment, apparatus 200 and circuit 100 may be used to process cell products, e.g., leukapheresis products, in preparation for selection of surface antigen expressing WBCs, e.g., T-cells. A selection system may be used to select specific white blood cells (WBCs), e.g., T-cells. Examples of cell selection systems include fluorescent labeling systems, although any suitable cell selection system may be used.

Figure 5A:
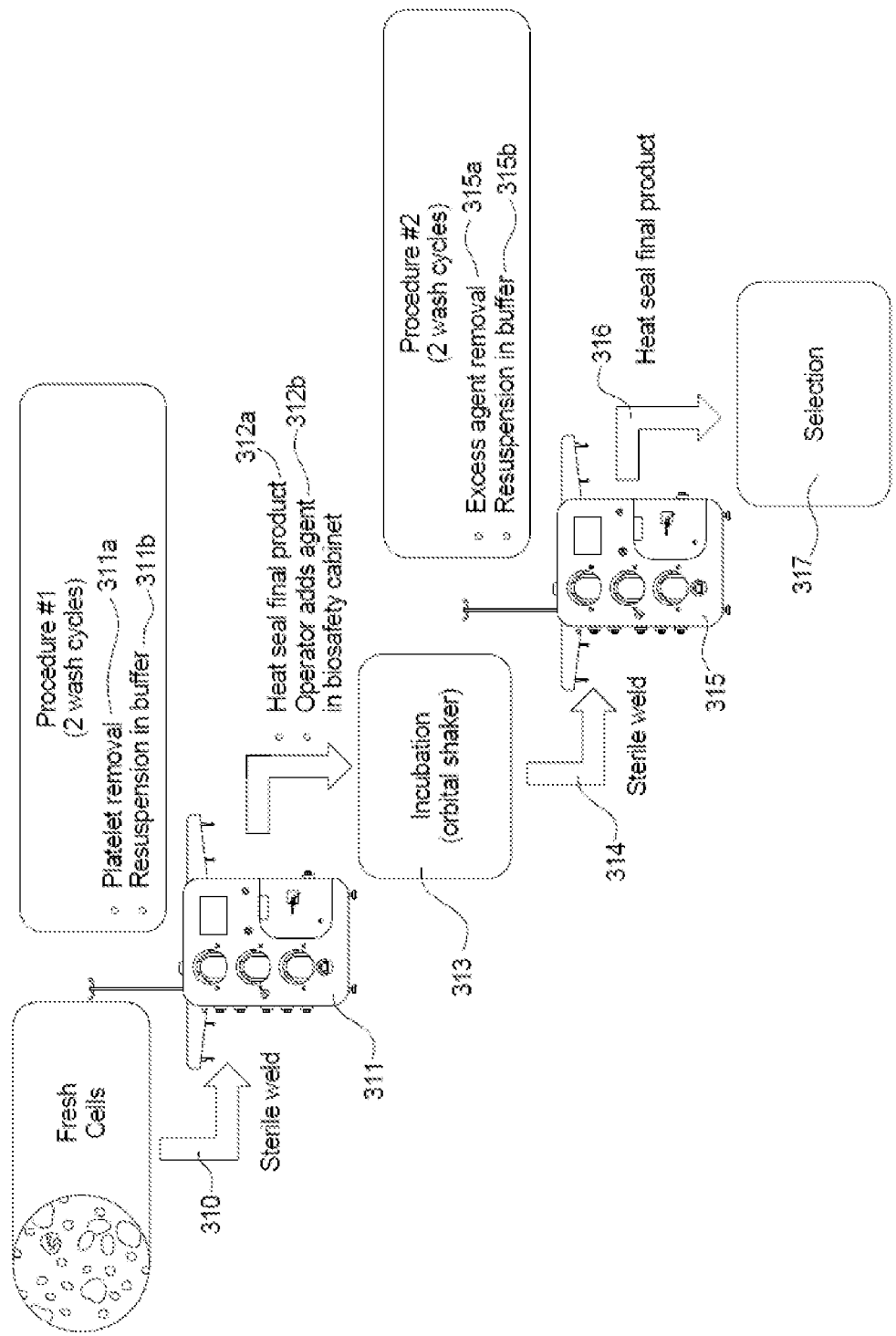
FIG. 5A is a flow diagram illustrating the steps in processing biological cells and performing target cell selection, according to an exemplary embodiment.

Turning to FIG. 5A, a flow diagram is shown, illustrating the steps in processing biological cells and performing target cell selection, according to an exemplary embodiment. At step 310, a sterile circuit 100 may be mounted onto the apparatus 200 (FIG. 1). Source container 102 holding fresh leukapheresis product or any other cell product (e.g., overnight refrigerated, recently obtained via apheresis, etc.) may be sterile-connected to docking site 104 connected to tubing 106. The cell product may comprise leukocytes, e.g., WBCs, T-cells, suspended in a cell additive solution. Also included within the cell product may be platelets and red blood cells suspended alongside the cells. After apparatus 200 determines that the disposable set 100 is properly installed, the controller may prompt the operator to connect a wash medium. Wash container 135a holding the wash medium may be accessed by spike connector 134a of the circuit 100 or sterile welded. The wash medium may comprise a buffer comprising PBS, EDTA, HSA, and/or saline, although any suitable wash medium may be used.

After the source of biological fluid and wash media have been connected to the disposable set, the fluid circuit 100 may commence a first procedure at step 311 comprising supernatant removal and resuspension. The fluid circuit 100 may first be primed for the wash process. The circuit 100 may be primed with the wash medium in container 135a or be primed with saline or any other bio-compatible aqueous solution in container 135b. The controller of apparatus 200 may then commence a first cycle comprising a wash. At step 311a, the cell product in container 102 to be washed may be transferred from source container 102 to the spinning membrane separator 101 via the operation of one or more peristaltic pumps 202, 204 and 206. At approximately the same time, the wash medium in container 135a may be delivered through the circuit 100 to the separator 101. The separator 101 may separate the cell product into target cells, e.g., target leukocytes, and remaining supernatant. The membrane of the separator 101 may be made of a thin (approximately 10-50 micron thick) sheet of, for example, polycarbonate, and have pore sizes of approximately 4 microns, or a suitable pore size allowing platelets to pass through but not target cells, e.g., target leukocytes. The target cells may exit the separator 101 through outlet orifice 48 and be directed to the in-process container 122, while the supernatant and formed elements, e.g., platelets, may exit the separator 101 through outlet orifice 46 and be directed to the waste/filtrate bag 140. The supernatant collected in waste/filtrate bag 140 may comprise the cell additive solution and platelets. Wash medium, e.g., buffer comprising PBS, EDTA, HSA, and/or saline, contained in wash container 135a, may then be pumped through the separator 101 to recover any target cells and/or supernatant remaining in the circuit 100 and respectively direct them to the in-process container 122 and/or waste/filtrate bag 140. The contents of the in-process container 122 may comprise concentrated target cells, e.g., target WBCs, suspended in wash media and red blood cells. In one embodiment, an operator may manually mix the target cells suspended in wash media in the in-process container 122 by holding container 122 with both hands and mixing thoroughly by using a gentle rotating motion, although any suitable mixing method may be used.

At step 311b of FIG. 5A, a second cycle of the first procedure may commence, wherein the contents of the in-process container 122 may be diluted further with wash medium in container 135a or 135b in preparation for another pass through the separator 101. The diluted target cells suspended in wash media in container 122 to be washed and concentrated may be transferred from source container 122 to the spinning membrane separator 101 via the operation of one or more peristaltic pumps 202, 204 and 206. The separator 101 may separate the diluted target cells suspended in wash media into target cells and remaining supernatant. The target cells may exit the separator 101 through outlet orifice 48 and be directed to the product/retentate container 150, while the supernatant may exit the separator 101 through outlet orifice 46 and be directed to the waste/filtrate bag 140. The supernatant collected in waste/filtrate bag 140 may comprise cell additive solution, wash media, platelets, and red blood cells. Wash media, e.g., buffer comprising PBS, EDTA, HSA, and/or saline, contained in wash container 135a or 135b, may then be pumped through the separator 101 to rinse any target cells and/or supernatant remaining in the circuit 100 and respectively direct them to the product/retentate container 150 and/or waste/filtrate bag 140. The contents of the product/retentate container 150 may comprise concentrated target cells suspended in wash media.

After completion of the first procedure, the product/retentate container 150 may be disconnected at step 312a of FIG. 5A from the remainder of the circuit 100 in a sterile manner, e.g., heat-seal. At step 312b, an operator may inject an agent into the product/retentate container 150 within an enclosed, ventilated laboratory workspace, such as a biosafety cabinet. The agent may have a diameter (largest cross-sectional length) of approximately 50 nm, or any suitable diameter smaller than the pore size of the membrane of the separator 101. At step 313, the agent may be incubated with the target cells within the product/retentate container 150 for a suitable period of time, e.g., thirty minutes, on an orbital shaker at a suitable temperature, e.g., room temperature.

A fresh disposable circuit or the previously used circuit 100 at step 310 may be mounted onto the apparatus 200 (FIG. 1). The product/retentate container 150 containing the product comprising target cells incubated with the agent may now serve as source container 102'. At step 314 of FIG. 5A, source container 102' may be sterile-connected to docking site 104 connected to tubing 106. The incubated target cell product may comprise leukocytes, e.g., T-cells bound and/or associated with an agent, T-cells not bound and/or associated with an agent, agent not bound to any cells, and wash media. After apparatus 200 determines that the disposable set 100 is properly installed, the controller may prompt the operator to connect a wash medium. Wash container 135a or 135b holding the wash medium may be accessed by spike connector 134a or 134b of the circuit 100. The wash medium may comprise a buffer comprising PBS, EDTA, HSA, and/or saline, although any suitable wash medium may be used.

After the source container 102' and wash media have been connected to the disposable set, the fluid circuit 100 may commence a second procedure at step 315 comprising excess agent removal and resuspension. The fluid circuit 100 may be primed for the wash process. The circuit 100 may be primed with the wash medium in container 135a or 135b. The controller of apparatus 200 may then commence a first cycle comprising a wash. At step 315a, the incubated target cell product in container 102' to be washed may be transferred from source container 102' to the spinning membrane separator 101 via the operation of one or more peristaltic pumps 202, 204 and 206. At approximately the same time, the wash medium in container 135a or 135b may be delivered through the circuit 100 to the separator 101. The separator 101 may separate the incubated target cell product into incubated target cells and remaining supernatant. The membrane of the separator 101 may have pores having sizes greater than the diameter of unbound agent and any remaining platelets but less than the diameter of certain cellular components. In one embodiment in which the cellular components have a diameter of approximately 10 microns, the agent has a diameter of approximately 50 nm, and platelets have a diameter of approximately 3 microns, the pores should have sizes greater than 3 microns and less than 10 microns, thereby allowing unbound agent and any remaining platelets to pass through, while not allowing the target cellular components and target cellular components bound to the agent to pass through. The incubated target cells may exit the separator 101 through outlet orifice 48 and be directed to the in-process container 122, while the supernatant may exit the separator 101 through outlet orifice 46 and be directed to the waste/filtrate bag 140. The supernatant collected in waste/filtrate bag 140 may comprise wash media, any remaining platelets, and unbound agent. Additional wash media, e.g., buffer comprising PBS, EDTA, HSA, and/or saline, contained in wash container 135a or 135b, may then be pumped through the separator 101 to recover any incubated target cells and/or supernatant remaining in the circuit 100 and respectively direct them to the in-process container 122 and/or waste/filtrate bag 140. The contents of the in-process container 122 containing incubated target cells may comprise, e.g., T-cells bound to agent, T-cells not bound to agent, red blood cells, and wash media. In one embodiment, an operator may manually mix the incubated target cells suspended in wash media in the in-process container 122 by holding container 122 with both hands and mixing thoroughly by using a gentle rotating motion, although any suitable mixing method may be used.

At step 315b of FIG. 5A, a second cycle of the second procedure may commence, wherein the contents of the in-process container 122 may be resuspended with wash medium in container 135a or 135b in preparation for another pass through the separator 101. The incubated target cells resuspended in wash media in container 122 may be transferred from source container 122 to the spinning membrane separator 101 via the operation of one or more peristaltic pumps 202, 204 and 206. The separator 101 may separate the incubated target cells suspended in wash media into incubated target cells and remaining supernatant. The incubated target cells may exit the separator 101 through outlet orifice 48 and be directed to a fresh product/retentate container 150', while the supernatant may exit the separator 101 through outlet orifice 46 and be directed to the waste/filtrate bag 140. The supernatant collected in waste/filtrate bag 140 may comprise wash media, any remaining platelets, and unbound agent. Wash media, e.g., buffer comprising PBS, EDTA, HSA, and/or saline, contained in wash container 135a or 135b, may then be pumped through the separator 101 to rinse any incubated target cells and/or supernatant remaining in the circuit 100 and respectively direct them to the product/retentate container 150' and/or waste/filtrate bag 140. The contents of the product/retentate container 150' may comprise T-cells bound to agent and T-cells not bound to agent suspended in wash media.

After completion of the second procedure, the product/retentate container 150' may be disconnected at step 316 of FIG. 5A from the remainder of the circuit 100 and from the apparatus 200 in a sterile manner, e.g., heat-seal. At step 317, an operator may subject the incubated target cells within container 150' to a cell selection system to separate, e.g., the T-cells bound to the agent from the T-cells not bound to the agent. The unbound T-cells and the agent bound to the T-cells may be subject to a selection process, wherein only the agent bound to the T-cells may be retained, while the unbound/unassociated T-cells may pass through the selection process, thereby effecting separation of the desired T-cells and the undesired T-cells.

B. Abbreviated System and Method for Processing Biological Cells and Target Cell Selection In the following example, the reusable hardware apparatus 200 and its controller may be configured to the following settings, illustrated in FIG. 6B. FIG. 6B sets forth settings for the following system and method. In one embodiment of the system and method, a single procedure may be performed, the single procedure comprising three cycles. The settings of apparatus 200 may be such that the first two cycles comprise a spinner inlet flow rate of 80 mL/min, a reduction spinner revolution rate of 4000 rpm, a desired spinner inlet PCV of 6%, and reduction retentate pump rate of 8 mL/min. The third cycle may be set to a spinner inlet flow rate of 148 mL/min, a reduction spinner revolution rate of 2750 rpm, a desired spinner inlet PCV of 7%, and reduction retentate pump rate of 16 mL/min.

Referring to FIGS. 1 and 2, in one embodiment, apparatus 200 and circuit 100 may be used to process cell products, e.g., leukapheresis products, in preparation for selection of desired WBCs, e.g., surface antigen expressing T-cells.

Figure 6A:
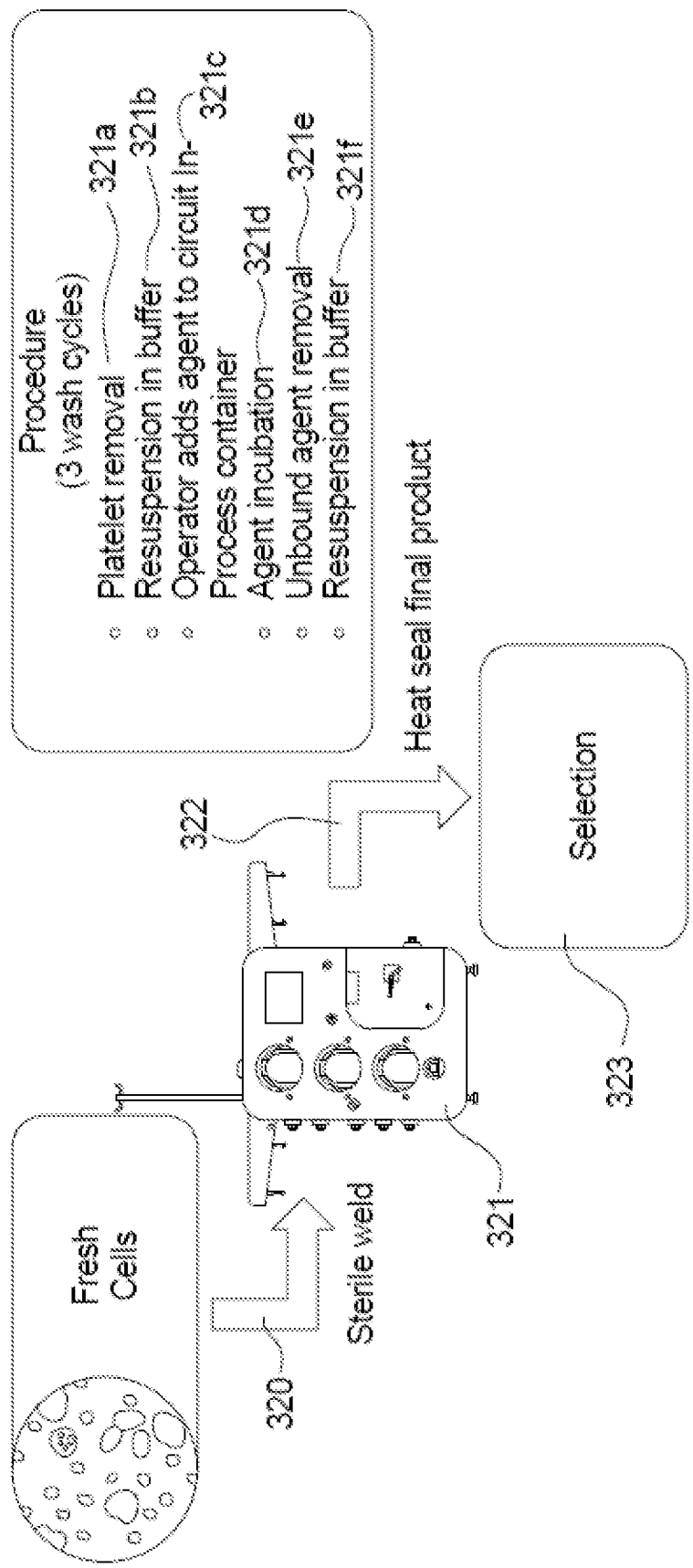
FIG. 6A is a flow diagram illustrating the steps in processing biological cells and performing target cell selection, according to an exemplary embodiment.

Turning to FIG. 6A, a flow diagram is shown, illustrating the steps in processing biological cells and performing target cell selection, according to an exemplary embodiment. At step 320, a sterile circuit 100 may be mounted onto the apparatus 200 (FIG. 1). Source container 102 holding fresh cell product, such as a leukapheresis product (e.g., overnight refrigerated, recently obtained via apheresis, etc.), may be sterile-connected to docking site 104 connected to tubing 106. The cell product may comprise leukocytes, e.g., desired T-cells, suspended in a cell additive solution. Also included within the cell product may be platelets suspended alongside the cells. After apparatus 200 determines that the disposable set 100 is properly installed, the controller may prompt the operator to connect a wash medium. Wash container 135a holding the wash medium may be accessed by spike connector 134a of the circuit 100. The wash medium may comprise a buffer comprising PBS, EDTA, HSA, and/or saline, although any suitable wash medium may be used.

After the source of biological fluid and wash media have been connected to the disposable set, the fluid circuit 100 may commence the procedure at step 321 comprising platelet removal, resuspension in wash media, agent incubation, excess agent removal, and resuspension in wash media. The fluid circuit 100 may first be primed for the wash process. The circuit 100 may be primed with the wash medium in container 135a or be primed with saline or any other bio-compatible aqueous solution in container 135b. The controller of apparatus 200 may then commence a first cycle comprising a wash. At step 321a, the cell product in container 102 to be washed may be transferred from source container 102 to the spinning membrane separator 101 via the operation of one or more peristaltic pumps 202, 204 and 206. At approximately the same time, the wash medium in container 135a may be delivered through the circuit 100 to the separator 101. The separator 101 may separate the cell product into target cells and remaining supernatant. As stated in Example A, the membrane of the separator 101 may comprise pores having sizes allowing platelets to pass through but not certain cellular components. The target cells may exit the separator 101 through outlet orifice 48 and be directed to the in-process container 122, while the supernatant and formed elements, e.g., platelets, may exit the separator 101 through outlet orifice 46 and be directed to the waste/filtrate bag 140. The supernatant collected in waste/filtrate bag 140 may comprise the cell additive solution and platelets. Wash medium, e.g., buffer comprising PBS, EDTA, HSA, and/or saline, contained in wash container 135a, may then be pumped through the separator 101 to recover any target cells and/or supernatant remaining in the circuit 100 and respectively direct them to the in-process container 122 and/or waste/filtrate bag 140. The contents of the in-process container 122 may comprise concentrated target cells suspended in wash media. In one embodiment, an operator may manually mix the target cells suspended in wash media in the in-process container 122 by holding container 122 with both hands and mixing thoroughly by using a gentle rotating motion, although any suitable mixing method may be used.

At step 321b of FIG. 6A, a second cycle of the procedure may commence, wherein the contents of the in-process container 122 may be diluted further with wash medium in container 135a or 135b in preparation for another pass through the separator 101. The diluted target cells suspended in wash media in container 122 to be washed and concentrated may be transferred from source container 122 to the spinning membrane separator 101 via the operation of one or more peristaltic pumps 202, 204 and 206. The separator 101 may separate the diluted target cells suspended in wash media into target cells and remaining supernatant. The target cells may exit the separator 101 through outlet orifice 48 and be directed again to the in-process container 122, while the supernatant may exit the separator 101 through outlet orifice 46 and be again be directed to the waste/filtrate bag 140. The supernatant collected in waste/filtrate bag 140 may comprise cell additive solution, wash media, and platelets. Wash media, e.g., buffer comprising PBS, EDTA, HSA, and/or saline, contained in wash container 135a or 135b, may then be pumped through the separator 101 to rinse any target cells and/or supernatant remaining in the circuit 100 and respectively direct them to the in-process container 122 and/or waste/filtrate bag 140. The contents of the in-process container 122 may comprise concentrated target cells suspended in wash media.

At step 321c, the reusable hardware apparatus 200 and its controller may be configured to pause automatically after the second cycle at 321b. The pause may allow an operator to inject an incubation agent into the in-process container 122. The incubation agent may be housed in an introducer container 122b (FIG. 2) and sterile-connected to a port 122a of container 122. The introducer container may be pre-attached to the disposable circuit 100 prior to a procedure or may be attached in a sterile manner to container 122 during a procedure. After injection of the incubation agent into container 122, an operator may manually mix the target cells and incubation agent suspended in wash media in the in-process container 122 by holding container 122 with both hands and mixing thoroughly by using a gentle rotating motion, although any suitable mixing method may be used.

At step 321d, the agent/target cell conjugated complex, e.g., antibody-conjugated agent, may be incubated during an incubation cycle with the target cells within the in-process container 122 for a suitable period of time, e.g., thirty minutes, at a suitable temperature, e.g., room temperature. In one embodiment, the target cell/agent mixture may be incubated stilly with minimal shaking and/or agitation. In another embodiment, an operator may manually mix the target cell/agent mixture with both hands off the apparatus 200. In another embodiment, apparatus 200 and its controller may allow for an automated incubation cycle comprising gentle mixing achieved by cycling the target cell/agent mixture from the in-process container 122 through tubing 120 to the inlet port 20 of the spinner 101. From spinner 101, the target cell/agent mixture may exit the spinner 101 through outlet port 48, through tubing 168, and back into the in-process container 122. The target cell/agent mixture may be restricted to this cyclical pathway by clamping tubing 138 leading from the outlet port 46 of spinner 101 and also by clamping the flow path leading from branch connector 144 to the product/retentate container 150. During the automated incubation cycle, the flow rate along the cyclical pathway may be set at a suitable rate, according to the specific selection system. The revolution rate of the spinner 101 during the automated incubation cycle may likewise be set at a suitable rate, e.g., 500-700 rpm, appropriate for a particular selection system. During the automated incubation cycle, incubation volume and/or concentration within the product/retentate container 150 may be increased by pumping additional solution(s) and/or agent at a configurable rate into the cycle via e.g., container 135*a* and/or 135*b*. Multiple incubation cycles may be implemented with the inclusion of additional pauses and additional sterile connections with the in-process container 122.

Upon completion of the incubation, step 321*e* comprising a third cycle for unbound agent removal may commence. Wash media within container 135*a* or 135*b* may be delivered through the circuit 100 through the separator 101 into in-process container 122 to dilute the incubated target cells resulting from the incubation. An operator may manually mix the diluted incubated target cells in the in-process container 122 by holding container 122 with both hands and mixing thoroughly by using a gentle rotating motion, although any suitable mixing method may be used. The contents of container 122 comprising incubated target cells may then enter the separator 101, which may separate the incubated target cell product into incubated target cells and remaining supernatant. The membrane of the separator 101 may have pores having sizes greater than the diameter of unbound agent and any remaining platelets but less than the diameter of certain cellular components, thereby allowing unbound agent and any remaining platelets to pass through, while not allowing the target cellular components and target cellular components bound to the agent to pass through. The incubated target cells may exit the separator 101 through outlet orifice 48 and be directed to the product/retentate container 150, while the supernatant may exit the separator 101 through outlet orifice 46 and be directed to the waste/filtrate bag 140. The supernatant collected in waste/filtrate bag 140 may comprise wash media, any remaining platelets, and unbound agent. At step 321*f,* additional wash media, e.g., buffer comprising PBS, EDTA, HSA, and/or saline, contained in wash container 135*a* or 135*b*, may then be pumped through the separator 101 to recover any incubated target cells and/or supernatant remaining in the circuit 100 and respectively direct them to the product/retentate container 150 and/or waste/filtrate bag 140. The contents of the product/retentate container 150 containing incubated target cells may comprise, e.g., desired T-cells bound to the agent, and e.g., undesired T-cells not bound to the agent, suspended in wash media.

After completion of the third cycle, the product/retentate container 150 may be disconnected at step 322 of FIG. 6A from the remainder of the circuit 100 and from the apparatus 200 in a sterile manner, e.g., heat-seal. At step 323, an operator may subject the incubated target cells, e.g., target leukocytes, within container 150 to a cell selection system to separate the target surface antigen expressing WBCs bound to the agent from the cells not presenting the target antigen, i.e., not bound to the agent, as described in Example A.

In addition to the foregoing, a further embodiment of a cell processing system that may incorporate a magnet with the cell processing system as described above relative to FIGS. 1-4 is now described relative to FIGS. 7-10. Because many of the details of the cell processing system 100, 200 have been described in detail above, the discussion relative to the system 100, 200 made with reference to FIGS. 1-4 will not be repeated herein. Instead, like numbers will be used for like elements, and the focus will be on the additional details or elements (e.g., magnet 600 in FIG. 7) discussed with reference to the embodiment of FIGS. 7-10.

Figure 7:
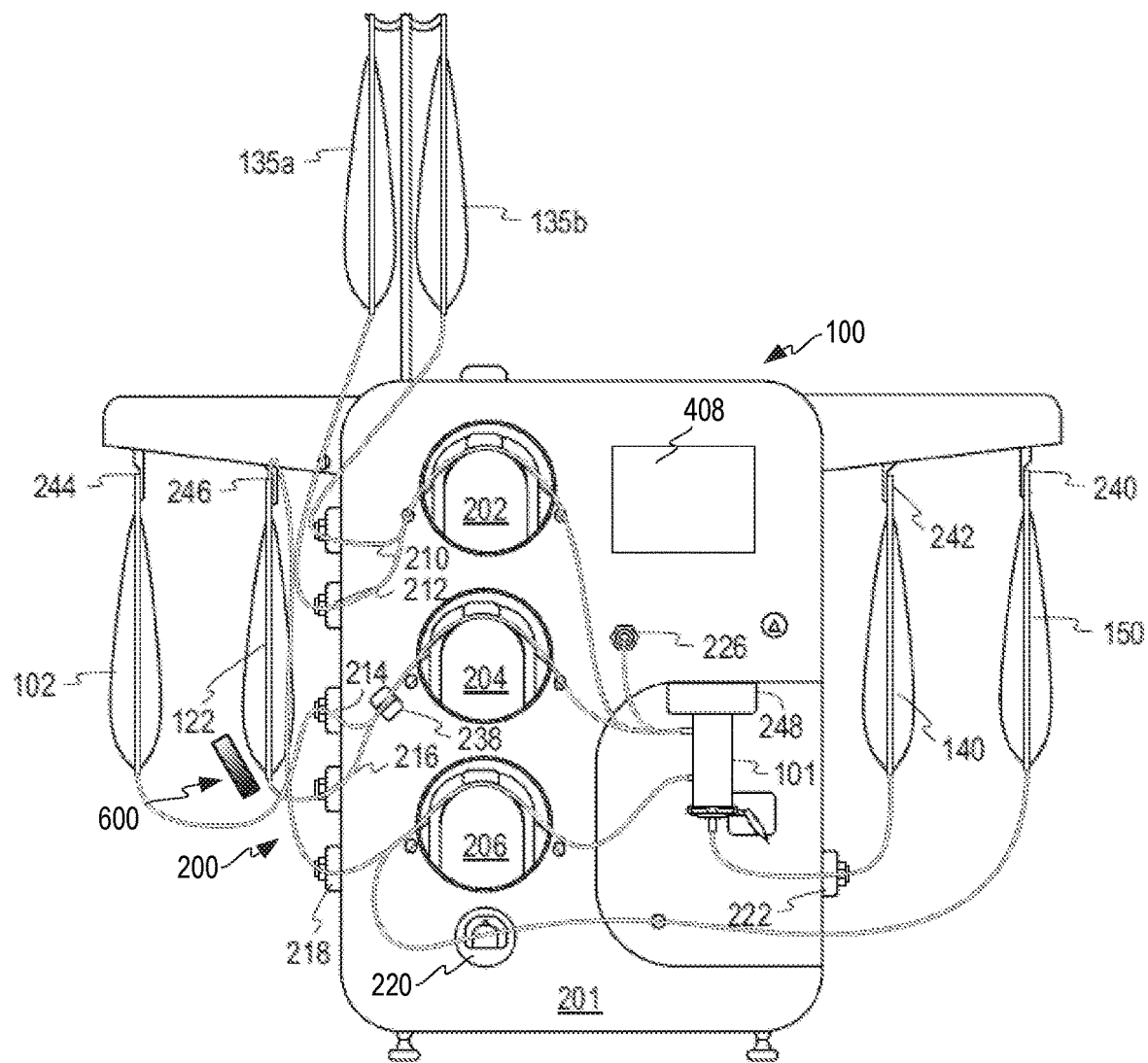
FIG. 7 is a frontal view of a reusable cell processing system with a disposable fluid circuit loaded thereon.
Figure 8:
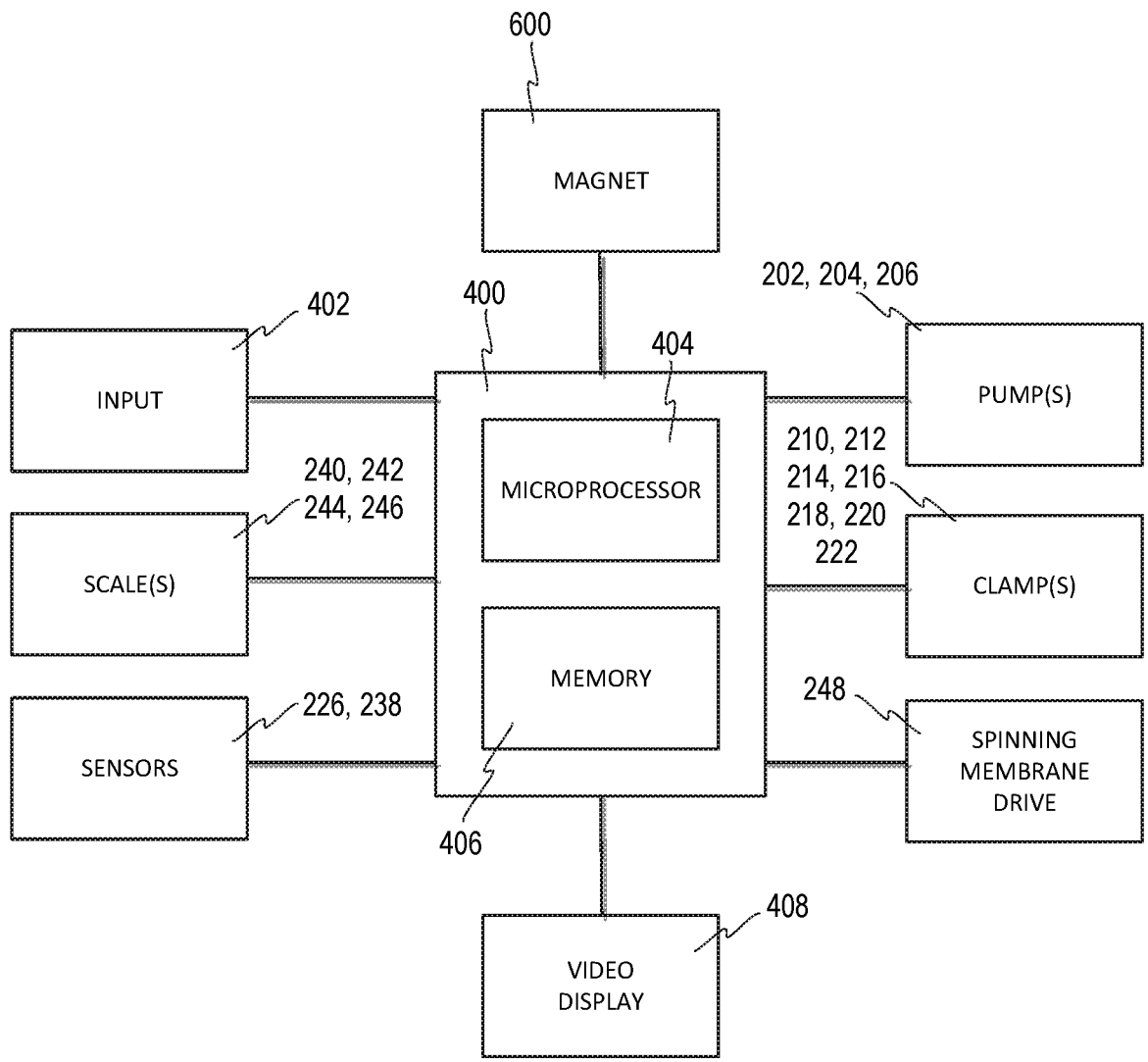
FIG. 8 is a schematic view of the control circuitry of the apparatus of FIG. 7.

As illustrated in FIGS. 7 and 8, a cell processing system includes a processor 100, 200 to receive a biological fluid to be processed, and a control unit (or controller) 400 coupled to the processor 100, 200. The controller 400 is configured to operate the processor 100, 200 according to a procedure or process to produce or generate a product that may be disposed in a product container. The controller 400 may include a microprocessor 404 (which, in fact may include multiple physical and/or virtual processors). According to other embodiments, the controller 400 may include one or more electrical circuits designed to carry out the actions described herein. In fact, the controller 400 may include a microprocessor and other circuits or circuitry. In addition, the controller 400 may include one or more memories 406. The instructions by which the microprocessor 404 is programmed may be stored on the memory 406 associated with the microprocessor 404, which memory/memories 406 may include one or more tangible non-transitory computer readable memories, having computer executable instructions stored thereon, which when executed by the microprocessor 404, may cause the microprocessors 404 to carry out one or more actions as described below.

As is also illustrated in FIG. 8, the controller 400 may be coupled to one or more of the structures described above, for example to receive information (e.g., in the form of signals) from these structures or to provide commands (e.g., in the form of signals) to these structures to control the operation of the structures. As illustrated, the controller 400 may be coupled to the scales 240, 242, 244, 246, the sensors 226, 238 and at least one input 402 to receive information from those devices. Additionally, the controller 400 may be coupled to the pumps 202, 204, 206, the clamps 210, 212, 214, 216, 218, 220, 222, and the drive 248 to provide commands to those devices to control their operation. As also mentioned above, the controller 400 may be coupled to a magnet 600 (see FIGS. 7 and 8). It may also be possible that the controller 400 receives information from and provides commands to a given structure, such as one of the structures already mentioned. The controller 400 may be directly electrically connected to these structures to be coupled to them, or the controller 400 may be directly connected to other intermediate equipment that is directly connected to these structures to be coupled to them.

The at least one input 402 may include a number of different devices according to the embodiments described herein. For example, the input 402 could include a keyboard or keypad by which a user may provide information and/or instructions to the controller 400. Alternatively, the input 402 may be a touch screen, such as may be used in conjunction with a video display 408 that is disposed on the front panel 201 of the device 200 (see FIG. 7), the video display 408 also being coupled to the controller 400 (see FIG. 8). The input 402 could also include a reader or scanner, such as a barcode reader or scanner or an RFID reader. The assembly of the input/touch screen 402 and video display 408 may be one of the afore-mentioned structures to which the controller 400 is coupled from which the controller 400 receives information and to which the controller 400 provides commands. According to still other embodiments, the input 402 may be in the form of computer equipment that permits the cell processing system including the controller 400 to communicate (whether via wires, cables, etc. or wirelessly) with other cell processing systems over a local network, or with other cell processing systems or other computer equipment (e.g., a server) over local networks, wide area networks, or the Internet. According to such an embodiment, the input may include an internal transmitter/receiver device.

According to the embodiment of FIGS. 7-10, the cell processing system may be used in conjunction with a magnet 600, as illustrated generally in FIG. 7. In particular, the magnet 600 is disposed proximate to the in-process container 122.

The operation of the cell processing system illustrated is now discussed. In general terms, the operator may first activate (e.g., switch on) apparatus 200, at which point the apparatus 200 conducts self-calibration checks, including the checking of the peristaltic pumps 202, 204, 206, clamps 210, 212, 214, 216, 218, 220, 222, and sensors 226, 238. Apparatus 200 may then prompt the user to enter or modify process parameters using the input 402, including by way of example and not by way of limitation the amount of cell suspension to be processed, the number of cycles to take place, etc. The apparatus 200 may then prompt the operator to mount the disposable set 100, after which apparatus 200 automatically checks to determine whether the disposable set 100 is properly installed. Once the set 100 is properly installed, the controller 400 prompts the operator to connect the biological fluid (e.g., 102 of FIG. 7) via a spike connector or sterile connection (e.g., 103, 104 of FIG. 2) and the wash medium (e.g., 135a, 135b of FIG. 7) via a spike connector (e.g., 134a, 134b of FIG. 2) or sterile welding. In one embodiment, the biological fluid/cells may be apheresis-collected leukocytes, and the wash medium may be a saline solution or a buffer.

Once the operator confirms that the solutions are connected, the controller 400 primes the disposable set 100. In the embodiment discussed above, the set 100 may be primed with saline, although other biocompatible aqueous solutions may also be used. The controller 400 then commences processing the biological fluid/cells, which may have been recently obtained via apheresis (or leukapheresis), refrigerated overnight, etc. The biological fluid/cells is/are transferred from source container (e.g., 102 of FIG. 7) through the set to the spinning membrane separator 101 via the operation of one or more peristaltic pumps 202, 204 and 206. In a similar fashion, the wash medium may be delivered from its container (e.g., 135a, 135b of FIG. 7) through the set to the spinning membrane separator 101. The biological cells are collected in the in-process container (e.g., 122 of FIG. 7), while supernatant is separated and removed to filtrate container (e.g., 140 of FIG. 7). In regard to this portion of the method, the disclosure of the embodiments above incorporated by reference herein in its entirety, and in particular as to the settings for the apparatus described in the disclosure and figures thereof.

According to the present disclosure, a conjugated antibody magnetic bead, such as DYNABEADS magnetic beads available from ThermoFisher Scientific of Waltham, MA, may be introduced to the solution in the in-process container 122, and incubated for a period of time to allow for interaction between the conjugated antibody beads in the solution and the target cells (which may be white blood cells of a particular phenotype, such as CD34+ peripheral blood stem cells and CD3+/CD4+/CD28+ T-cell lymphocytes, which cells may also be referred to as target cells). Once the conjugated antibody beads are associated with the target cells (e.g., the target cells are bound to the antibodies that are part of the conjugated antibody beads to form conjugated antibody bead-target cell complexes), various actions may be taken.

For example, a filter may be used to separate the conjugated antibody bead-target cell complexes. According to certain embodiments, the complexes can be directed to the retentate container, at which point the beads may be decoupled from the target cells. The decoupling is optional, because the conjugated antibody beads may function as an activator for the target cell (i.e., may encourage the growth of the target cell population) and thus it may be preferred to leave the conjugated antibody bead bound to the target cells (for example, for purposes of target cell (e.g., t-cell) expansion).

As a further alternative, the conjugated antibody bead-target cell complexes may not be filtered, but a magnet, such as the magnet 600, may be used to separate the conjugated antibody bead-target cell complexes from the remainder of cells. With the magnet 600 applied and/or activated (where the magnet is in the form of an electromagnet), the contents of the bag are sent to the separator 101 to remove the materials other than the conjugated antibody bead-target cell complexes. The magnet 600 may then be removed and/or deactivated to permit collection of the target cell complexes. Here as well, the conjugated antibody bead may be decoupled from the target cells, or the complex may be used to encourage growth of the target cell population.

Figure 9:
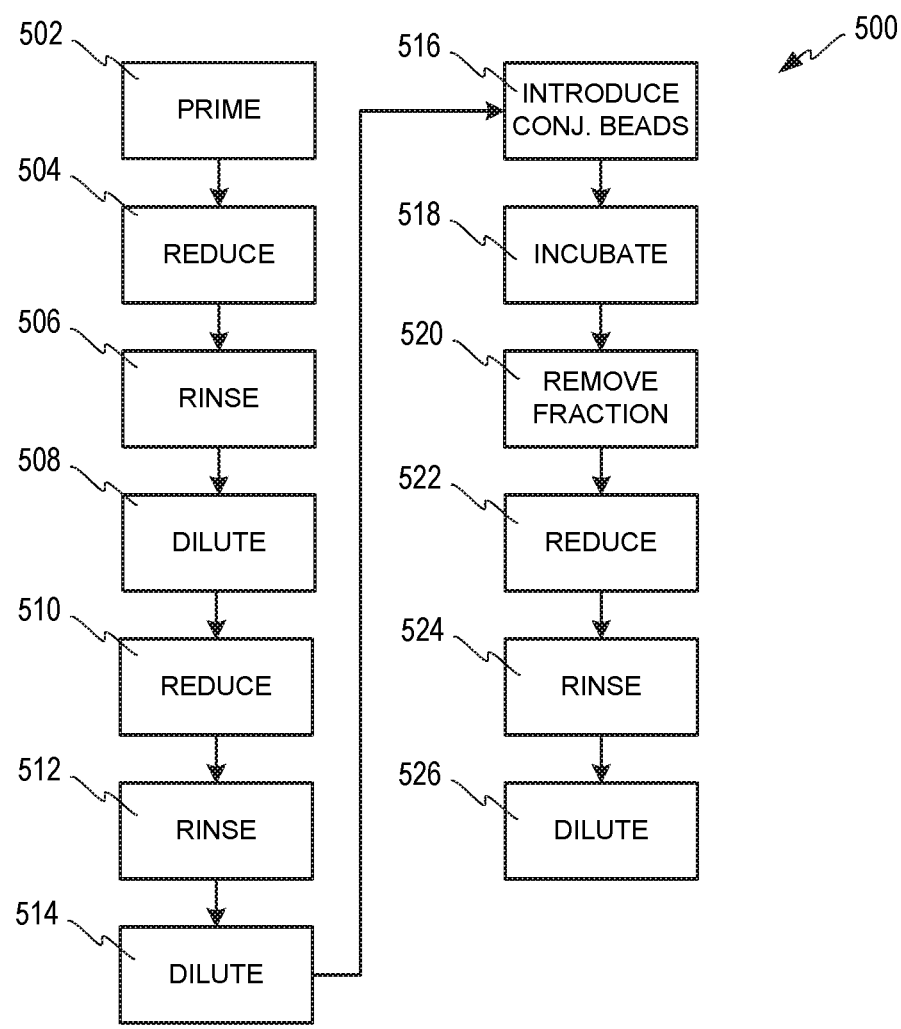
FIG. 9 is a flowchart of an embodiment of a method of operating a reusable cell processing apparatus with a disposable fluid circuit loaded thereon, such as is illustrated in FIG. 7, to process a biological fluid.
Figure 10:
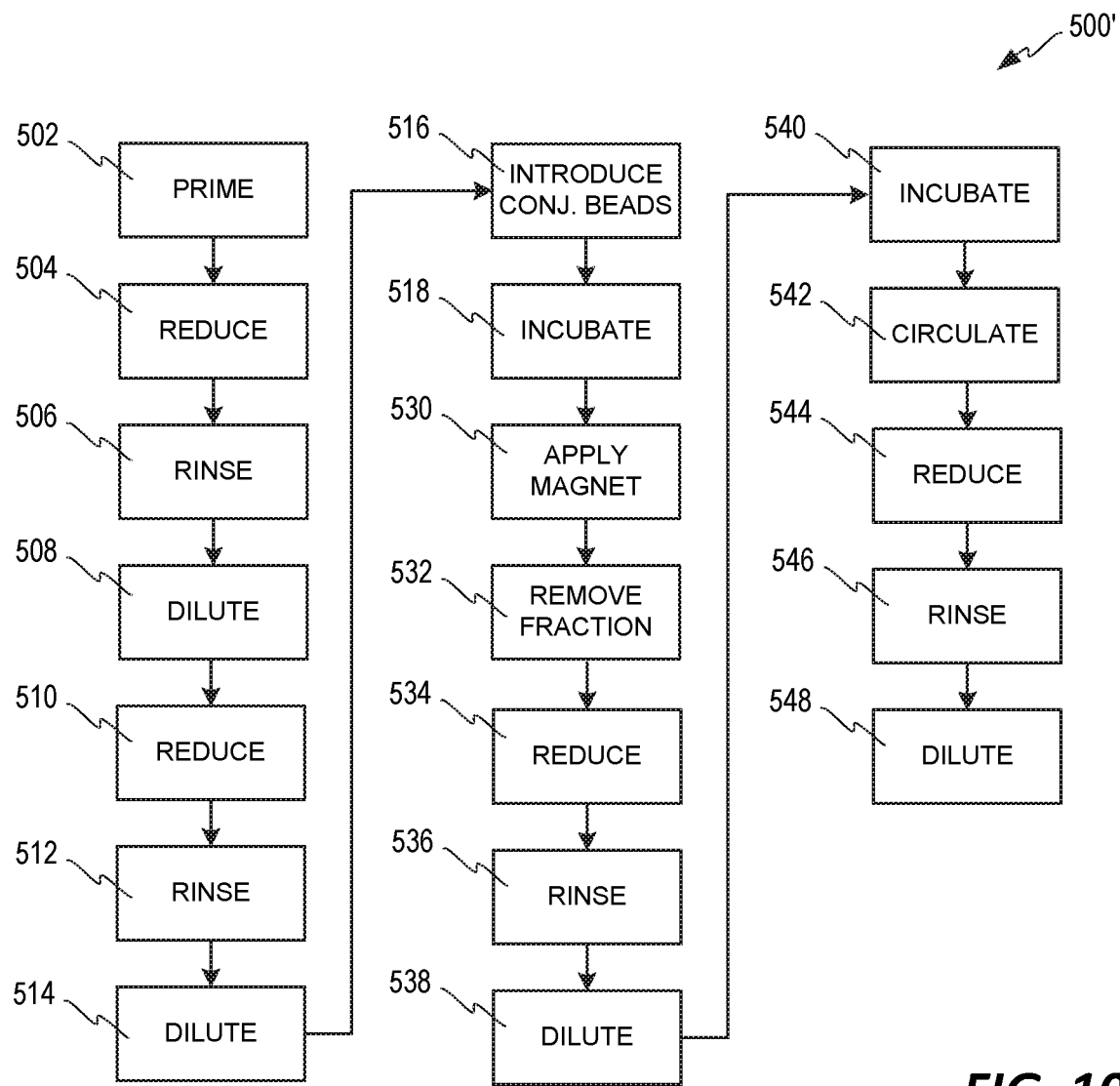
FIG. 10 is a flowchart of another embodiment of a method of operating a reusable cell processing apparatus with a disposable fluid circuit loaded thereon, such as is illustrated in FIG. 7, to process a biological fluid.

Specific embodiments of a method 500, 500' of operating the processor 100, 200 for purposes of size discrimination and/or magnetic separation of conjugated antibody bead-target cell complexes (optionally with population growth encouraged by the complexes formed) are provided in FIGS. 9 and 10. The methods 500, 500' involve certain common actions, which actions are described in relation to blocks 502-518. As a consequence, common reference numerals are used in the methods 500, 500' for these blocks, and the discussion of the actions that occur during this portion of the methods 500, 500' will be discussed relative to method 500 only. This discussion will not be repeated relative to method 500', but instead incorporated by reference therein.

Referring first then to FIG. 9, the controller 400 may cause the apparatus 200 to perform the step of priming at block 502. According to this step, wash media from one or both of the wash media containers 135a, 135b is transferred to the disposable set 100. In fact, a small amount of wash media may be transferred to each of the containers 102, 122, 140, 150 to ensure that the containers 102, 122, 140, 150 are connected. To this end, the controller 400 may cause clamps 210, 212, 214, 216, 218, 220, 222 to open to permit the transfer of fluid to the containers 102, 122, 140, 150.

The method 500 continues to block 504, where the controller 400 causes the apparatus 200 to perform a reduction step. According to this step, the controller 400 causes the biological fluid from the source container 102 (and optionally wash media from the wash media container(s) 135a, 135b) to be transferred to the separator 101. For example, the controller 400 may open clamp 214 and operate pump 204 to transfer the fluids from the container 102 to the separator 101. The separator 101 (in conjunction with operation of the drive 248 by controller 400) produces two streams: a first, or retentate, stream that is directed into the in-process container 122, and a second, or filtrate, stream that is directed into the filtrate container 140. For example, the controller 400 may open clamp 218 and operate pump 206 to cause flow into the in-process container 122 (clamp 220 being closed), and may open clamp 222 to permit flow into the container 140. As a consequence, plasma and platelets are removed from the biological fluid, and white blood cells are transferred to the in-process container 122.

To facilitate the separation of the plasma and platelets from the white blood cells within the biological fluid, the membrane of the separator 101 may be a thin sheet (10-50 µm in thickness) of polycarbonate with pore sizes of approximately 4 µm, by way of example and not by way of limitation. The pore size is selected to allow platelets (which may be 2-4 µm in size) to pass through, but not the target cells. To permit the separator 101 to be used to discriminate between the conjugated antibody beads and the complexes, the pore size may be increased slightly (i.e., in excess of 4 µm), which should not have an adverse effect on the separation performed at block 504, as the white blood cells are considerably larger than the platelets (~2-4 µm) or the conjugated antibody beads (~4.5 µm).

After the step of block 504 is complete, the controller 400 causes wash media to be passed through the set 100 (i.e., the set is rinsed) and the media is added to the in-process bag 122 at block 506. This may be achieved, for example, by closing clamps 214, 222, while opening clamps 210 (and/or 212), 216, 218 and operating pumps 202, 204, 206 to draw fluid from containers 122, 135a (and/or 135b) and circulate this through the separator 101. After block 506, the method 500 proceeds to block 508, where the controller 400 may cause additional wash media to be added to the in-process bag 122, if required, along the same fluid pathways.

The actions of blocks 504-508 may be repeated as additional cycles, as may be required by the user or operator, before the method 500 continues, so as to ensure removal of the platelets, plasma, etc. As illustrated, a further (or second) cycle consisting of blocks 510, 512, 514 may be performed, with the actions of block 510 being similar to those of block 504, those of block 512 similar to those of block 506, and those of block 514 similar to those of block 508. When block 514 is complete, the method 500 may continue with block 516 to start the process of associating the conjugated antibody beads with the target cells.

At block 516, all of the clamps 210, 212, 214, 216, 218, 220, 222 are closed. According to one embodiment, the processor 100, 200 may automatically pause at this point (i.e., under the control of the controller 400), so that the operator can manually inject the conjugated antibody bead solution into the in-process container 122; for example, an introducer container may be attached to the in-process container 122 either prior to the procedure or in a sterile manner during the procedure and the conjugated antibody bead solution is injected into the in-process container 122 from the introducer container. According to other embodiments, the conjugated antibody bead solution is introduced automatically into the in-process container 122. The method 500 may then proceed to block 518, where the contents of the container 122 may be permitted to remain in the container 122 for a period of time to allow for interaction between the conjugated antibody beads and the target cells. As part of the incubation step at block 518, the clamps 216, 218 may be opened and pumps 204, 206 and drive 248 may be operated to pass the contents of container 122 through the separator 101 to mix the suspension so as to improve the interaction between the conjugated antibody beads and target cells. For example, the spinning membrane 101 may be operated at a speed of between 500-700 rpm. Transfer of fluid from one or both of the wash solution containers 135a, 135b may occur at this time to optimize the volume for incubation. According to one embodiment, the total incubation time (including time spent mixing the contents of the in-process container 122) may be thirty minutes, while the incubation temperature may be room temperature.

Continuing at block 520, the processor 100, 200 operates to transfer the conjugated antibody bead-target cell complexes to the retentate container 150, while other material, such as unbound conjugated antibody beads, are directed to the filtrate container 140. To achieve this, the clamps 216, 220, 222 are opened and pumps 204, 206 and drive 248 are operated. The clamps 210, 212 may also be opened and pump 202 operated to introduce wash solution at the same time. In the alternative, the complexes may be returned to the in-process container 122 to permit further removal of undesired materials from the complexes.

It should be mentioned that according to an exemplary embodiment of the separator 101 described above, a thin sheet (10-50 µm in thickness) of polycarbonate with pore sizes of approximately 5 µm should function sufficiently to remove the conjugated antibody beads from the target cells with associated conjugated antibody beads (e.g., with bound conjugated antibody beads). In particular, the conjugated antibody beads may have a size of approximately 4.5 µm, such that the pore size stated above should be suitable, although a larger size may be used, considering the much larger size of the target cells.

The method 500 would continue with the actions of blocks 522-526, which are very similar to those of blocks 504-508. For example, if additional removal of undesired materials is desired, the controller 400 may cause fluid from the in-process bag 122 (and optionally wash media from the wash media container(s) 135a, 135b) to be transferred to the separator 101, by opening clamp 216 and operate pump 204 to transfer the fluids from the in-process container 122 to the separator 101, for example. The separator 101 (in conjunction with operation of the drive 248 by controller 400) produces two streams: a first, or retentate, stream that is directed into the retentate container 150, and a second, or filtrate, stream that is directed into the filtrate container 140, by opening clamps 220, 222 and operating pump 206, for example. The controller 400 may also cause wash media to be passed through the set 100 (i.e., the set is rinsed) and the media is added to the container 150 at block 524. After block 524, the method 500 proceeds to block 526, where the controller 400 may cause additional wash media to be added to the container 150, if and as required.

A further embodiment of the method 500' is illustrated in FIG. 10. The method 500' includes magnetic separation with post-separation incubation to encourage growth of the target cell population. The post-separation incubation steps could have been performed with the method 500 above as well, once the complexes have been collected into the in-process bag 500 after size discrimination.

The method 500' begins in a fashion similar to method 500: the circuit 100 is primed at block 502, and the actions of blocks 504-508 (as well as optionally the actions of blocks 510-514, or even further iterations of blocks 504-508 in addition to the actions of blocks 510-514) are performed to remove an undesired cells, such as platelets. The conjugated antibody beads are introduced at block 516 to the in-process container 122, and the contents of the in-process container 122 are permitted to incubate at block 518 as the target cells become bound to the conjugated antibody beads.

Continuing at block 530, the magnet 600 is activated and/or applied to the container 122. See also FIG. 7. The magnet 600 may be a permanent magnet, in which case the magnet 600 may be moved adjacent (which may include abutting) the container 122, or vice versa, at block 530. Alternatively, the magnet 600 may be an electromagnet already disposed adjacent (which may include abutting) the container 122, in which case the magnet 600 may be activated at block 530. As a further alternative, the magnet 600 may be an electromagnet, and the magnet 600 may be moved adjacent (which may include abutting) the container 122, or vice versa, and the magnet 600 may then be activated at block 530. To simplify the discussion, we will assume an embodiment where the magnet 600 is a permanent magnet.

With the magnet 600 disposed adjacent the container 122, the method 500' proceeds to block 532, where the contents of the container 122 are passed through the separator 101 to remove the materials not held in place in the container 122 by the magnet 600. For example, the controller 400 may open clamp 216 and operate pump 204 to transfer the fluids from the container 122 to the separator 101. The separator 101 (in conjunction with operation of the drive 248 by controller 400) produces two streams: a first, or retentate, stream that is directed back into the in-process container 122, and a second, or filtrate, stream that is directed into the filtrate container 140. For example, the controller 400 may open clamp 218 and operate pump 206 to cause flow into the in-process container 122 (clamp 220 being closed), and may open clamp 222 to permit flow into the container 140.

After the removal step, the method 500' may remove the application of the magnet 600 and continue with a cycle of reduction (block 534), rinsing (block 536) and dilution (538) in preparation for post-separation growth of the target cells that were separated as a consequence of the application of the magnet 600 at block 530 to the in-process container 122 in which the complexes were disposed. The reduction at block 534 removes any unbound conjugated antibody beads and other unwanted materials, while the rinsing and dilution ensures that the desired materials have been returned to the in-process bag with a sufficient amount of media for the subsequent incubation step at block 540.

At block 540, the complexes are permitted to incubate so as to encourage the growth of the target cells that are initially part of the conjugated antibody bead-target cell complexes. In this regard, the beads are believed to encourage the growth of the target cell population. The activity of block 540 may be combined with circulation of the contents of the in-process container 122 through the spinning membrane at block 542. For example, the clamps 216, 218 may be opened and pumps 204, 206 and drive 248 may be operated to pass the contents of container 122 through the separator 101 to mix the suspension so as to encourage growth of the target cell population. For example, the spinning membrane 101 may be operated at a speed of between 500-700 rpm.

The actions of blocks 540, 542 may be followed with the activity of reduction (block 544), rinsing (block 546) and dilution (548) to prepare a final product in the container 150. Alternatively, the activities of blocks 540-548 may be repeated to encourage the growth of the population of target cells. That is, it is known relative to DYNABEADS magnetic beads that the beads act as an activation and expansion agent for T-cells, for example. By permitting additional incubation time in the in-process bag 122, along with optional agitation of the bag 122 through the use of a mechanical agitator, such as is provided as part of the WAVE or XURI systems available from GE Healthcare Bio-Sciences, Pittsburgh, PA, and the optional introduction of fresh media, the method of FIG. 10 may be used for separation and growth of the target cells. In such a process, the activities of blocks 544-548 result in the return of the target cells/target cell complexes to the in-process bag 122 until a desired time has elapsed, at which point the retentate of the reduction at block 544 is directed to the container 150, and the rinse and dilution activities at blocks 546, 548 are performed to limit target cells remaining within the remainder of the circuit and to bring the container 150 to its desired volume. As one example, the activities of blocks 540-548 may be repeated over a 24 hour period to encourage growth in the target cell population.

As mentioned above, it will be recognized that the steps of blocks 534-548 in FIG. 10 may be substituted for those of blocks 522-526 in FIG. 9 if incubation and growth of the target cells in the in-process bag 122 is desired after the size based discrimination of FIG. 9.

Further, additional embodiments of a cell processing system that incorporates a magnet with the cell processing system as described above relative to FIGS. 1-4 is now described relative to FIGS. 11-32. Again, because many of the details of the cell processing system 100, 200 have been described in detail above, the discussion relative to the system 100, 200 made with reference to FIGS. 1-4 will not be repeated herein. Instead, like numbers will be used for like elements, and the focus will be on the additional details or elements discussed with reference to the embodiment of FIGS. 11-32.

Figure 11:
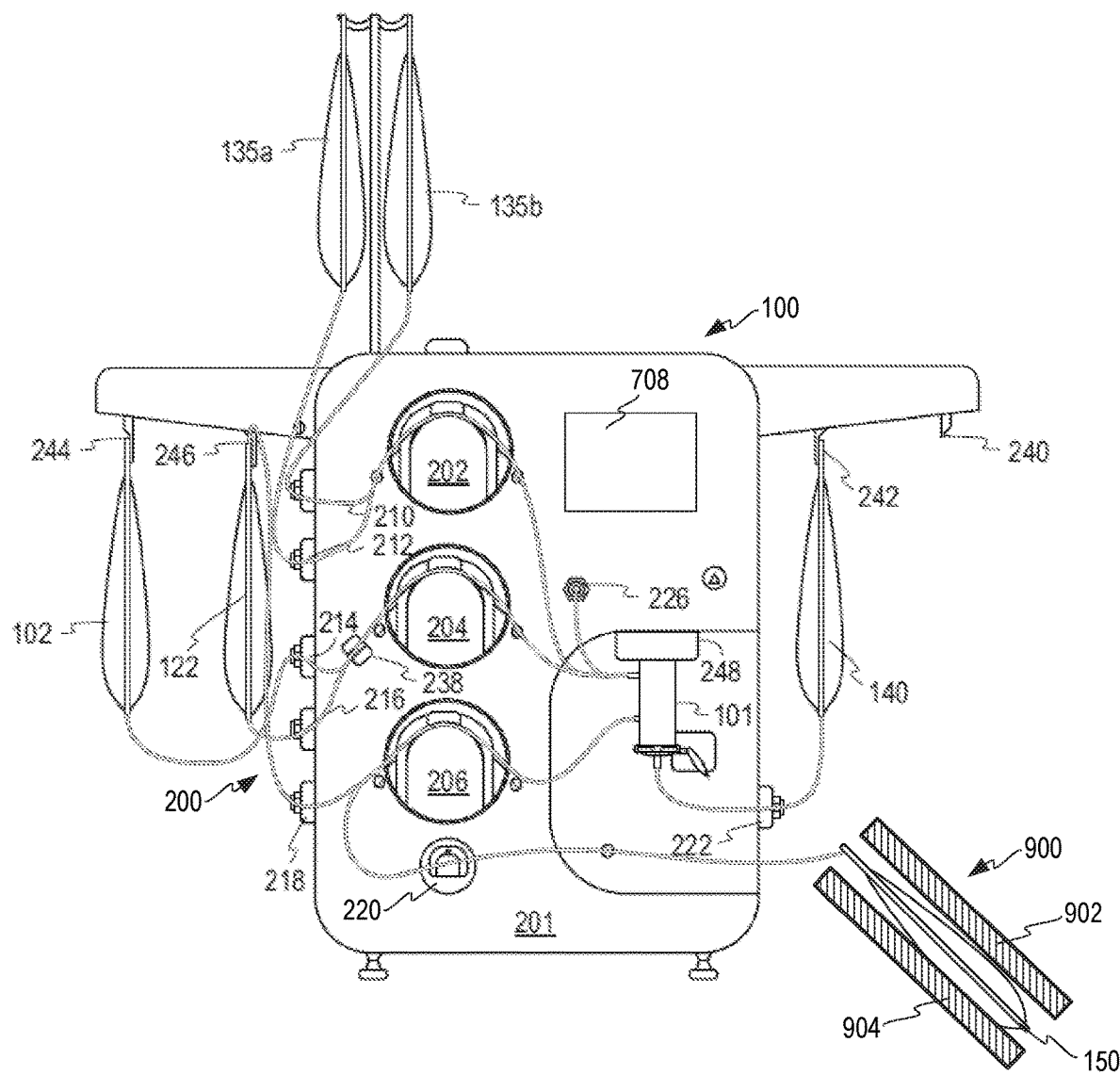
FIG. 11 is a frontal view of a reusable cell processing system with a disposable fluid circuit loaded thereon.
Figure 12:
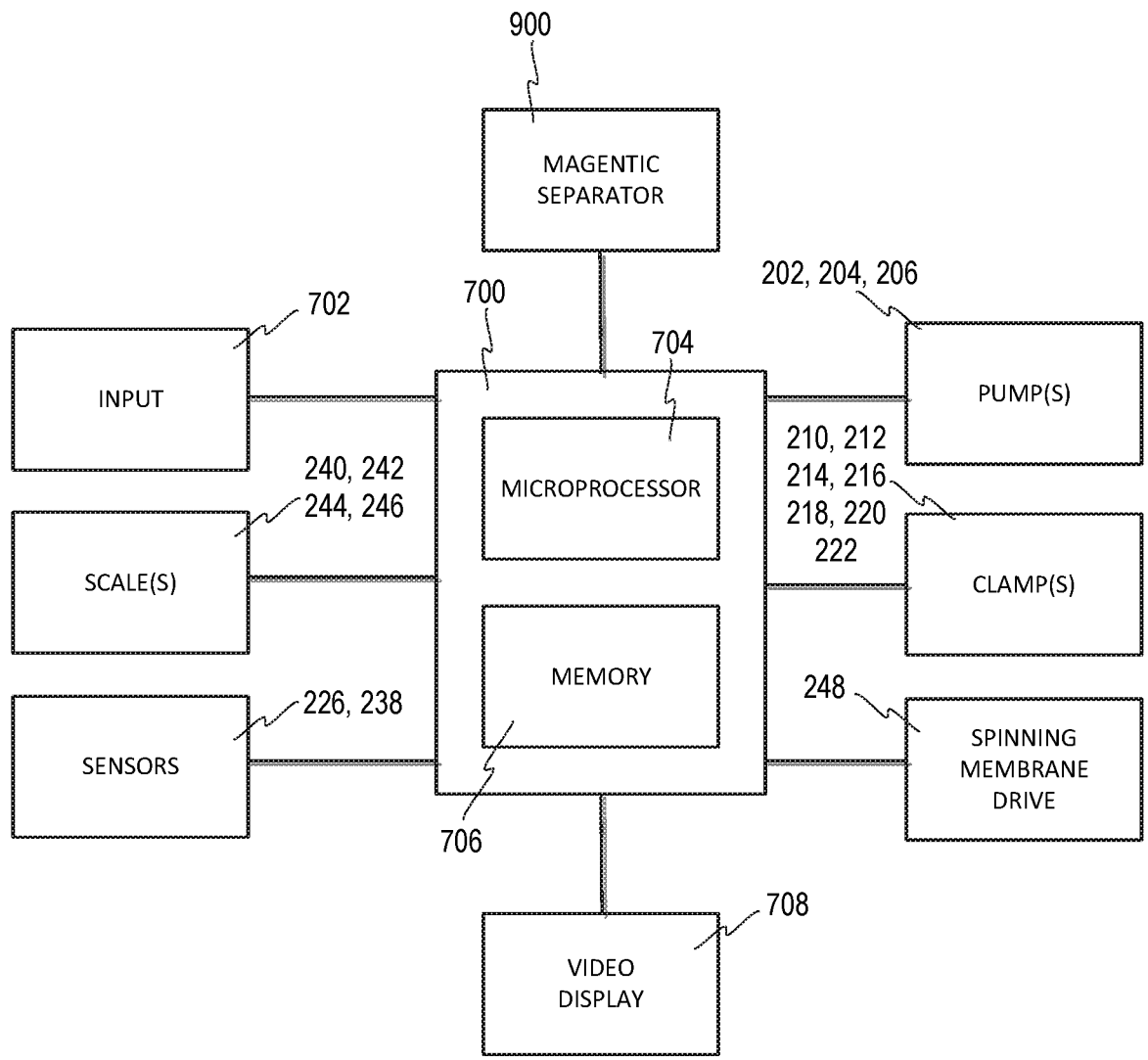
FIG. 12 is a schematic view of the control circuitry of the apparatus of FIG. 11.
Figure 13:
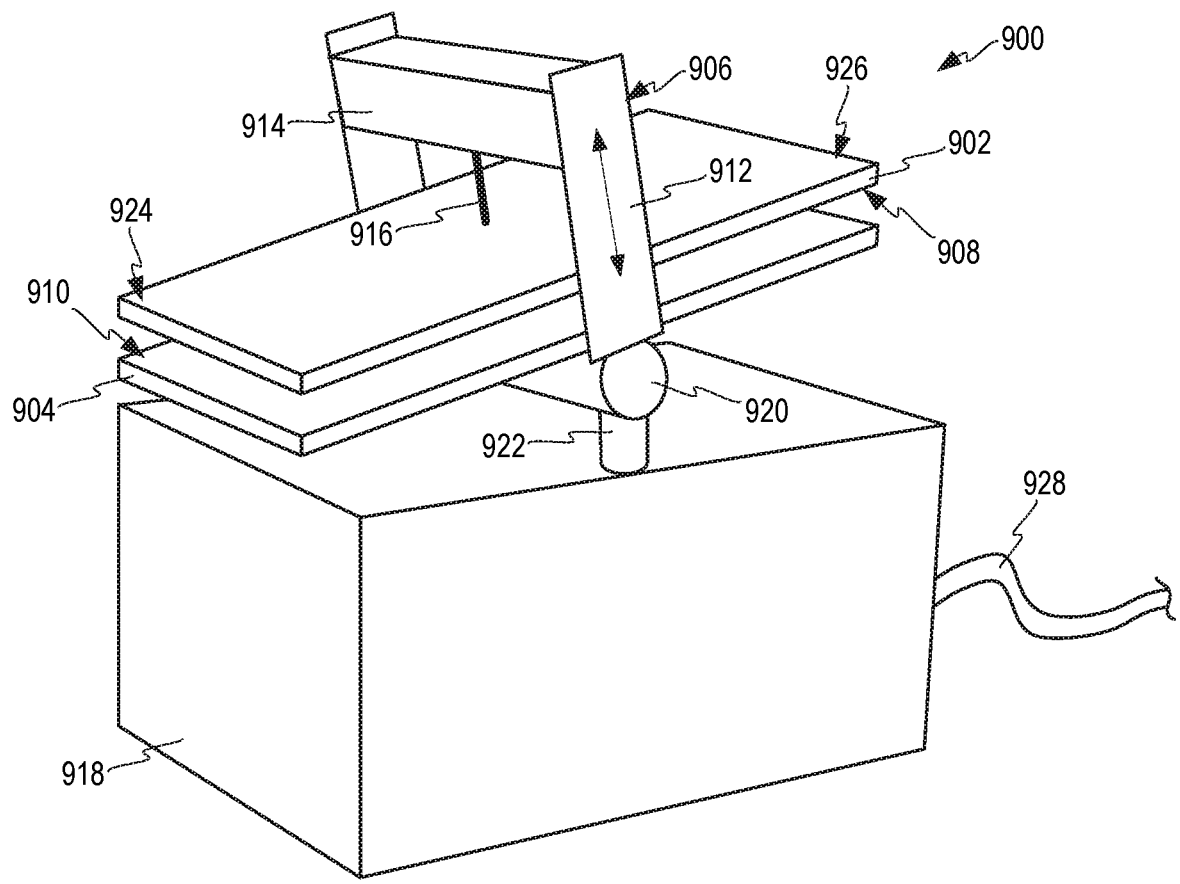
FIG. 13 is a perspective view of a reusable magnetic separation or selection apparatus.

As illustrated in FIGS. 11 and 12, a cell processing system includes a processor 100, 200 to receive a biological fluid to be processed, and a control unit (or controller) 700 coupled to the processor 100, 200. The controller 700 is configured to operate the processor 100, 200 according to a procedure or process to produce or generate a product that may be disposed in a product container. According to the embodiments described herein, the cell processing system may be used in conjunction with a magnetic separator or selector 900, as illustrated generally in FIG. 11 and the details of an embodiment of which are illustrated in FIG. 13. The magnetic separator 900 may be included as part of the system to provide an additional selection of cells of interest or target cells, which target cells were initially separated from a biological fluid by the processor 100, 200. According to the present disclosure, the product container 150 is disposed instead in the magnetic selector 900, between plates or panels 902, 904 (see, e.g., FIG. 11) instead of depending from scale 240.

An embodiment of a magnetic separator or selector 900, which is illustrated schematically in FIG. 11 (as plates 902, 904), is illustrated in detail in FIG. 13. As mentioned above, the magnetic separator 900 includes a first panel or plate 902 and a second, opposing panel or plate 904. According to the embodiments described herein, the first plate 902 comprises a magnet (which may be a permanent magnet or an electromagnet), while the second plate 904 is non-magnetic. It will be recognized that according to other embodiments, the second plate 904 comprises a magnet and the first plate 902 is non-magnetic. As such, the reference to the first and second plates 902, 904 relative to the magnet is intended to be non-limiting.

The plates 902, 904 are mounted on a frame 906 to permit at least one of the plates 902, 904 to translate relative to the other plate 902, 904 in the direction of the double-headed arrow in FIG. 13 between a first position where facing surfaces 908, 910 of the plates 902, 904 are close to each other (potentially, even abutting) and one or more second positions where the inner surfaces 908, 910 of the plates 902, 904 are spaced from each other (as illustrated in FIG. 13). For example, the frame 906 may include one or more side pieces or legs 912 joined by a crosspiece 914, each of the legs 912 having a slot in which a tab or extension from the plate 902 is received to limit the motion of the plate 902 to a linear direction relative to the plate 904. The separator 900 may also include a linear actuator 916, which may be housed in the crosspiece 914 of the frame 906 and a portion of which is illustrated in FIG. 13, that is used to vary the spacing between opposing surfaces of the plates 902, 904. As an alternative, the spacing may be varied using a mechanism that is manually activated (e.g., a fastener that secures the plates 902, 904 in a particular position relative to each other).

The container 150 is intended to be associated with the separator 900, and in particular between the plates 902, 904. In the same fashion as the circuit 100 and apparatus 200 may be referred to as defining a first processor, the circuit 100 (or as much of the interconnected set as disposed in the separator 900) and the separator 900 may be referred to as defining a second processor. Because it is intended for the container 150 to be disposed between the plates 902, 904, the plate 904 may be in the form of a bed, table or tray, and may have a boundary (such as in the form of a rim, lip or flange) that will assist in maintaining the container on the plate 904. According to certain embodiments, the plate 904 (and potentially the plate 902) may have a depression in which the container is received when the container is disposed between the plates 902, 904.

The frame 906 may be mounted on a base 918. According to the illustrated embodiment, the frame 906 may be attached to an axle 920 that is mounted on the base 918 on legs 922, for example. The frame 906 may pivot about the axle 920 relative to the base 918 to vary the elevation of a first end 924 of the plates 902, 904 relative to a second end 926 of the plates 902, 904. The pivoting movement of the frame 906 (and plates 902, 904) may be controlled through using a motor or other actuator. The pivoting movement of the frame 906 may be controlled so as to permit the elevation of the first end 924 to be adjusted and maintained relative to the elevation of the second end 926 to maintain an incline (as illustrated in FIG. 13). Alternatively, the pivoting motion of the frame 906 may cause the elevation of the first and second ends 924, 926 of the plates 902, 904 to alternate back and forth in an oscillating motion, which may be useful in agitating the contents of a container that is disposed between the plates 902, 904 (e.g., container 150 as illustrated in FIG. 11).

The operation of the actuator 916 and the motor or actuator used to vary the relative elevation of the ends 924, 926 of the plates 902, 904 (and thus the inclination of the plates 902, 904) may be controlled by a controller disposed in the base 918 of the magnetic separator 900 (which may be in the form of a microprocessor and memory, and/or other hard-wired circuitry—see also the description of the controller 700, below). Alternatively, the operation of the separator 900 may be controlled by the controller 700 of the apparatus 100. In either event, the separator 900 may include a cable 928 that is coupled to the apparatus 100. The cable 928 may be used to provide a one-way or two-way communication link between the apparatus 100 and the separator 900, and may also be used to provide power to the separator 900 according to certain embodiments.

Having thus described the processor, including disposable circuit 100 and reusable hardware 200, and the separator 900, reference is made to FIG. 12 to discuss additional details of the control unit or controller 700. As mentioned above, the controller 700 may include a microprocessor 704 (which, in fact may include multiple physical and/or virtual processors). According to other embodiments, the controller 700 may include one or more electrical circuits designed to carry out the actions described herein. In fact, the controller 700 may include a microprocessor and other circuits or circuitry. In addition, the controller 700 may include one or more memories 706. The instructions by which the microprocessor 704 is programmed may be stored on the memory 706 associated with the microprocessor 704, which memory/memories 706 may include one or more tangible non-transitory computer readable memories, having computer executable instructions stored thereon, which when executed by the microprocessor 704, may cause the microprocessors 704 to carry out one or more actions as described below.

As is also illustrated in FIG. 12, the controller 700 may be coupled to one or more of the structures described above, for example to receive information (e.g., in the form of signals) from these structures or to provide commands (e.g., in the form of signals) to these structures to control the operation of the structures. As illustrated, the controller 700 may be coupled to the scales 240, 242, 244, 246, the sensors 226, 238 and at least one input 702 to receive information from those devices. Additionally, the controller 700 may be coupled to the pumps 202, 204, 206, the clamps 210, 212, 214, 216, 218, 220, 222, and the drive 248 to provide commands to those devices to control their operation. As also mentioned above, the controller 700 may be coupled to the magnetic separator 900. It may also be possible that the controller 700 receives information from and provides commands to a given structure, such as one of the structures already mentioned (e.g., the magnetic separator 900). The controller 700 may be directly electrically connected to these structures to be coupled to them, or the controller 700 may be directly connected to other intermediate equipment that is directly connected to these structures to be coupled to them.

The at least one input 702 may include a number of different devices according to the embodiments described herein. For example, the input 702 could include a keyboard or keypad by which a user may provide information and/or instructions to the controller 700. Alternatively, the input 702 may be a touch screen, such as may be used in conjunction with a video display 708 that is disposed on the front panel 201 of the device 200 (see FIG. 11), the video display 708 also being coupled to the controller 700 (see FIG. 12). The input 702 could also include a reader or scanner, such as a barcode reader or scanner or an RFID reader. The assembly of the input/touch screen 702 and video display 708 may be one of the afore-mentioned structures to which the controller 700 is coupled from which the controller 700 receives information and to which the controller 700 provides commands. According to still other embodiments, the input 702 may be in the form of computer equipment that permits the cell processing system including the controller 700 to communicate (whether via wires, cables, etc. or wirelessly) with other cell processing systems over a local network, or with other cell processing systems or other computer equipment (e.g., a server) over local networks, wide area networks, or the Internet. According to such an embodiment, the input may include an internal transmitter/receiver device.

Having discussed the structure of embodiments of the cell processing system disclosed herein, the operation of the cell processing system is now discussed. In general terms, the operator may first activate (e.g., switch on) apparatus 200, at which point the apparatus 200 conducts self-calibration checks, including the checking of the peristaltic pumps 202, 204, 206, clamps 210, 212, 214, 216, 218, 220, 222, and sensors 226, 238. Similar self-calibration checks may be performed relative to the separator 900 when the operator activates the separator 900, or when the operator activates the apparatus 200. Apparatus 200 may then prompt the user to enter or modify process parameters using the input 702, including by way of example and not by way of limitation the amount of cell suspension to be processed, the number of cycles to take place, etc. The apparatus 200 may then prompt the operator to mount the disposable set 100, after which apparatus 200 automatically checks to determine whether the disposable set 100 is properly installed. Once the set 100 is properly installed, the controller 700 prompts the operator to connect the biological fluid (e.g., 102 of FIG. 11) via a spike connector or sterile connection (e.g., 103, 104 of FIG. 2) and the wash medium (e.g., 135a, 135b of FIG. 11) via a spike connector (e.g., 134a, 134b of FIG. 2) or sterile welding. In one embodiment, the biological fluid/cells may be apheresis-collected leukocytes, and the wash medium may be a saline solution or a buffer.

Once the operator confirms that the solutions are connected, the controller 700 primes the disposable set 100. In the embodiment discussed above, the set 100 may be primed with saline, although other biocompatible aqueous solutions may also be used. The controller 700 then commences processing the biological fluid/cells, which may have been recently obtained via apheresis (or leukapheresis), refrigerated overnight, etc. The biological fluid/cells is/are transferred from source container (e.g., 102 of FIG. 11) through the set to the spinning membrane separator 101 via the operation of one or more peristaltic pumps 202, 204, 206. In a similar fashion, the wash medium may be delivered from its container (e.g., 135a, 135b of FIG. 11) through the set to the spinning membrane separator 101. The biological cells are collected in the in-process container (e.g., 122 of FIG. 11), while supernatant is separated and removed to waste container (e.g., 140 of FIG. 11). In regard to this portion of the method, the disclosure of the embodiments above is also incorporated by reference herein in its entirety, and in particular the settings for the apparatus described in the disclosure and figures.

According to the present disclosure, a monoclonal antibody solution may be introduced to the solution in the in-process container 122, and incubated for a period of time to allow for interaction between the monoclonal antibodies in the solution and the target cells (which may be white blood cells of a particular phenotype, such as CD34+ peripheral blood stem cells, CD3+/CD28+ T-cell lymphocytes, and CD8+ plasma B-cells, which cells may also be referred to as target cells). The spinning membrane separator 101 may be used to mix the cells and then to wash the cells, removing any unbound monoclonal antibodies). In regard to this portion of the method, the disclosure of the embodiments above is again incorporated by reference herein in its entirety, and in particular the settings for the apparatus described in the disclosure and figures.

At this point, a non-specific magnetic particle solution (e.g., a magnetic bead solution, such as ferrofluid (FF)) may be introduced to the suspension in the in-process container 122, incubated for a period of time to allow for interaction between the ferrofluid and the non-specific end of the monoclonal antibodies, mixed and (optionally) washed to remove any unbound ferrofluid. The target cells with associated magnetic particles may then be transferred to the container 150 that is disposed in magnetic separator 900.

The magnetic plate 902 may be actuated and/or positioned adjacent the container 150 to attract the magnetic particles, and in particular the magnetic particles associated with the target cells, to a particular portion of the container 150 (e.g., the upper section of the container 150 adjacent the plate 902 as illustrated in FIG. 11). The container 150 may then be agitated and the negative fractions removed. Additional fluid then may be added to the container to achieve a desired final volume, and the magnet may be disengaged and/or the plate 902 may be moved to relative to the plate 904 so that the plates 902, 904 are spaced (which may include reference to further spacing as well). Once the processing is completed, the controller prompts the operator to sample, seal and remove the product container 150.

Figure 14:
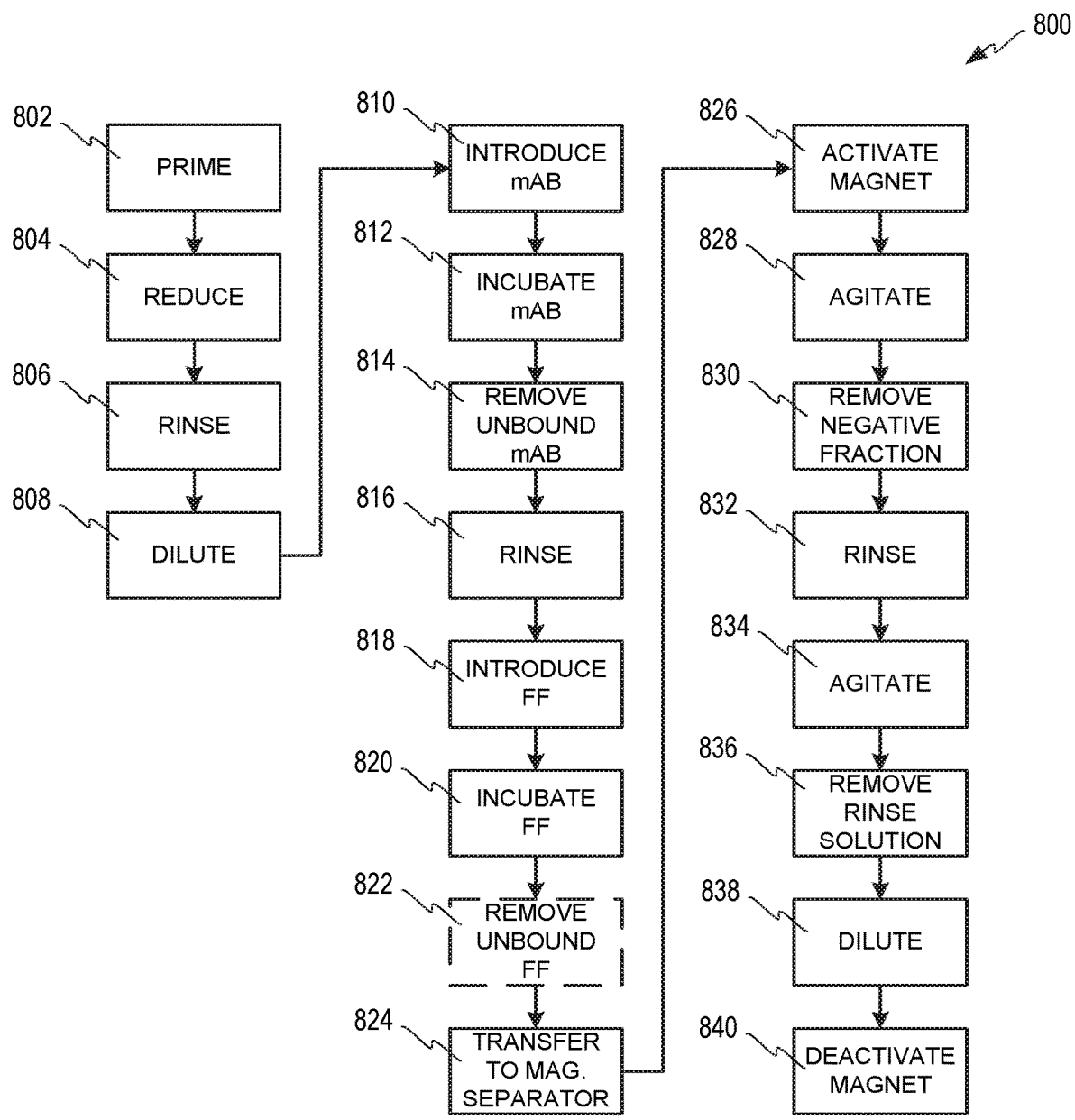
FIG. 14 is a flowchart of one embodiment of a method of operating a reusable cell processing apparatus with a disposable fluid circuit loaded thereon, such as is illustrated in FIG. 11, to process a biological fluid.
Figure 15:
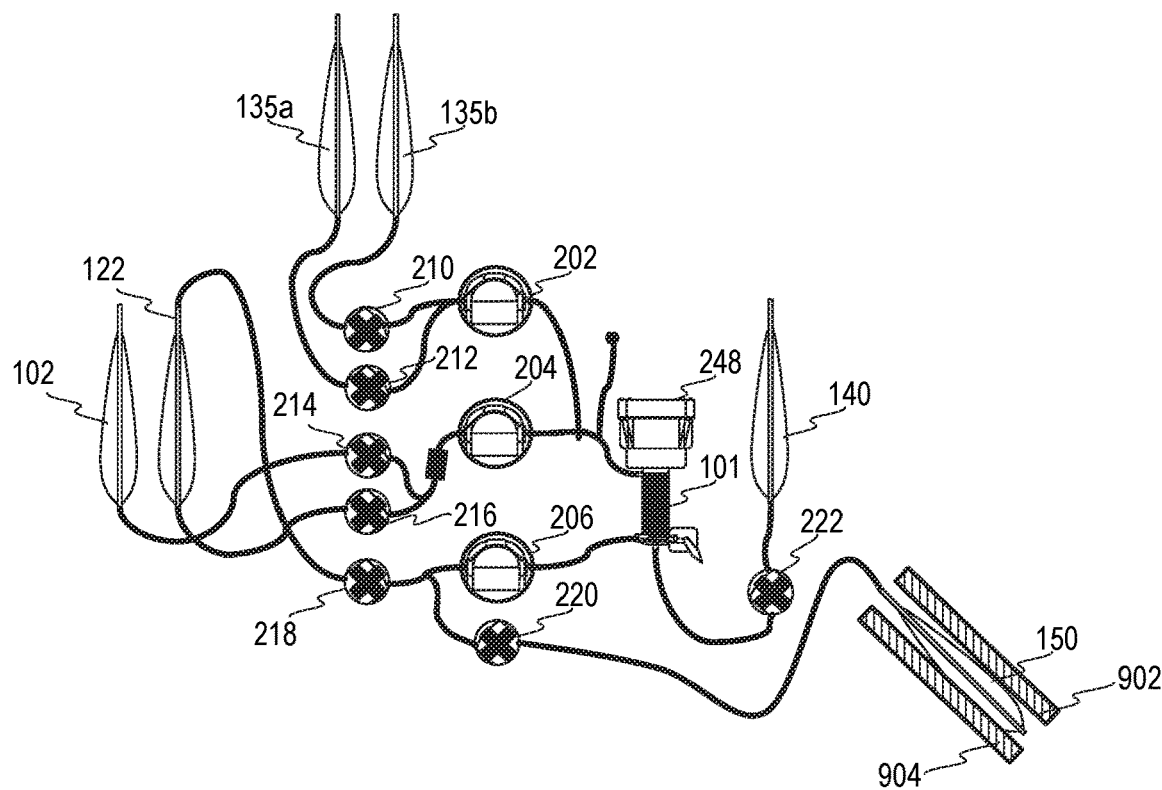
FIGS. 15-32 are schematic views of selected portions of the reusable cell processing apparatus, the reusable magnetic separation apparatus, and the disposable fluid circuit illustrating the movement of materials to various elements and along various fluid paths of the fluid circuit according to the method illustrated in the flowchart of FIG. 14.
Figure 16:
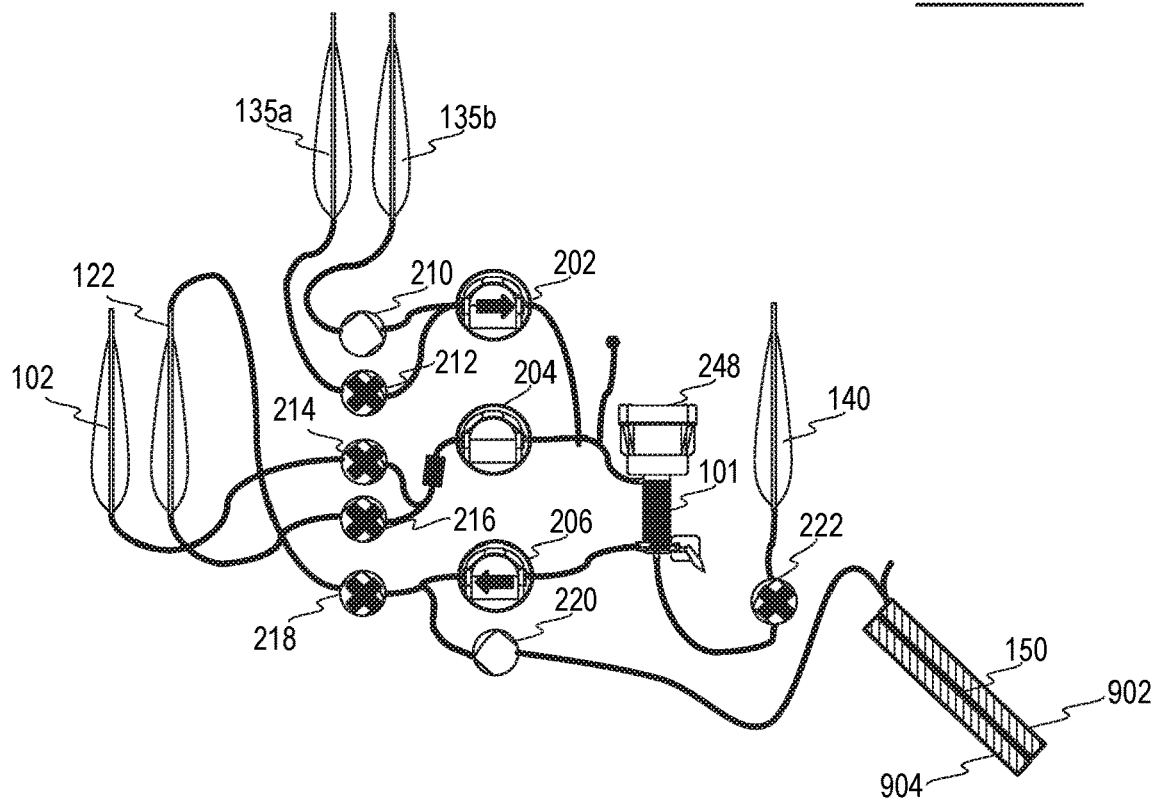
Figure 17:
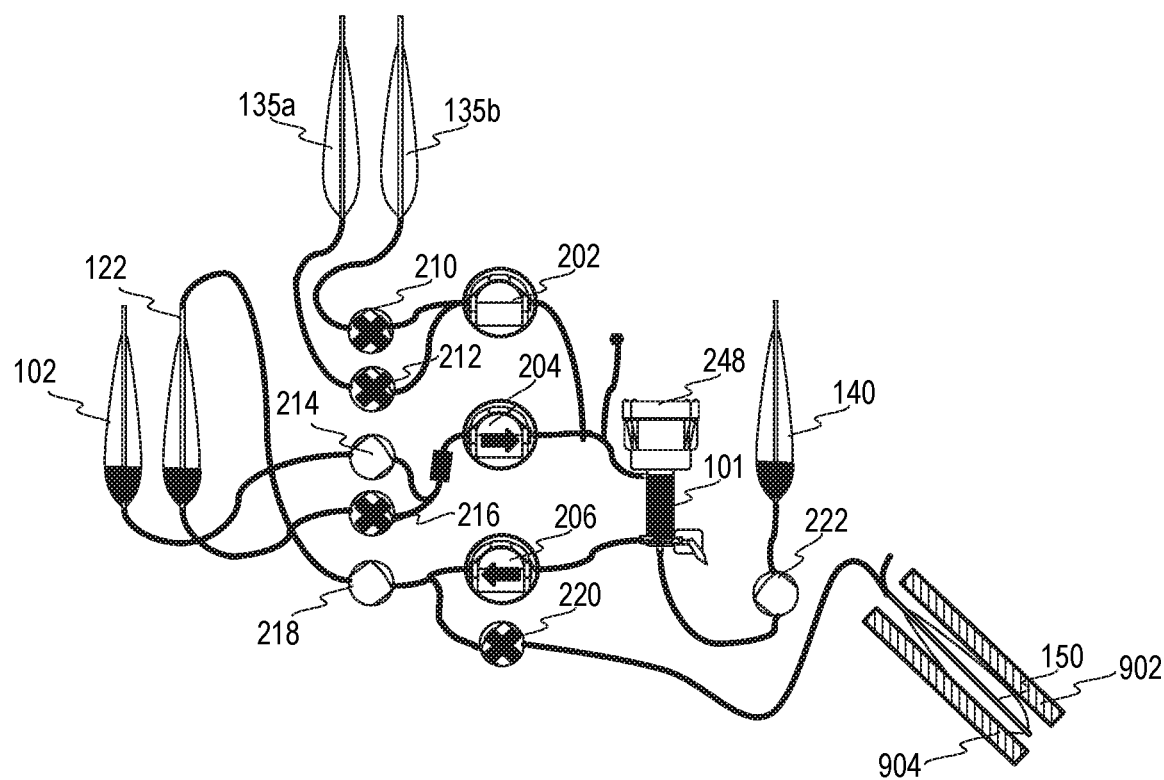
Figure 18:
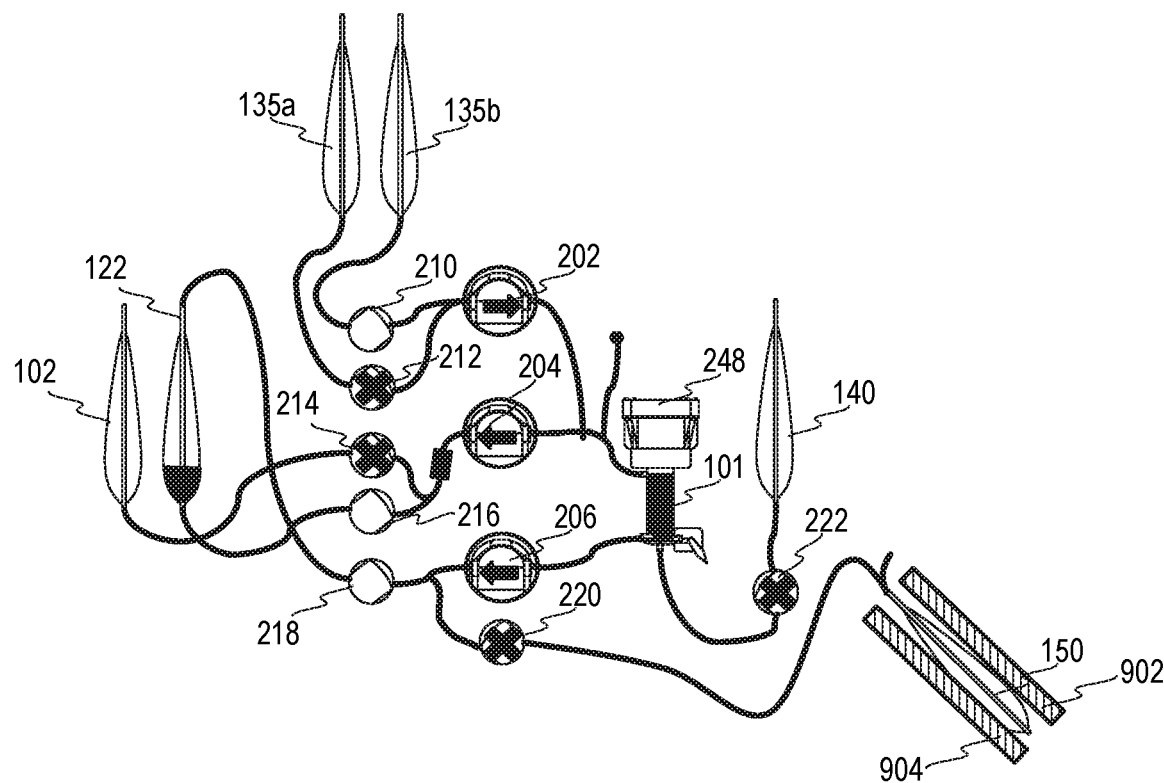
Figure 19:
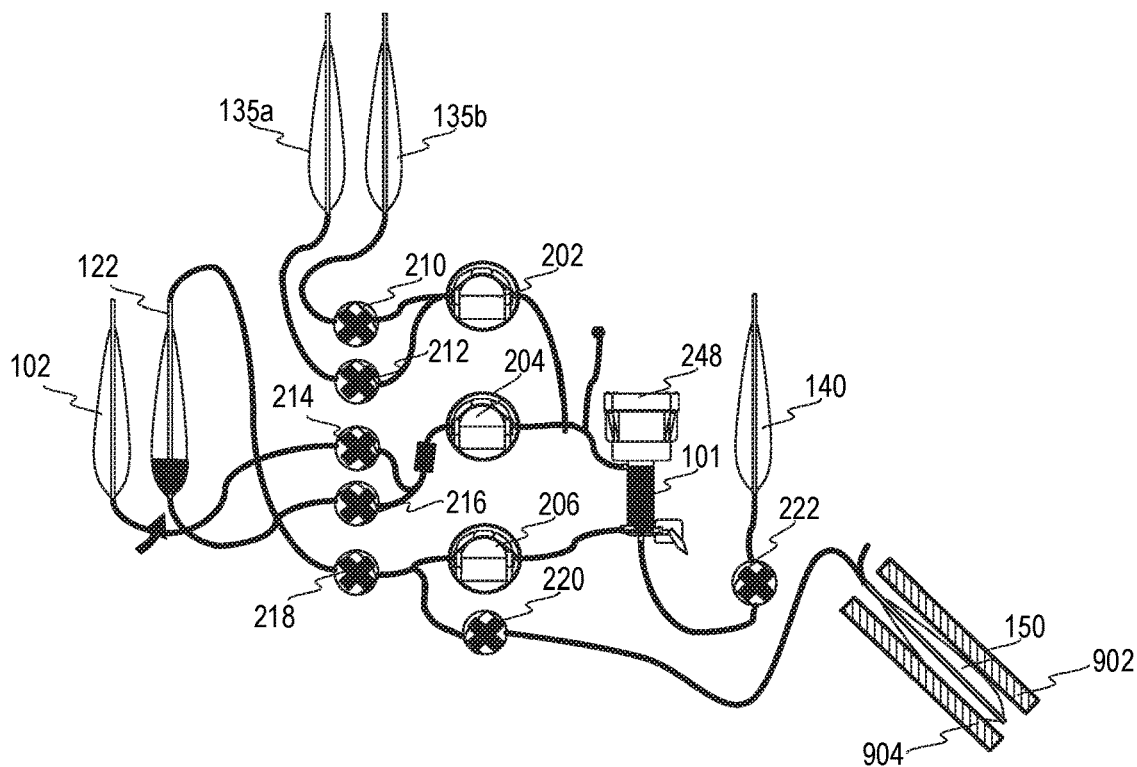
Figure 20:
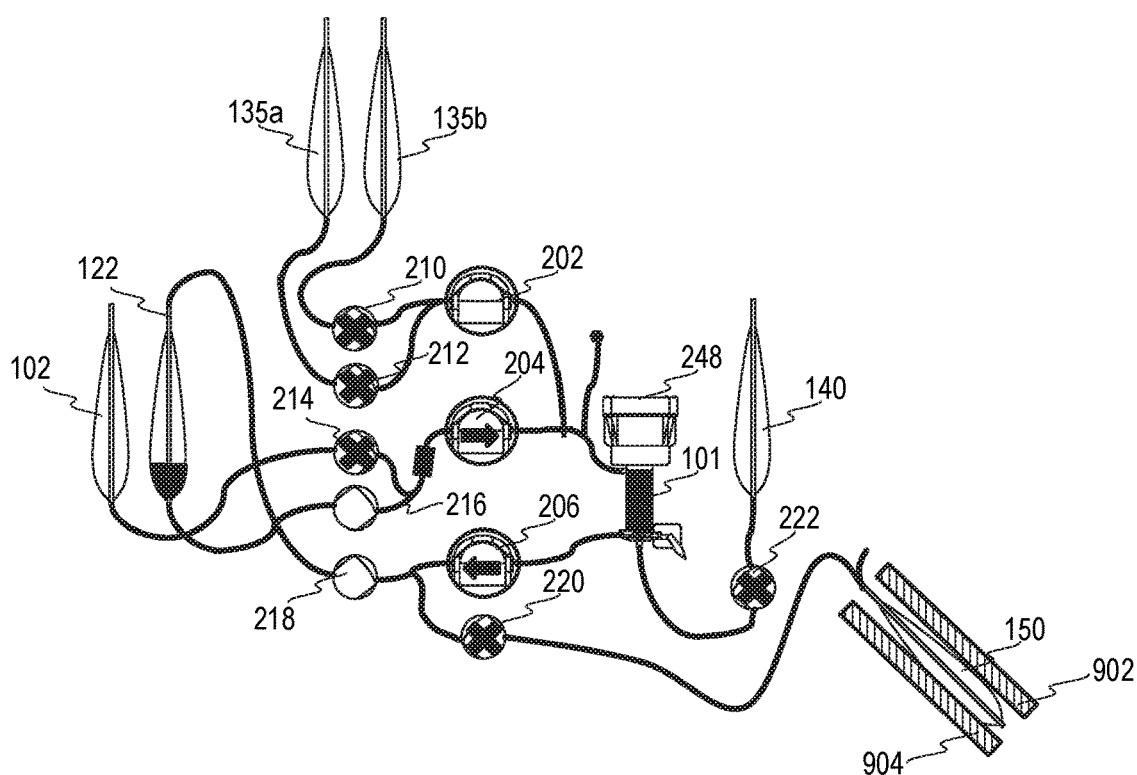
Figure 21:
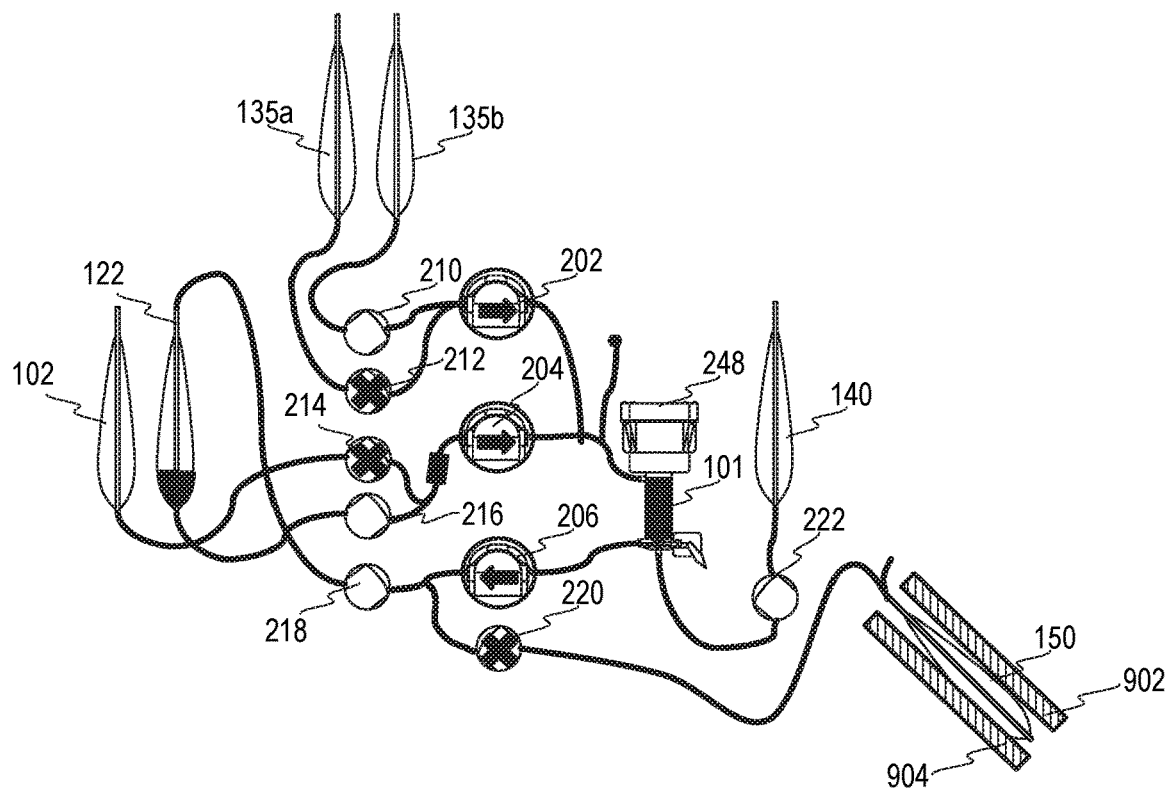
Figure 22:
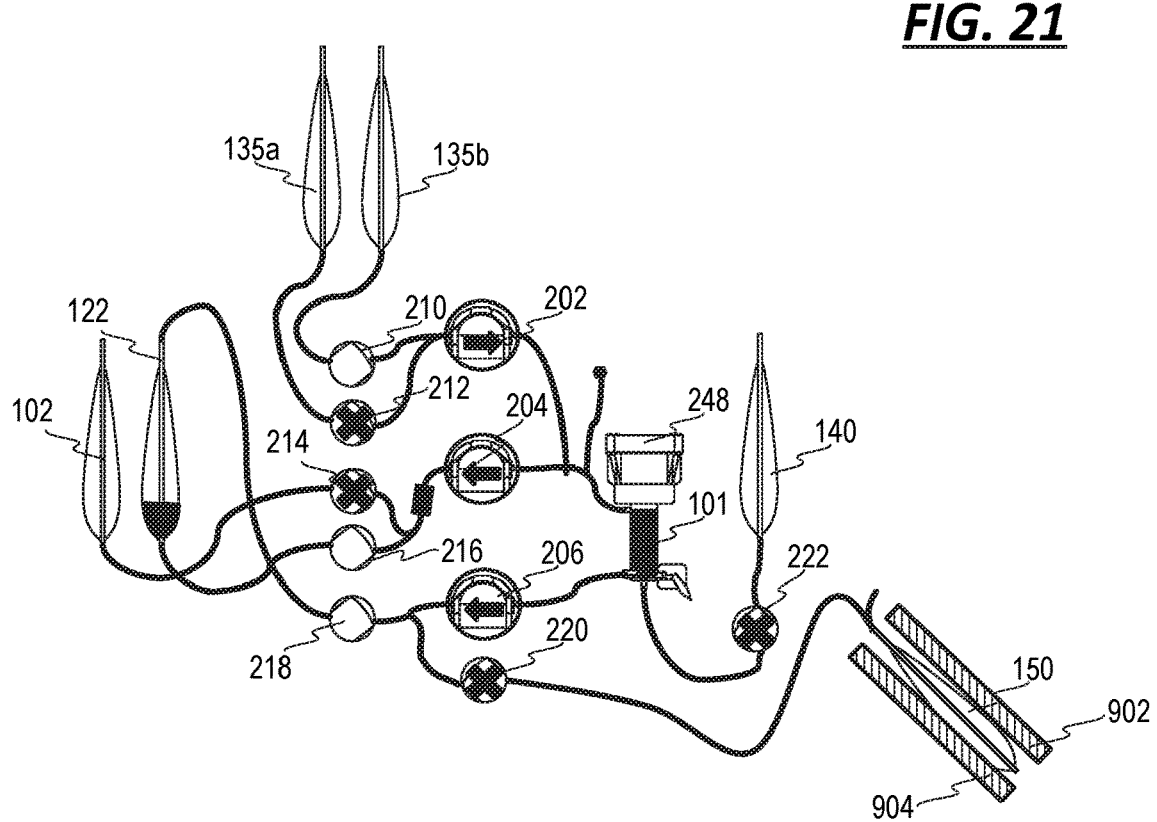
Figure 23:
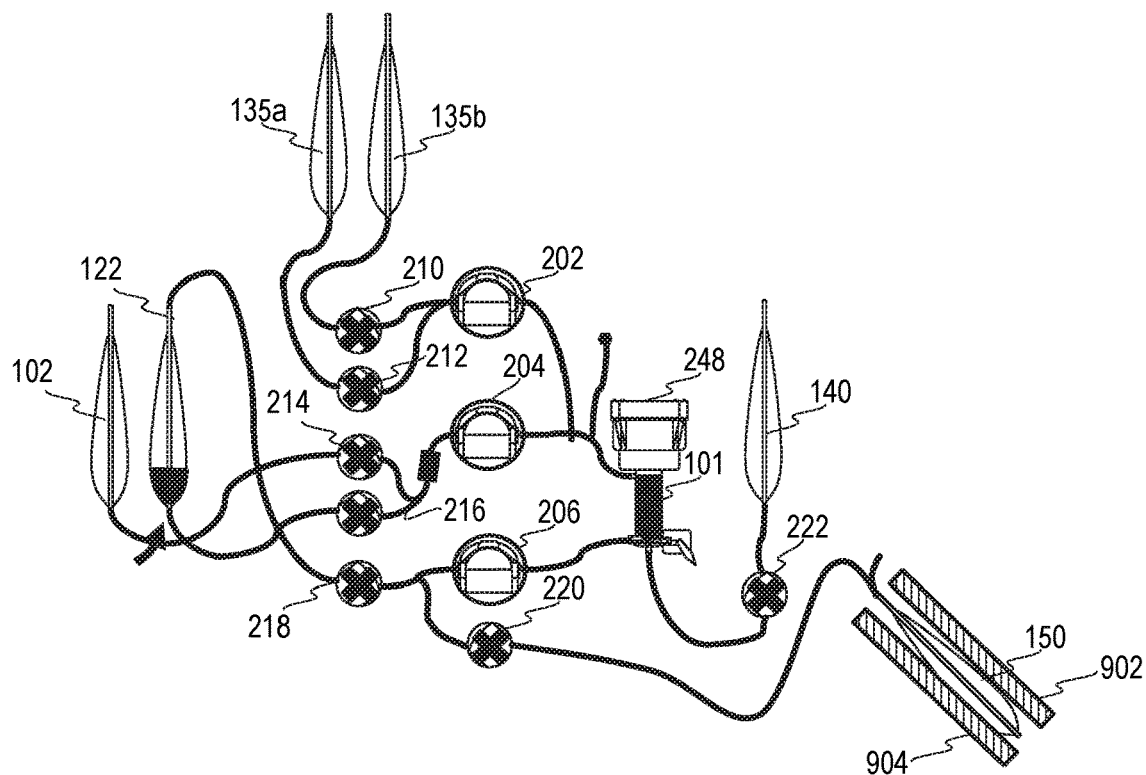
Figure 24:
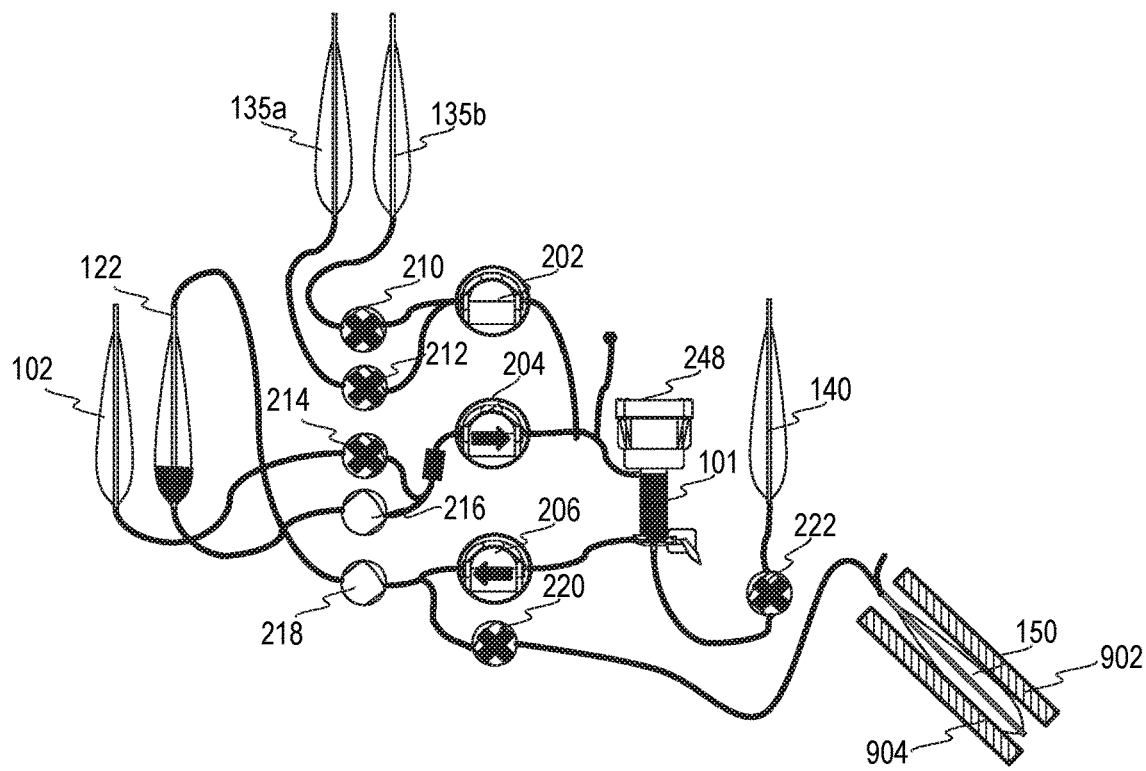
Figure 25:
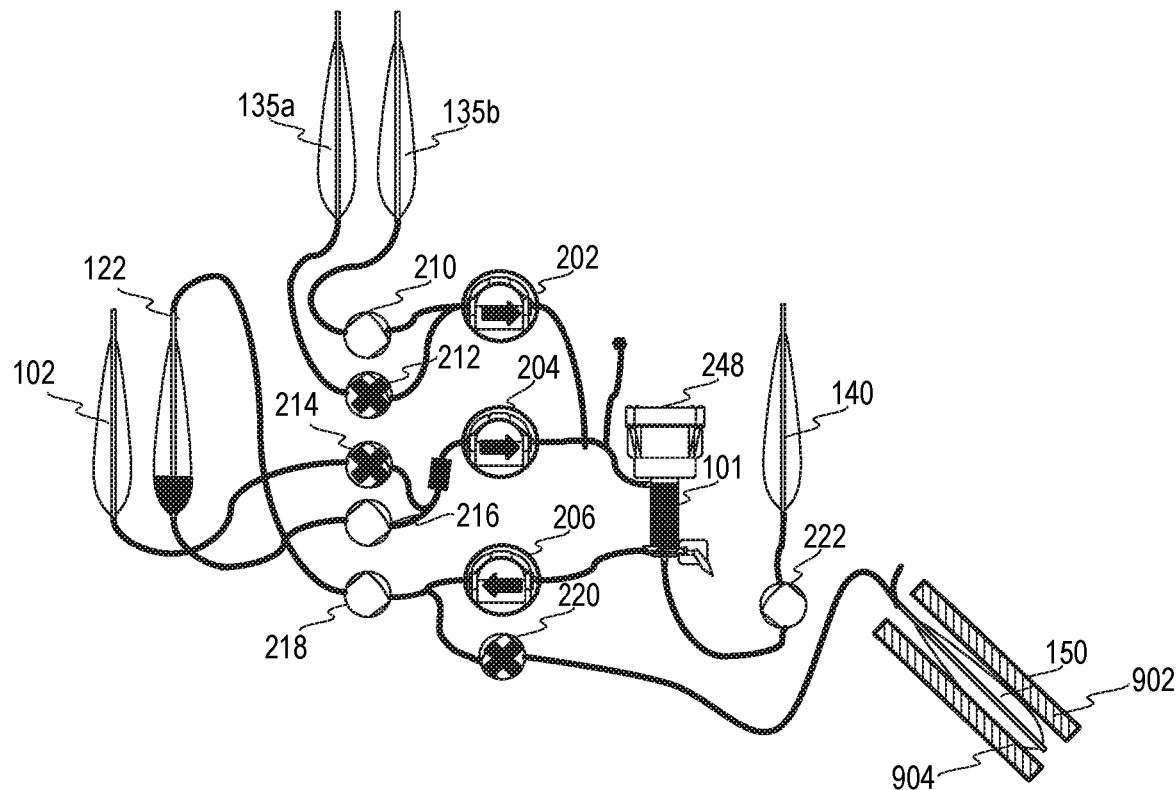
Figure 26:
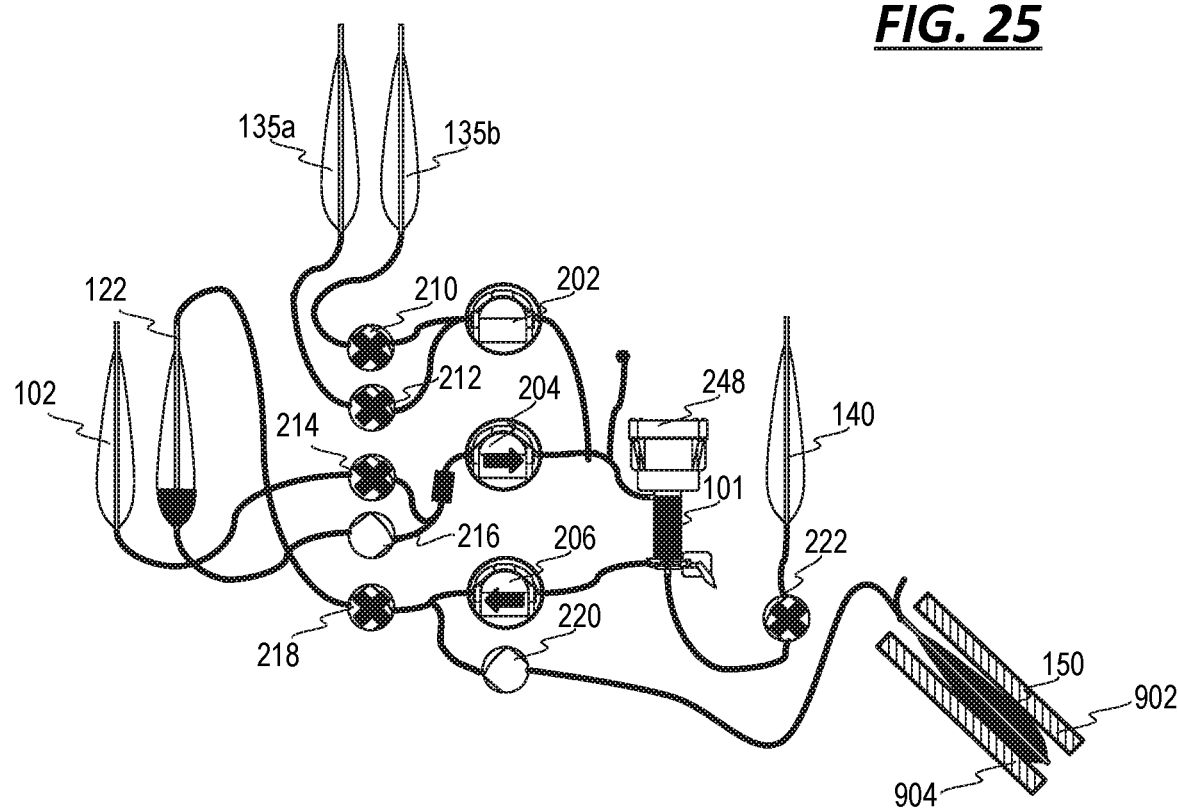
Figure 27:
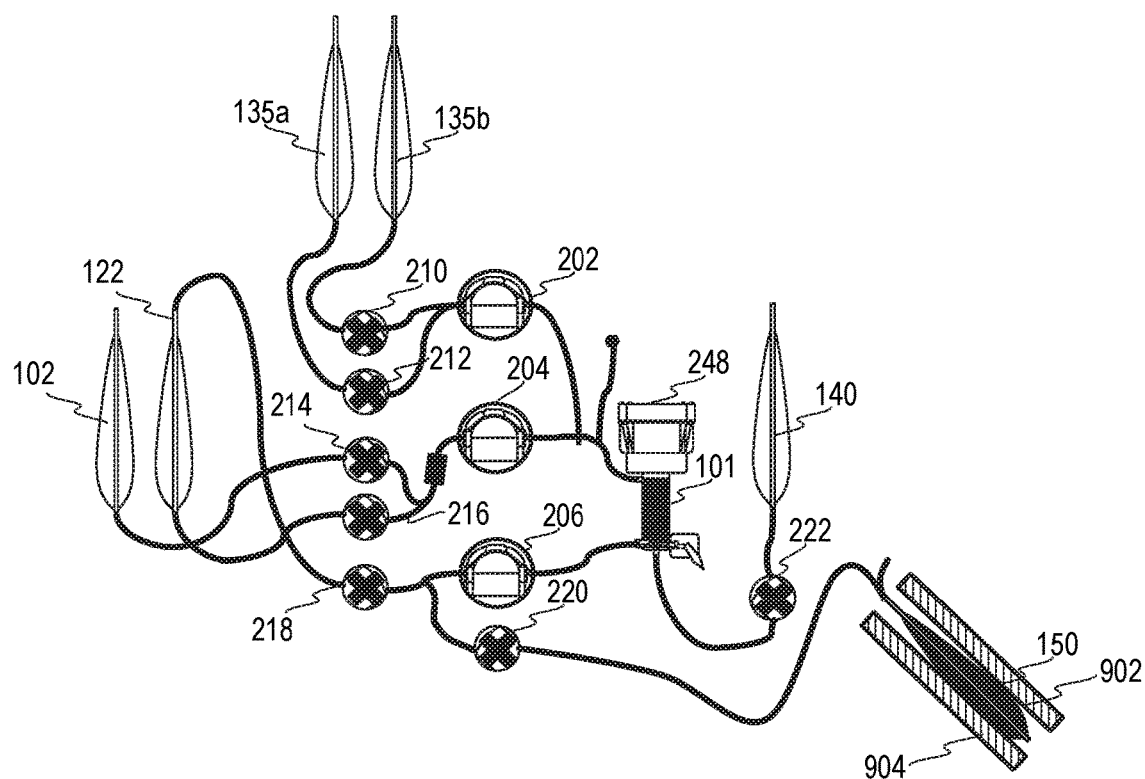
Figure 28:
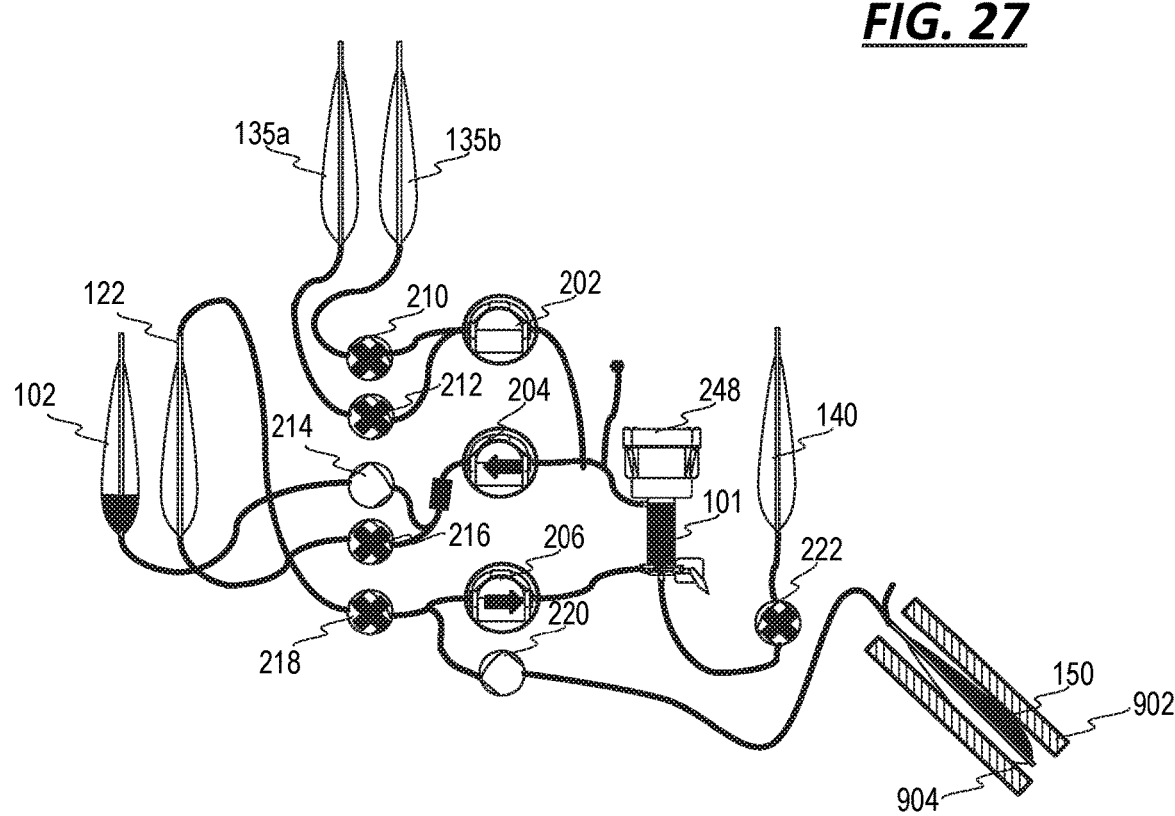
Figure 29:
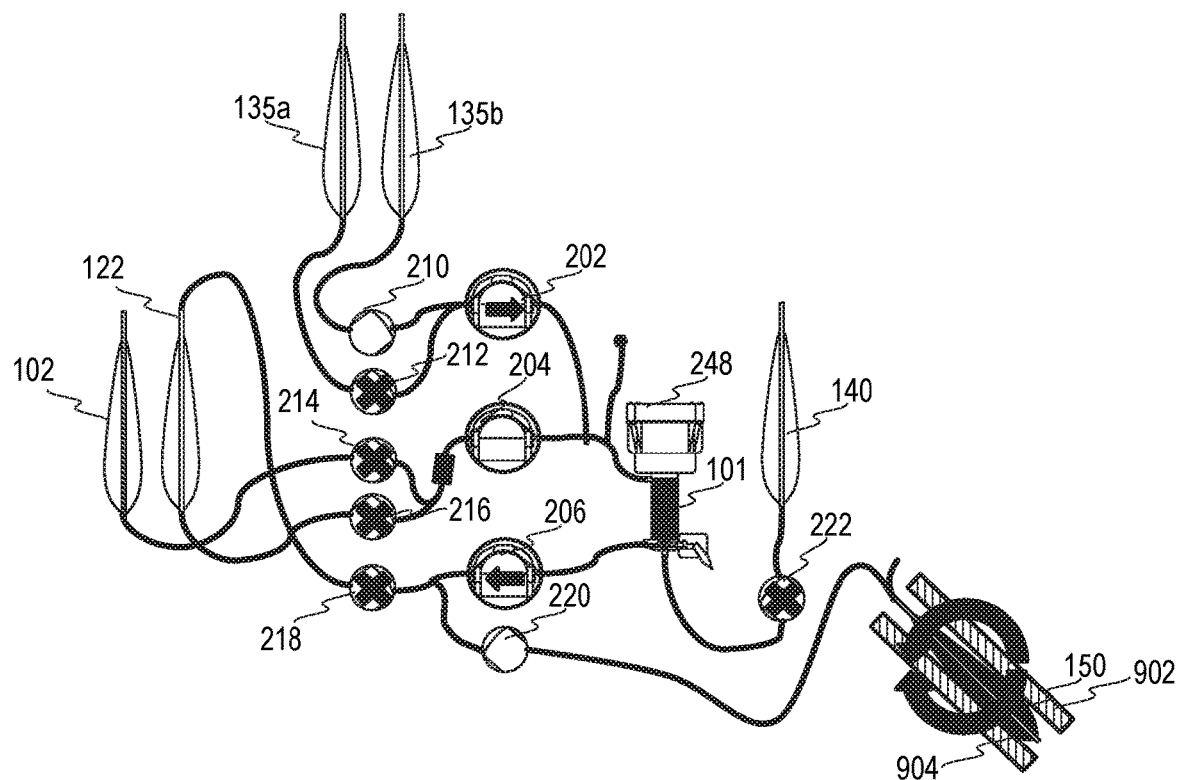
Figure 30:
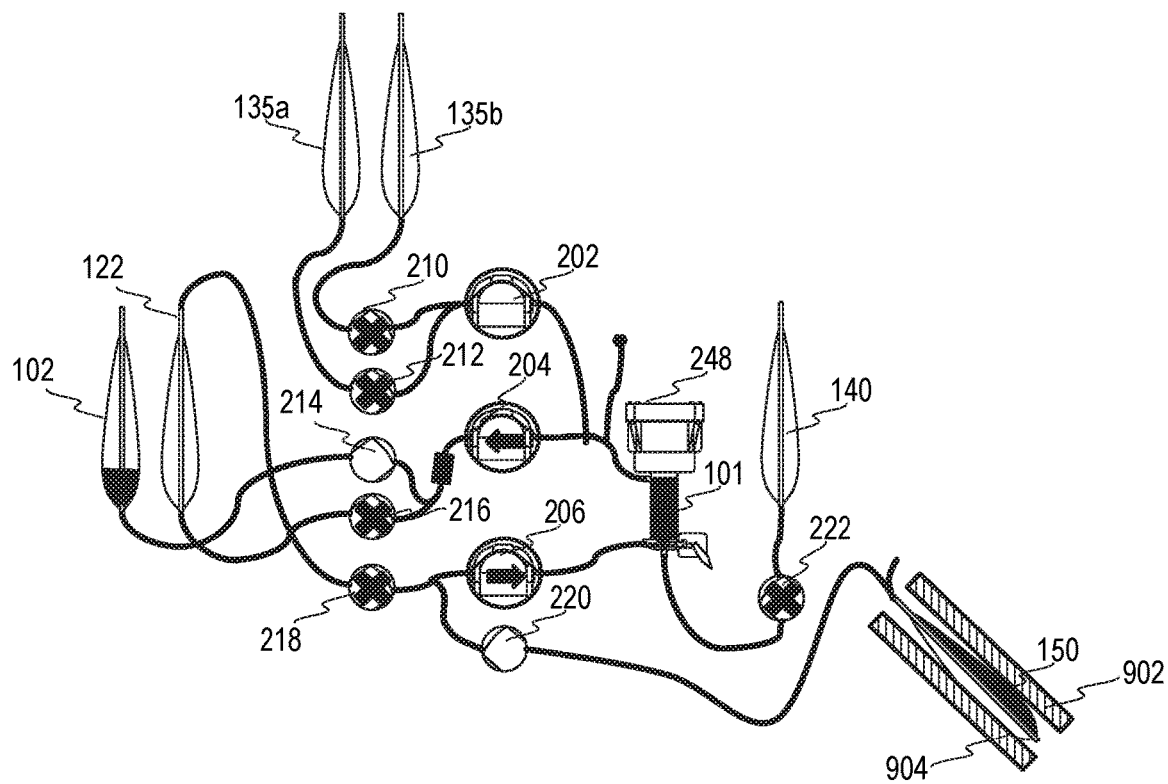

A specific embodiment of a method 800 of operating the apparatus 200 is provided in FIG. 14, with particular operational states of the processor 100, 200 and separator 900 illustrated in FIGS. 15-32. According to this embodiment, the method 800 of operating the apparatus 200 includes several steps, and some of the steps may be grouped or organized into one or more cycles. For example, reduction, rinse and dilution steps 804, 806, 808 may define a cycle, which cycle may be repeated several times to define a multi-cycle procedure; the fact that a single cycle is illustrated does not exclude the possibility that additional cycles may be performed. Further, it will be recognized that an apparatus 200 need not perform every step illustrated in FIG. 14, but an apparatus 200 may operate as illustrated in FIG. 14 according to this disclosure.

To begin, the controller 700 may cause the apparatus 200 to perform the step of priming at block 802. According to this step, wash media from one or both of the wash media containers 135a, 135b is transferred to the disposable set 100. In fact, a small amount of wash media may be transferred to each of the other containers 102, 122, 140 to ensure that the containers 102, 122, 140 are connected. To this end, the controller 700 may cause clamps 210, 212, 214, 216, 218, 222 to open to permit the transfer of fluid to the containers 102, 122, 140.

As part of this priming action, the controller 700 first may operate the magnetic separator 900 to evacuate the container 150 by moving the plates 902, 904 toward each other to force or express air from the container 150 into the set 100 (e.g., into the container 122). Compare FIG. 15 with FIG. 16. With the container 150 compressed between the plates 902, 904, the controller 700 may open clamps 210, 220 and operate pumps 202, 206 to move fluid from the wash container 135b into the lines that connect with the container 150. See FIG. 16. It is possible that the controller 700 may operate the separator 900 to space the plates 902, 904 so that some fluid may be transferred to the container 150 as well. Compare FIG. 16 and FIG. 17. Once the priming step is complete, the clamps 210, 220 may be closed.

The method 800 continues to block 804, where the controller 700 causes the apparatus 200 to perform a reduction step. According to this step, the controller 700 causes the biological fluid from the source container 102 (and optionally wash media from the wash media container(s) 135a, 135b) to be transferred to the separator 101. See FIG. 17. For example, the controller 700 may open clamp 214 and operate pump 204 to transfer the fluids from the container 102 to the separator 101. The separator 101 (in conjunction with operation of the drive 248 by controller 700) produces two streams: a first, or retentate, stream that is directed into the in-process container 122, and a second, or filtrate, stream that is directed into the waste container 140. For example, the controller 700 may open clamp 218 and operate pump 206 to cause flow into the in-process container 122 (clamp 220 being closed), and may open clamp 222 to permit flow into the container 140. As a consequence, plasma and platelets are removed from the biological fluid, and white blood cells are transferred to the in-process container 122.

To facilitate the separation of the plasma and platelets from the white blood cells within the biological fluid, the membrane of the separator 101 may be a thin sheet (10-50 μm in thickness) of polycarbonate with pore sizes of approximately 4 μm, by way of example and not by way of limitation. The pore size is selected to allow platelets (which may be 2-4 μm in size) to pass through, but not the target cells.

After the step of block 804 is complete, the controller 700 causes wash media to be passed through the set 100 (i.e., the set is rinsed) and the media is added to the in-process bag 122 at block 806. See FIG. 18. This may be achieved, for example, by closing clamps 214, 222, while opening clamps 210 (and/or 212), 216, 218 and operating pumps 202, 204, 206 as illustrated. After block 806, the method 800 proceeds to block 808, where the controller 700 may cause additional wash media to be added to the in-process bag 122, if required. As mentioned above, the actions of blocks 804-808 may be repeated as additional cycles, as may be required, before the method 800 continues to block 810. When block 808 is complete, the method 800 may continue with block 810 to start the process of associating magnetic particles with the target cells.

At block 810, all of the clamps 210, 212, 214, 216, 218, 220, 222 are closed. See FIG. 19. According to one embodiment, the processor 100, 200 may automatically pause at this point, so that the operator can manually inject a monoclonal antibody (mAb) solution into the in-process container 122; for example, an introducer container may be attached to the in-process container 122 either prior to the procedure or in a sterile manner during the procedure and the solution is injected into the in-process container 122 from the introducer container. According to other embodiments, the monoclonal antibody is introduced automatically into the in-process container 122. The method 800 may then proceed to block 812, where the contents of the container 122 may be permitted to remain in the container 122 for a period of time to allow for interaction between the monoclonal antibodies and the target cells. As part of the incubation step at block 812, the clamps 216, 218 may be opened and pumps 204, 206 and drive 248 may be operated to mix the suspension in the container 122 to improve the interaction between the monoclonal antibodies and target cells. See FIG. 20. For example, the spinning membrane 101 may be operated at a speed of between 500-700 rpm. Transfer of fluid from one or both of the wash solution containers 135a, 135b may occur at this time to optimize the volume for incubation. According to one embodiment, the total incubation time (including time spent mixing the contents of the in-process container 122) may be thirty minutes, while the incubation temperature may be room temperature.

Continuing at block 814, the apparatus 200 may be operated to remove excess, unassociated or unbound mAb from the contents of the container 122. To achieve this, the clamps 216, 218, 222 are opened and pumps 204, 206 and drive 248 are operated, with the target cells and bound mAb being returned to the container 122 and the unbound mAb being transferred to the container 140. See FIG. 21. The clamp 210 may also be opened and pump 202 operated to introduce wash solution at the same time. The clamp 222 may be closed while the clamp 210 is open and the pump 202 operated to rinse any remaining target cells bound to mAb into the container 122, at block 816. See FIG. 22.

It should be mentioned that the exemplary membrane of the separator 101 described above, a thin sheet (10-50 μm in thickness) of polycarbonate with pore sizes of approximately 4 μm, also should sufficient function to remove the monoclonal antibodies from the target cells with associated monoclonal antibodies. In particular, the monoclonal antibodies may have a size of approximately 50 nm, such that the pore size provided above should be suitable.

At block 818, all of the clamps 210, 212, 214, 216, 218, 220, 222 are again closed. See FIG. 23. According to one embodiment, the processor 100, 200 may automatically pause at this point, so that the operator can manually inject a ferrofluid (FF) into the in-process container 122; for example, an introducer container may be attached to the in-process container 122 either prior to the procedure or in a sterile manner during the procedure and the ferrofluid is injected into the in-process container 122 from the introducer container. According to other embodiments, the ferrofluid is introduced automatically into the in-process container 122. The method 800 may then proceed to block 820, where the contents of the container 122 may be permitted to remain in the container 122 for a period of time to allow for interaction between the monoclonal antibodies and the magnetic particles (e.g., beads) in the ferrofluid. As part of the incubation step at block 820, the clamps 216, 218 may be opened and pumps 204, 206 and drive 248 may be operated to mix the suspension in the container 122 to improve the interaction between the monoclonal antibodies and magnetic particles. See FIG. 24. Transfer of fluid from one or both of the wash solution containers 135a, 135b may occur at this time to optimize the volume for incubation.

Continuing to an optional block 822, the apparatus 200 may be operated to remove excess or unbound magnetic particles from the contents of the container 122. To achieve this, the clamps 216, 218, 222 are opened and pumps 204, 206 and drive 248 are operated, with the target cells and bound magnetic particles being returned to the container 122 and the unbound magnetic particles being transferred to the container 140. See FIG. 25. The clamp 210 may also be opened and pump 202 operated to introduce wash solution at the same time.

To begin the magnetic separation or selection of the target cells, the contents of the in-process container 122 are transferred at block 824 from the container 122 to the container 150 that is disposed at the magnetic separator 900, and in particular between the plates 902, 904. To achieve this, clamps 216, 220 are opened and pumps 204, 206 are operated. See FIG. 26. Once this complete and clamps 216, 220 are closed, the method 800 continues to block 826, and the magnet associated with plate 902 is activated, causing the target cells associated with the magnetic particles and any unbound magnetic particles to migrate to a portion of the container, in particular the portion of the container adjacent the plate 902. See FIG. 27.

At this point, the contents of the container 150 are permitted to remain in container 150 for a period of time with the magnet activated (e.g., 30 seconds). At the same time, the method may continue to block 828, where the contents of the container 150 are agitated. For example, the plates 902, 904 may be alternatively inclined back and forth between a position where the first end 924 is higher than the second end 926 and a position where the second end 926 is higher than the first end 924. The actions of blocks 826, 828 may be repeated as several cycles over a longer period of time (e.g., several minutes). Once this portion of the method 800 is complete, the method 800 continues to block 830.

At block 830, the negative fraction is transferred out of the container 150. According to the embodiment illustrated, the clamps 214, 220 are opened and pumps 204, 206 operated to transfer the negative fraction from the container 150 to the source container 102. See FIG. 28. Alternatively, the in-process container 140 (open clamp 216 instead of clamp 214) or an unused solution container (in place of container 102) may be used instead to receive the negative fraction. The method 800 then proceeds to block 832 where the container 150 is rinsed to attempt to remove any cells that are not target cells associated with magnetic particles. To this end, the clamps 210, 220 are opened and pumps 202, 206 operated to move fluid from container 135*b* to the container 150. At the same time or shortly thereafter, the container 150 may be agitated at block 834, by changing the inclination of the plates 902, 904 back and forth. See FIG. 29. The rinse solution and any remaining negative fraction (i.e., the rinsate) is then transferred to the source container 102 (or an unused solution container, for example) at block 836 by closing clamp 210, opening clamp 214, and operating pumps 204, 206 as illustrated. See FIG. 30.

Figure 31:
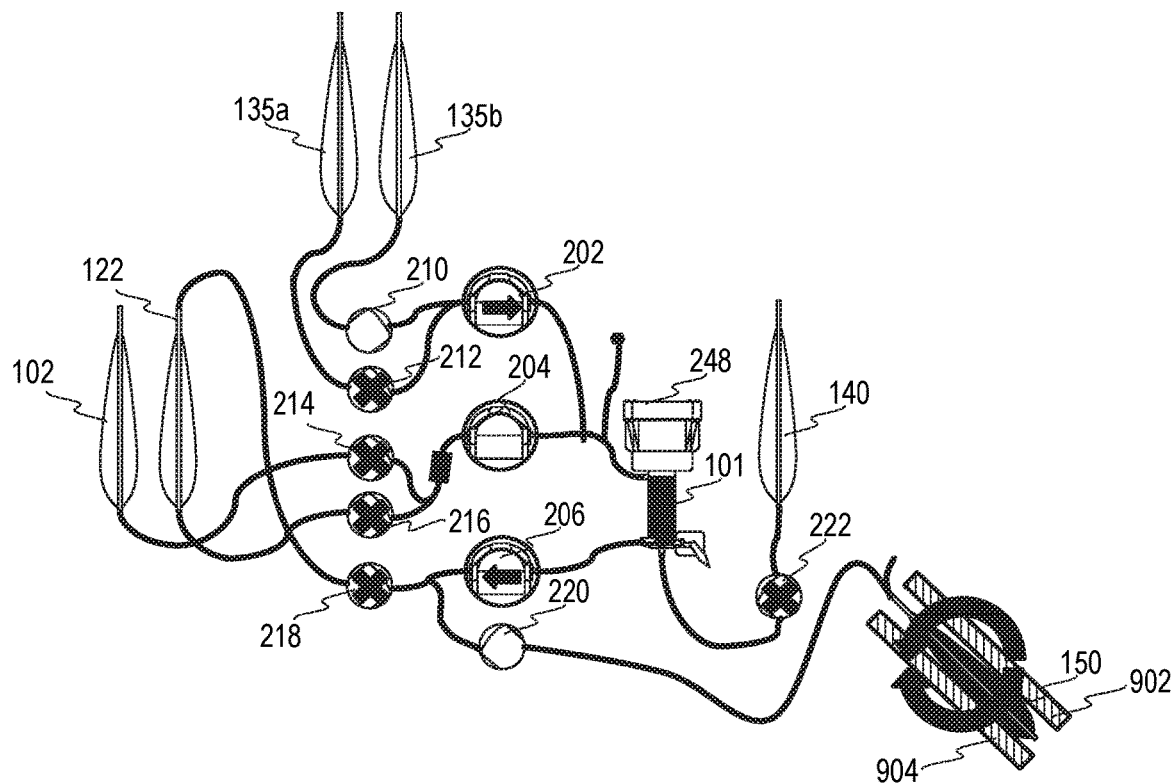
Figure 32:
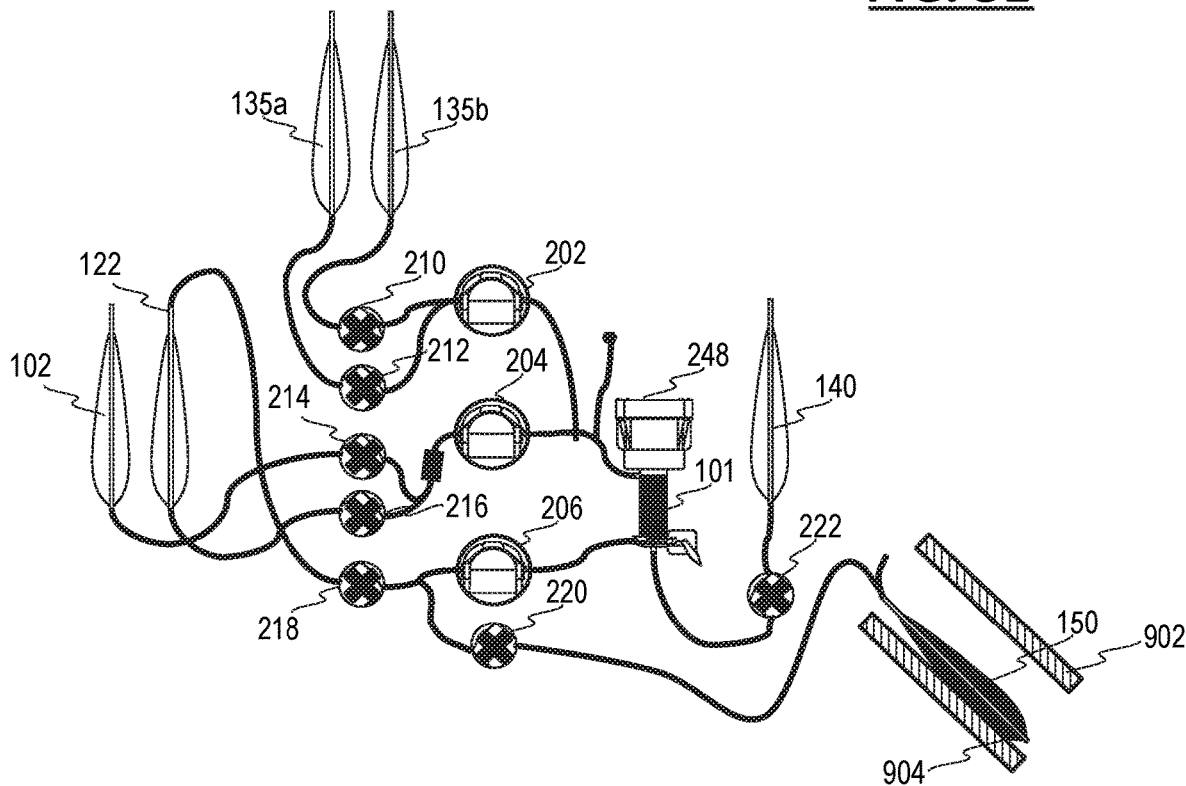

At this point, the method 800 is almost complete. At block 838, wash solution is pumped from container 135*b* into the container 150 by closing clamp 214, opening clamp 210, and operating pumps 202, 206 as illustrated in FIG. 31. The container 150 may also be agitated by varying the inclination of the container 150 either at the same time as fluid is transferred to the container 150 or shortly thereafter. Sufficient fluid may be added to the container 150 to bring the volume of the container to the desired volume. Finally, the magnet is deactivated (and plate 902 may be spaced from plate 904 as well) at block 840, permitting the target cells with associated magnetic particles to be released into the remainder of the container 150 (see FIG. 32).

Thus, an improved method and system have been disclosed for the processing of biological cells. The description provided above is intended for illustrative purposes only and is not intended to limit the scope of the invention to any specific method, system, or apparatus, or device described herein except as may be explicitly delineated above.

Other Aspects

Aspect 1. A cell processing system comprising:
a processor connectable to a source container filled with a biological fluid, the processor comprising:
a spinning membrane configured in a first state to receive and separate a fluid into two streams of material, a first stream exiting at a first outlet and a second stream exiting at a second outlet; and
a first container selectively connected to the first outlet;
a controller coupled to the processor and configured:
to operate the separator in the first state to receive biological fluid from the source container and to direct the first stream to the first container, to pause to permit a conjugated antibody bead to be added to the first container to form conjugated antibody bead-target cell complexes, to operate the separator in the first state to receive the contents from the first container.

Aspect 2. The system according to aspect 1, wherein the processor comprises a magnet, and the controller is configured to operate the separator in the first state to receive the contents from the first container with the magnet applied to the first container.

Aspect 3. The system according to aspect 1 or 2, wherein the spinning membrane is configured to operate in a second state to receive and mix materials and direct the mixed materials to the first outlet, and the controller is configured to operate the separator in the second state after the first pause with the container connected to the first outlet; and to operate the separator in the first state to receive the contents from the first container after operating the separator in the second state.

Aspect 4. The system according to any one of aspects 1-3, wherein the first container is attached to a second container including media, and the controller is configured to add media from the second container to the first container, and to operate the separator in the second state to receive the contents from the first container after the media is added to the first container.

Aspect 5. The system according to any one of aspects 1-4, wherein the processor comprises reusable hardware, and a disposable circuit, the disposable circuit comprising the spinning membrane and the first container.

Aspect 6. The system according to aspect 5, wherein the disposable circuit is a closed circuit.

Aspect 7. A method of processing cells using a closed circuit comprising a spinning membrane and a first container, comprising:
separating target cells using the spinning membrane, the target cells directed into the first container;
adding conjugated antibody beads to the first container;
incubating the target cells with the conjugated antibody beads in the first container;
separating conjugated antibody bead-target cell complex.

Aspect 8. The method according to aspect 7, wherein separating the conjugated antibody bead-target cell complex comprises separating the conjugated antibody bead-target cell complex using the spinning membrane.

Aspect 9. The method according to aspect 7, wherein separating the conjugated antibody bead-target cell complex comprises applying a magnet to the first container while directing the contents of the first container to the spinning membrane.

Aspect 10. The method according to any one of aspects 7-9, further comprising:
adding media to the separated conjugated antibody bead-target cell complex; passing the media and separated conjugated antibody bead-target cell complex through the spinning membrane and returning to the first container.

Aspect 11. The method according to aspect 10, wherein adding media to the separated conjugated antibody bead-target cell complex, and passing the media and separated conjugated antibody bead-target cell complex through the spinning membrane are repeated.

Aspect 12. The method according to any one of aspects 7-11, wherein the spinning membrane and the first container define a closed circuit.

Aspect 13. A cell processing system comprising: a first processor connectable to a source container filled with a biological fluid, the first processor comprising:
a separator configured to separate the biological fluid from the source container into at least two streams of material; and
a first container configured to receive one of the at least two streams along a first fluid pathway;
a second processor connectable to the first container, the second processor comprising:
a magnetic separator configured to separate target cells, the target cells being associated with magnetic particles; and
a second container associated with the magnetic separator, the second container connected to the first container along a second fluid pathway; and
one of the first processor and the second processor comprising at least one pump configured to transfer material between the separator and the first container along the first fluid pathway, and between the first container and the second container along the second fluid pathway; and at least one controller coupled to the first processor and the second processor.

Aspect 14. The cell processing system according to aspect 13, wherein a closed fluid circuit defines in part the first and second processors, the closed fluid circuit comprising and connecting the first and second containers.

Aspect 15. The cell processing system according to aspect 13 or 14, wherein the magnetic separator comprises first and second opposing plates, at least the first plate translatable relative to the second plate, and the second container disposed between the first and second plates.

Aspect 16. The cell processing system according to aspect 15, wherein the first and second plates are mounted on an axle, the first and second plates being pivotable about the axle to change the inclination of the first and second plates and the second container disposed between the first and second plates.

Aspect 17. The cell processing system according to any one of the aspects 13-16, wherein the at least one controller is configured to operate the first processor to associate the target cells with the magnetic particles in the first container, to operate the at least one pump to move the target cells with associated magnetic particles to the magnetic separator, and to operate the magnetic separator to select the target cells.

Aspect 18. The cell processing system according to aspect 17, wherein the at least one controller comprises a processor and the processor is programmed to operate the first processor to associate the target cells with the magnetic particles in the first container, to operate the at least one pump to move the target cells with associated magnetic particles to the magnetic separator, and to operate the magnetic separator to select the target cells.

Aspect 19. The cell processing system according to aspect 17, wherein the at least one controller is configured to operate the at least one pump to circulate the target cells and the magnetic particles between the first container and the separator during association of the target cells with the magnetic particles.

Aspect 20. The cell processing system according to any one of the aspects 13-19, wherein the first processor comprises a third container connected to the first container, and the at least one pump is configured to transfer material between the second container and the third container.

Aspect 21. The cell processing system according to any one of the aspects 13-20, wherein the separator of the first processor comprises a spinning membrane separator.

Aspect 22. A cell processing method comprising: separating a biological fluid into at least two streams, one of the streams including target cells;
associating magnetic particles with the target cells; and
separating the target cells using a magnetic field.

Aspect 23. The cell processing method according to aspect 22, selecting the target cells using a magnetic field comprises disposing a magnet adjacent the target cells associated with magnetic particles.

Aspect 24. The cell processing method according to aspect 23, wherein the target cells associated with magnetic particles are disposed in a container that is disposed between two moveable plates, one of the plates comprising a magnet that is translatable relative to the container.

Aspect 25. The cell processing method according to any one of aspects 22-24, wherein separating the biological fluid comprises separating the biological fluid into a first fraction comprising at least white blood cells and a second fraction comprising at least platelets, the target cells comprising the white blood cells.

Aspect 26. The cell processing method according to aspect 25, wherein separating the biological fluid into at least two streams comprises passing the biological fluid through a spinning membrane separator.

Aspect 27. The cell processing method according to any one of aspects 22-26, wherein associating magnetic particles with the target cells comprises associating monoclonal antibodies with the target cells, and associating magnetic particles with the monoclonal antibodies associated with the target cells.

Aspect 28. The cell processing method according to aspect 27, wherein:
associating monoclonal antibodies with the target cells comprises adding the monoclonal antibodies to the target cells in a container and subsequently passing the contents of the container through a spinning membrane separator to mix the contents of the container; and
associating magnetic particles with the monoclonal antibodies comprises adding the magnetic particles to the monoclonal antibodies associated with the target cells in the container and subsequently passing the contents of the container through a spinning membrane separator to mix the contents of the container.

Aspect 29. The cell processing method according to aspect 28, wherein associating monoclonal antibodies with the target cells further comprises removing unassociated monoclonal antibodies from the contents of the container by passing the contents of the container through the spinning membrane separator.

Aspect 30. The cell processing method according to aspect 28, wherein associating magnetic particles with the monoclonal antibodies further comprises removing unassociated magnetic particles from the contents of the container by passing the contents of the container through the spinning membrane separator.

Aspect 31. The cell processing method according to any one of aspects 22-30, wherein the method is performed within a single closed fluid circuit Aspect 32. A cell processing system comprising:
at least one processor connectable to a source container filled with a biological fluid, the at least one processor comprising:
a spinning membrane configured to receive and separate target cells from the biological fluid, the target cells exiting at a first outlet;
one or more containers selectively connected to the first outlet; and
a magnet;
a controller coupled to the at least one processor and configured:
to operate the spinning membrane to receive biological fluid from the source container and to direct the target cells to one of the one or more containers,
to pause to permit magnetic particles to be associated with the target cells,
to operate the spinning membrane to receive the contents of one of the one or more containers with the magnet applied to the target cells associated with the magnetic particles.

Aspect 33. The cell processing system according to aspect 32, wherein the controller is configured to pause to permit a conjugated antibody bead to be added to the one or more containers and to permit the conjugated antibody bead to form conjugated antibody bead-target cell complexes with the target cells.

Aspect 34 The cell processing system according to aspect 33, wherein the controller is configured to operate the spinning membrane to mix the conjugated antibody beads with the target cells.

Aspect 35. The cell processing system according to aspect 32, wherein the controller is configured to pause to permit monoclonal antibodies to be added to the target cells to associate the monoclonal antibodies with the target cells, and to permit magnetic particles to be added to the target cells associated with the monoclonal antibodies to associate the magnetic particles with the target cells.

Aspect 36. The cell processing system according to aspect 35, wherein the controller is configured to operate the spinning membrane to mix the monoclonal antibodies with the target cells, and wherein the controller is configured to operate the spinning membrane to mix the magnetic particles with the target cells associated with the monoclonal antibodies.

Aspect 37. The cell processing system according to aspect 32, further comprising:
  a magnetic separator having first and second opposing plates, the magnet associated with the first plate.
  at least the first plate translatable relative to the second plate, and one of the one or more containers disposed between the first and second plates.

Aspect 38. The cell processing system according to aspect 37, wherein the first and second plates are mounted on an axle, the first and second plates being pivotable about the axle to change the inclination of the first and second plates and the second container disposed between the first and second plates.

Aspect 39. The cell processing system according to any one of aspects 32-38, wherein the at least one processor comprises reusable hardware, and a disposable circuit, the disposable circuit comprising the spinning membrane and the one or more containers.

Aspect 40. The cell processing system according to aspect 39, wherein the disposable circuit is a closed circuit.

Aspect 41. A cell processing method comprising:
  separating a biological fluid into at least two streams, one of the streams including target cells;
  associating magnetic particles with the target cells; and
  separating the target cells associated with the magnetic particles using a magnetic field.

Aspect 42. The cell processing method according to aspect 41, wherein associating magnetic particles with the target cells comprises adding conjugated antibody beads to the target cells in a container, and incubating the target cells with the conjugated antibody beads.

Aspect 43. The cell processing method according to aspect 42, further comprising subsequently passing the contents of the container through a spinning membrane to mix the contents of the container.

Aspect 44. The cell processing method according to aspect 41, wherein associating magnetic particles with the target cells comprises associating monoclonal antibodies with the target cells, and associating magnetic particles with the monoclonal antibodies associated with the target cells Aspect 45. The cell processing method according to aspect 44, wherein:
  associating monoclonal antibodies with the target cells comprises adding the monoclonal antibodies to the target cells in a container and subsequently passing the contents of the container through a spinning membrane to mix the contents of the container; and
  associating magnetic particles with the monoclonal antibodies comprises adding the magnetic particles to the monoclonal antibodies associated with the target cells in the container and subsequently passing the contents of the container through a spinning membrane to mix the contents of the container.

Aspect 46. The cell processing method according to any one of aspects 41-45, selecting the target cells using a magnetic field comprises disposing a magnet adjacent the target cells associated with magnetic particles.

Aspect 47. The cell processing method according to aspect 46, wherein the target cells associated with magnetic particles are disposed in a container that is disposed between two moveable plates, one of the plates comprising a magnet that is translatable relative to the container.

Aspect 48. The cell processing method according to aspect 47, wherein the two moveable plates are mounted on an axle, the first and second plates being pivotable about the axle.

Aspect 49. The cell processing method according to any one of aspects 41-48, wherein separating the biological fluid into at least two streams comprises passing the biological fluid through a spinning membrane.

Aspect 50. The cell processing method according to any one of aspects 41-49, wherein the method is performed within a single closed fluid circuit.

The invention claimed is:

1. A cell processing system comprising:
  at least one processor connectable to a source container filled with a biological fluid, the at least one processor comprising:
    a spinning membrane configured to receive and separate target cells from the biological fluid, the target cells exiting at a first outlet;
    at least a first container and a second container selectively connected to the first outlet; and
    a magnet; and
  a controller coupled to the at least one processor and configured:
    to operate the spinning membrane to receive biological fluid from the source container and to direct the target cells to the first container;
    to pause operation of the processor to permit magnetic particles to be associated with the target cells in the first container;
    to operate the spinning membrane to receive the contents of the first container with the magnet applied to the target cells associated with the magnetic particles in the first container;
    to remove and/or deactivate the magnet applied to the target cells associated with the magnetic particles in the first container;
    to transfer the target cells to the second container after removal and/or deactivation of the magnet; and
    to prompt an operator to remove the second container after the target cells are transferred to the second container.

2. The cell processing system according to claim 1, wherein the controller is configured to operate the spinning membrane to receive the contents of the first container with the magnet applied to remove materials other than the target cells associated with the magnetic particles.

3. The cell processing system according to claim 1, wherein the controller is configured to pause operation of the processor to permit a conjugated antibody bead to be added to the first container and to permit the conjugated antibody bead to form conjugated antibody bead-target cell complexes with the target cells.

4. The cell processing system according to claim 3, wherein the controller is configured to operate the spinning membrane to mix the conjugated antibody beads with the target cells.

5. The cell processing system according to claim 1, wherein the controller is configured to pause operation of the processor to permit monoclonal antibodies to be added to the target cells to associate the monoclonal antibodies with the target cells, and to permit magnetic particles to be added to the target cells associated with the monoclonal antibodies to associate the magnetic particles with the target cells.

6. The cell processing system according to claim 5, wherein the controller is configured to operate the spinning membrane to mix the monoclonal antibodies with the target cells, and wherein the controller is configured to operate the spinning membrane to mix the magnetic particles with the target cells associated with the monoclonal antibodies.

7. The cell processing system according to claim 1, wherein the controller is configured, after removal and/or deactivation of the magnet and before transfer of the target cells to the second container, to incubate and circulate the target cells in the first container through the spinning membrane.

8. The cell processing system according to claim 7, wherein the controller is configured to introduce fresh media into the first container after removal and/or deactivation of the magnet and before transfer of the target cells to the second container.

9. The cell processing system according to claim 7, wherein the controller is configured, after removal and/or deactivation of the magnet and before transfer of the target cells to the second container, to activate a mechanical agitator associated with the first container to mechanically agitate the target cells in the first container.

10. The cell processing system according to claim 1, wherein the at least one processor comprises reusable hardware, and a disposable circuit, the disposable circuit comprising the spinning membrane and the first container.

11. The cell processing system according to claim 10, wherein the disposable circuit is a closed circuit.

12. A method of operating a cell processing system, the cell processing system comprising at least one processor connectable to a source container filled with a biological fluid, the at least one processor comprising a spinning membrane configured to receive and separate target cells from the biological fluid, the target cells exiting at a first outlet, at least a first container and a second container selectively connected to the first outlet, and a magnet; and a controller coupled to the at least one processor, the method comprising:

operating the spinning membrane to receive biological fluid from the source container and to direct the target cells to the first container;

pausing operation of the processor to permit magnetic particles to be associated with the target cells in the first container;

operating the spinning membrane to receive the contents of the first container with the magnet applied to the target cells associated with the magnetic particles in the first container;

removing and/or deactivating the magnet applied to the target cells associated with the magnetic particles in the first container;

transferring the target cells to a second container after removal and/or deactivation of the magnet; and prompting an operator to remove the second container after the target cells are transferred to the second container.

13. The method according to claim 12, further comprising, when the operation of the processor is paused, adding a conjugated antibody bead to the first container, and forming conjugated antibody bead-target cell complexes between the conjugated antibody bead and the target cells.

14. The method according to claim 13, further comprising operating the spinning membrane to mix the conjugated antibody beads with the target cells.

15. The method according to claim 13, further comprising decoupling the conjugated antibody bead from the target cells after removing and/or deactivating the magnet.

16. The method according to claim 12, further comprising, when the operation of the processor is paused, adding monoclonal antibodies to the target cells to associate the monoclonal antibodies with the target cells, and adding magnetic particles to the target cells associated with the monoclonal antibodies to associate the magnetic particles with the target cells.

17. The method according to claim 16, further comprising operating the spinning membrane to mix the monoclonal antibodies with the target cells, and operating the spinning membrane to mix the magnetic particles with the target cells associated with the monoclonal antibodies.

18. The method according to claim 16, further comprising decoupling the monoclonal antibodies from the target cells after removing and/or deactivating the magnet.

19. The method according to claim 12, further comprising, after removal and/or deactivation of the magnet and before transfer of the target cells to the second container, incubating and circulating the target cells in the first container through the spinning membrane.

20. The method according to claim 19, further comprising, after removal and/or deactivation of the magnet and before transfer of the target cells to the second container, mechanically agitating the target cells in the first container.

* * * * *